United States Patent [19]
Lin et al.

[11] Patent Number: 5,726,319
[45] Date of Patent: Mar. 10, 1998

[54] BIPHENYL SUBSTITUTED DIPEPTIDE ANALOGS PROMOTE RELEASE OF GROWTH HORMONE

[75] Inventors: Peter Lin, Iselin; William R. Schoen, Edison; Judith M. Pisano, Cliffside Park; Matthew J. Wyvratt, Mountainside, all of N.J.

[73] Assignee: Merck & Co., Inc., Rahway, N.J.

[21] Appl. No.: 510,026

[22] Filed: Aug. 1, 1995

Related U.S. Application Data

[63] Continuation of Ser. No. 175,809, Dec. 30, 1993, abandoned, which is a continuation-in-part of Ser. No. 973,142, Nov. 6, 1992, abandoned.

[51] Int. Cl.$^6$ .................. C07D 257/00; A61K 38/00
[52] U.S. Cl. .................. 548/253; 514/19; 514/235.8; 546/348; 549/29; 549/49; 549/462; 549/505; 548/146; 548/215; 548/250; 548/255; 548/262; 548/335.1; 548/361.1; 548/400; 548/484
[58] Field of Search .................. 514/19, 235.8; 546/348; 548/146, 250, 253, 255, 262, 335.1, 215, 400, 484, 361.1; 549/29, 49, 462, 505

[56] References Cited

U.S. PATENT DOCUMENTS 4,411,890  10/1983  Momany .................. 424/177
5,206,235  4/1993  Fisher et al. .................. 514/213

FOREIGN PATENT DOCUMENTS

WO95/14666  6/1995  WIPO.

OTHER PUBLICATIONS

Fujii, et al., Chem. Pharm. Bull., 32(3), 1200–1208 (1994), "Synthesis of Growth Hormone Releasing Factor (GRF–37–NH2) and Nalpha–Biotinyl–GRF–44–NH2".
Sato, et al., Int. J. Peptide Protein Res., 38, 340–345 (1991), "Solid Phase Synthesis of Human Growth Hormone-Releasing Factor Analogs Containing a Bicyclic Beta–turn Dipeptide".
Merck Manual of Diagnosis and Therapy, Fifteenth Ed, 950–955 (1987).
Rudinger, *Peptides Hormones* (Ed. J. Parsons, University Park Press, Jun. 1976) pp. 1–7.
Melmon et al. "Drug Interactions" Goodman & Gilman, *The Pharmacological Basis of Therapeutics* 6th Ed (MacMillan Publishing 1980) pp. 1738–1740.
Meier et al. J. Org. Chem. vol. 56 No. 18 (Aug. 1991) pp. 5380–5384.

*Primary Examiner*—Cecilia J. Tsang
*Assistant Examiner*—Bennett Celsa
*Attorney, Agent, or Firm*—J. Eric Thies; David L. Rose

[57] ABSTRACT

There are disclosed certain compounds identified as substituted dipeptide analogs which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such substituted dipeptide analogs as the active ingredient thereof are also disclosed.

7 Claims, No Drawings

BIPHENYL SUBSTITUTED DIPEPTIDE ANALOGS PROMOTE RELEASE OF GROWTH HORMONE

CROSS REFERENCE TO RELATED APPLICATIONS

This application is a continuation of application Ser. No. 08/175,809, filed Dec. 30, 1993 (Abandoned), which is a continuation-in-part of application Ser. No. 07/973142 filed 6 Nov. 1992 (Abandoned).

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are highly substituted dipeptide analogs for promoting the release of growth hormone which are stable under various physiological conditions which may be administered parenterally, nasally or by the oral route.

SUMMARY OF THE INVENTION

The instant invention covers certain substituted dipeptide analogs which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the diphenyl substituted dipeptide analogs. It is a further object of this invention to describe procedures for the preparation of such com-pounds. A still further object is to describe the use of such compounds to increase the secretion of growth hormone in humans and animals. A still further object of this invention is to describe compositions containing the substituted dipeptide analogs for the use of treating humans and animals so as to increase the level of growth hormone secretions. Further objects will become apparent from a reading of the following description.

DESCRIPTION OF THE INVENTION

The novel substituted dipeptide analogs of the instant invention are best described in the following structural formula I:

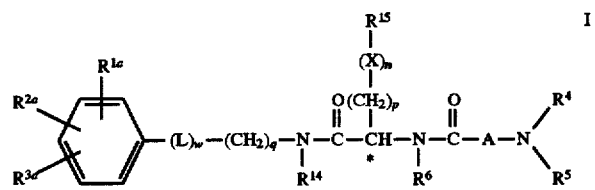

where L is

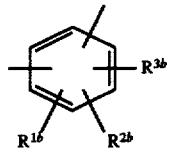

n is 0 or 1;
p is 0 to 6;
q is 0 to 4;
w is 0 or 1;
X is C=O, O, S(O)$_m$,

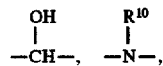

—CH=CH—;
m is 0 to 2;
$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, $C_1$–$C_3$ perfluoroalkoxy, —S(O)$_m$— $R^{7a}$, cyano, nitro, $R^{7b}$O(CH$_2$)$_v$—, $R^{7b}$COO(CH$_2$)$_v$—, $R^{7b}$OCO—(CH$_2$)$_v$—, $R^4R^5$N(CH$_2$)$_v$—, $R^{7b}$CON(R$^4$)(CH$_2$)$_v$—, $R^4R^5$NCO(CH$_2$)$_v$—, $R^4R^5$— NCOO(CH$_2$)$_v$—, phenyl or substituted phenyl where the substituents are from 1 to 3 of halogen, $C_1$–$C_6$ alkyl, $C_1$–$C_6$ alkoxy, or hydroxy; $R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3;

$R^{3a}$ and $R^{3b}$ are independently hydrogen, $R^9$, $C_1$–$C_6$ alkyl substituted with $R^9$, phenyl substituted with $R^9$, or phenoxy substituted with $R^9$;

$R^9$ is

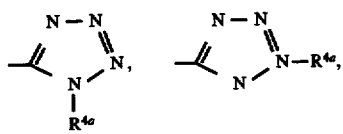

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{4b}R^{12c}N(CH_2)_v$—, $R^{12a}R^{12b}NCO(CH_2)_v$—, $R^{12a}R^{12b}NCS(CH_2)_v$—, $R^{4b}R^{12a}NN(R^{12b})CO(CH_2)_v$—, $R^{4b}R^{12a}NN(R^{12b})CS(CH_2)_v$—, $R^{4b}R^{12a}NCON(R^{12c})(CH_2)_v$—, $R^{4b}R^{12a}NCSN(R^{12c})(CH_2)_v$—, $R^{4b}R^{12a}NN(R^{12b})CON(R^{12c})(CH_2)_v$—, $R^{4b}R^{12a}NN(R^{12b})CSN(R^{12c})(CH_2)_v$—, $R^{4b}R^{12a}NN(R^{12b})$—COO$(CH_2)_v$—, $R^{4b}R^{12a}NCOO(CH_2)_v$—, or $R^{13}OCON(R^{12c})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{12a}$ and $R^{12c}$, or $R^{4b}$ and $R^{12a}$, or $R^{4b}$ and $R^{12a}$, or $R^{4b}$ and $R^{12c}$, or $R^{13}$ and $R^{12c}$, can be taken together to form —$(CH_2)_r$, —B—$(CH_2)_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$–$C_3$ perfluoroalkyl, $C_1$–$C_6$ alkyl, substituted $C_1$–$C_6$ alkyl, where the substituents are hydroxy, —NR$^{10}$R$^{11}$, carboxy, phenyl or substituted phenyl; phenyl or substituted phenyl where the substituents on the phenyl are from 1 to 3 of halogen, $C_1$–$C_6$ alkyl, $C_1$–$C_6$ alkoxy or hydroxy where $R^{10}$ and $R^{11}$ are as defined;

$R^{14}$ is hydrogen, $R^1$, $R^2$ independently disubstituted phenyl, $C_1$–$C_{10}$ alkyl or substituted $C_1$–$C_{10}$ alkyl where the substituents are from 1 to 3 of imidazolyl, indolyl, hydroxy, fluoro, S(O)$_m$R$^{7a}$, $C_1$–$C_6$ alkoxy, $C_3$–$C_7$ cycloalkyl, $R^1$, $R^2$ independently disubstituted phenyl, $C_1$–$C_3$ alkoxy, $R^1$, $R^2$ independently disubstituted phenyl $C_1$–$C_5$ alkanoyloxy, $C_1$–$C_5$ alkoxycarbonyl, carboxy, formyl or —NR$^{10}$R$^{11}$ where $R^1$, $R^2$, $R^{10}$ and $R^{11}$ are as defined;

$R^{15}$ is hydrogen, trifluoromethyl, $R^1$, $R^2$ independently disubstituted phenyl, $R^1$, $R^2$ independently disubstituted naphthyl, $C_3$–$C_7$ cycloalkyl, $C_1$–$C_{10}$ alkyl, substituted $C_1$–$C_{10}$ alkyl where the substituents are from 1 to 3 of hydroxy, fluoro, S(O)$_m$R$^{7a}$, $C_1$–$C_6$ alkoxy, $C_3$–$C_7$ cycloalkyl, $R^1$, $R^2$ independently disubstituted phenyl, $R^1$, $R^2$ independently disubstituted phenyl $C_1$–$C_3$ alkoxy, $R^1$, $R^2$ independently disubstituted naphthyl, $R^1$, $R^2$ independently disubstituted naphthyl $C_1$–$C_3$ alkoxy, $C_1$–$C_5$ alkanoyloxy, $C_1$–$C_5$ alkoxycarbonyl, carboxy, formyl, —NR$^{10}$R$^{11}$ or $R^1$, $R^2$ independently disubstituted heterocycle, where the heterocycle is imidazole, thiophene, furan, pyrrole, oxazole, thiazole, triazole, tetrazole, pyridine, benzofuran, benzothiophene, benzimidazole, indole, 7-azaindole, oxindole or indazole; where $R^1$, $R^2$, $R^{10}$ and $R^{11}$ are as defined above;

$R^4$, $R^{4a}$, $R^{4b}$, $R^5$ and $R^{5a}$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_{20}$-alkanoyloxy, $C_1$–$C_5$ alkoxycarbonyl, carboxy, formyl, or —NR$^{10}$R$^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl, $C_1$–$C_5$-alkanoyl or $C_1$–$C_6$ alkyl; or $R^4$ and $R^5$ can be taken together to form —$(CH_2)_r$B$(CH_2)_s$— where B, r, s, $R^1$ and $R^{10}$ are as defined above;

$R^6$ is hydrogen, $C_1$–$C_{10}$ alkyl, phenyl or phenyl $C_1$–$C_{10}$ alkyl;

A is

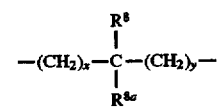

where x and y are independently 0–3;

$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, S(O)$_m$R$^{7a}$, $C_1$–$C_6$ alkoxy, $C_3$–$C_7$ cycloalkyl, $R^1$, $R^2$ independently disubstituted phenyl $C_1$–$C_3$ alkoxy, $R^1$, $R^2$ independently disubstituted phenyl, $C_1$–$C_5$-alkanoyloxy, $C_1$–$C_5$ alkoxycarbonyl, carboxy, formyl, or —NR$^{10}$R$^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;

p is 0 to 4;

q is 0 to 2;

w is 0 or 1;

X is O, S(O)$_m$,

—CH=CH—;

m is 0 to 2;

R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_3$ perfluoroalkyl, C$_1$–C$_6$ alkyl, substituted C$_1$–C$_6$ alkyl, where the substituents are phenyl; phenyl and v is 0 to 2;

R$^{3a}$ and R$^{3b}$ are independently hydrogen, R$^9$, C$_1$–C$_6$ alkyl substituted with R$^9$, phenyl substituted with R$^9$, or phenoxy substituted with R$^9$;

R$^9$ is as defined above;

R$^{12a}$, R$^{12b}$ and R$^{12c}$ are independently R$^{5a}$, OR$^{5a}$, or COR$^{5a}$; R$^{12a}$ and R$^{12b}$, or R$^{12b}$ and R$^{12c}$, or R$^{13}$ and R$^{12b}$ or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3, R$^1$ is as defined above and R$^{10}$ is hydrogen, C$_1$–C$_6$ alkyl, phenyl C$_1$–C$_6$ alkyl or C$_1$–C$_5$ alkanoyl-C$_1$–C$_6$ alkyl;

R$^{13}$ is C$_1$–C$_3$ perfluoroalkyl, C$_1$–C$_6$ alkyl, substituted C$_1$–C$_6$ alkyl, where the substituents are hydroxy, NR$^{10}$R$^{11}$, carboxy, phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^{14}$ and R$^{15}$ are as defined above;

R$^4$, R$^{4a}$, R$^{4b}$, R$^5$ and R$^{5a}$ are independently hydrogen, phenyl, substituted phenyl, C$_1$–C$_{10}$ alkyl, substituted C$_1$–C$_{10}$ alkyl, where the substituents on the alkyl or phenyl are from 1 to 5 of hydroxy, C$_1$–C$_6$ alkoxy, C$_3$–C$_7$ cycloalkyl, fluoro, R$^1$ substituted or R$^1$, R$^2$ independently disubstituted phenyl C$_1$–C$_3$ alkoxy, R$^1$ substituted or R$^1$, R$^2$ independently disubstituted phenyl, C$_1$–C$_{20}$-alkanoyloxy, C$_1$–C$_5$ alkoxycarbonyl, carboxy or formyl;

R$^4$ and R$^5$ can be taken together to form —(CH$_2$)$_r$B(CH$_2$)$_s$— where B is CHR$^1$, O, S(O)$_m$ or N—R$^{10}$, r and s are independently 1 to 3 and R$^1$ and R$^{10}$ are as defined above;

R$^6$ is hydrogen, C$_1$–C$_{10}$ alkyl or phenyl C$_1$–C$_{10}$ alkyl;

A is

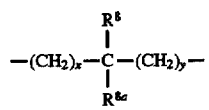

where x and y are independently 0–2;

R$^8$, R$^{8a}$ and R$^{8b}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$, R$^2$ independently disubstituted phenyl, C$_1$–C$_5$-alkanoyloxy, C$_1$–C$_5$ alkoxycarbonyl, carboxy, formyl, —NR$^{10}$R$^{11}$ where R$^{10}$ and R$^{11}$ are independently hydrogen, C$_1$–C$_6$ alkyl, or C$_1$–C$_5$ alkanoyl-C$_1$–C$_6$ alkyl; or R$^8$ and R$^{8a}$ can be taken together to form —(CH$_2$)$_t$— where t is 2 to 4; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms; and pharmaceutically acceptable salts thereof.

Additional preferred compounds are realized in the above structural formula when:

n is 0 or 1;

p is 0 to 3;

q is 0 to 2;

w is 0 or 1;

X is O, S(O)$_m$ or —CH=CH—;

m is 0 or 1;

R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_6$ alkyl, substituted C$_1$–C$_6$ alkyl, where the substituents are phenyl and v is 0 to 2;

R$^{3a}$ and R$^{3b}$ are independently hydrogen, R$^9$, C$_1$–C$_6$ alkyl substituted with R$^9$, phenyl substituted with R$^9$, or phenoxy substituted with R$^9$;

R$^9$ is as defined above;

R$^{12a}$, R$^{12b}$ and R$^{12c}$ are independently R$^{5a}$ or OR$^{5a}$. R$^{12a}$ and R$^{12b}$, or R$^{12b}$ and R$^{12c}$, or R$^{13}$ and R$^{12b}$ or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$–C$_6$ alkyl or C$_1$–C$_5$ alkanoyl-C$_1$–C$_6$ alkyl;

R$^{13}$ is C$_1$–C$_6$ alkyl, substituted C$_1$–C$_6$ alkyl, where the substituents are phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^{14}$ and R$^{15}$ are as defined above;

R$^4$, R$^{4a}$, R$^{4b}$, R$^5$ and R$^{5a}$ are independently hydrogen, C$_1$–C$_{10}$ alkyl, substituted C$_1$–C$_{10}$ alkyl, where the substituents on the alkyl are from 1 to 5 of hydroxy, C$_1$–C$_6$ alkoxy, fluoro, R$^1$ substituted or R$^1$, R$^2$ independently disubstituted phenyl, C$_1$–C$_{20}$-alkanoyloxy, C$_1$–C$_5$ alkoxycarbonyl or carboxy;

R$^6$ is hydrogen or C$_1$–C$_{10}$ alkyl;

A is

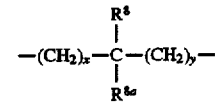

where x and y are independently 0–2;

R$^8$, R$^{8a}$ and R$^{8b}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$ substituted or R$^1$, R$^2$ independently disubstituted phenyl, C$_1$–C$_5$-alkanoyloxy, C$_1$–C$_5$ alkoxycarbonyl, carboxy; or R$^8$ and R$^{8a}$ can be taken together to form —(CH$_2$)$_t$— where t is 2; or R⁸ and R⁸ᵃ can independently be joined to one or both of R⁴ and R⁵ to form alkylene bridges between the terminal nitrogen and the alkyl portion of the A group wherein the bridge contains from 1 to 5 carbon atoms;

and pharmaceutically acceptable salts thereof.

Still further preferred compounds of the instant invention are realized in the above structural formula when;

n is 0 or 1;
p is 0 to 2;
q is 1;
w is 1;
X is O, S(O)$_m$;
m is 0 or 1;

R¹, R², R¹ᵃ, R²ᵃ, R¹ᵇ, and R²ᵇ are independently hydrogen, halogen, C₁–C₇ alkyl, C₁–C₃ perfluoroalkyl, —S(O)$_m$R⁷ᵃ, R⁷ᵇO(CH₂)$_v$—, R⁷ᵇCOO(CH₂)$_v$—, phenyl or substituted phenyl where the substituents are from 1 to 3 of halogen, C₁–C₆ alkyl, C₁–C₆ alkoxy, or hydroxy; R⁷ᵃ and R⁷ᵇ are independently hydrogen, C₁–C₆ alkyl, substituted C₁–C₆ alkyl, where the substituents are phenyl and v is 0 or 1;

R³ᵃ and R³ᵇ are independently hydrogen, R⁹, or C₁–C₆ alkyl substituted with R⁹;

R⁹ is as defined above;

R¹²ᵃ, R¹²ᵇ and R¹²ᶜ are independently R⁵ᵃ, R¹²ᵃ and R¹²ᵇ, or R¹²ᵇ and R¹²ᶜ, or R¹³ and R¹²ᵇ or R¹²ᵃ and R⁴ᵇ can be taken together to form —(CH₂)$_r$—B—(CH₂)$_s$— where B is CHR¹, O, S(O)$_m$, or NR¹⁰, m is 0, 1 or 2, r and s are independently 0 to 2, R¹ is as defined above and R¹⁰ is hydrogen, C₁–C₆ alkyl or C₁–C₅ alkanoyl C₁–C₆ alkyl;

R¹³ is C₁–C₆ alkyl, substituted C₁–C₆ alkyl, where the substituents are phenyl or substituted phenyl; phenyl or substituted phenyl where the substituents on the phenyl are from 1 to 3 of halogen, C₁–C₆ alkyl, C₁–C₆ alkoxy or hydroxy;

R¹⁴ and R¹⁵ are as defined above;

R⁴, R⁴ᵃ, R⁴ᵇ, R⁵ and R⁵ᵃ are independently hydrogen, C₁–C₁₀ alkyl, substituted C₁–C₁₀ alkyl, where the substituents on the alkyl are from 1 to 3 of hydroxy, C₁–C₃ alkoxy, fluoro, R¹ substituted or R¹, R² independently disubstituted phenyl, C₁–C₂₀ alkanoyloxy, C₁–C₅ alkoxycarbonyl or carboxy;

R⁶ is hydrogen;

A is

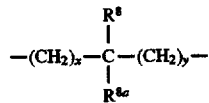

where x and y are independently 0–1;

R⁸, R⁸ᵃ and R⁸ᵇ are independently hydrogen, C₁–C₁₀ alkyl, substituted C₁–C₁₀ alkyl where the substituents are from 1 to 3 of imidazolyl, indolyl, hydroxy, fluoro, S(O)$_m$R⁷ᵃ, C₁–C₆ alkoxy, R¹ substituted or R¹, R² independently disubstituted phenyl, C₁–C₅-alkanoyloxy, C₁–C₅ alkoxycarbonyl, carboxy; or R⁸ and R⁸ᵃ can be taken together to form —(CH₂)$_t$— where t is 2; and R⁸ and R⁸ᵃ can independently be joined to one or both of R⁴ and R⁵ to form alkylene bridges between the terminal nitrogen and the alkyl portion of the A group wherein the bridge contains from 1 to 5 carbon atoms;

and pharmaceutically acceptable salts thereof.

Representative preferred growth hormone releasing compounds of the present invention include the following:

1. (R)-α-[(3-Amino-3-methyl-1-oxobutyl)amino]-N-[[2'-(1H-tetrazol-5-yl)[1,1'-biphenyl]-4-yl]methyl]-benzenebutanamide 2. (R)-α-[(2-Amino-2-methyl-1-oxopropyl)amino]-N-[[2'-(1H-tetrazol-5-yl)[1,1'-biphenyl]-4-yl]-methyl]benzenebutanamide 3. (R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]benzenebutanamide 4. (R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]benzenebutanamide 5. (R)-α-[(3-Amino-3-methyl-1-oxobutyl)amino]-N-[[2'-(1H-tetrazol-5-yl)[1,1'-biphenyl]-4-yl]methyl]-benzenepentanamide 6. (R)-α-[(2-Amino-2-methyl-1-oxopropyl)amino]-N-[[2'-(1H-tetrazol-5-yl)[1,1'-biphenyl]-4-yl]-methyl]benzenepentanamide 7. (R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]benzenepentanamide 8. (R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]benzenepentanamide 9. (R)-α-[(3-Amino-3-methyl-1-oxobutyl)amino]-N-[[2'-(1H-tetrazol-5-yl)[1,1'-biphenyl]-4-yl]methyl]-1H-indole-3-propanamide 10. (R)-α-[(2-Amino-2-methyl-1-oxopropyl)amino]-N-[[2'-(1H-tetrazol-5-yl)[1,1'-biphenyl]-4-yl]-methyl]-1H-indole-3-propanamide 11. (R)-α-[[3-[2(R)-Hydroxypropyl]amino-3-methyl-1-oxobutyl]amino]-N-[[2'-(1H-tetrazol-5-yl)[1,1'-biphenyl ]-4-yl]methyl]-1H-indole-3-propanamide 12. (R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]-1H-indole-3-propanamide 13. (R)-α-[(3-Amino-3-methyl-1-oxobutyl)amino]-N-[[2'-(1H-tetrazol-5-yl)[1,1'-biphenyl]-4-yl]methyl]-3-[(phenylmethyl)oxy]propanamide 14. (R)-α-[(2-Amino-2-methyl-1-oxopropyl)amino]-N-[[2'-(1H-tetrazol-5-yl)[1,1'-biphenyl]-4-yl]methyl]-3-[(phenylmethyl)oxy]propanamide 15. (R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]-3-[(phenylmethyl)oxy]-propanamide 16. (R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]-3-[(phenylmethyl)oxy]-propanamide 17. (R)-α-[(3-Amino-3-methyl-1-oxobutyl)amino]-N-[[2'-(1H-tetrazol-5-yl)[1, 1'-biphenyl]-4-yl]-methyl]-3-[[(2,6-difluorophenyl)methyl]oxy]-propanamide 18. (R)-α-[(2-Amino-2-methyl-1-oxopropyl)amino]-N-[[2'-(1H-tetrazol-5-yl)[1,1'-biphenyl]-4-yl]-methyl]-3-[[(2,6-difluorophenyl)methyl]oxy]-propanamide 19. (R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]-3-[[(2,6-difluorophenyl)-methyl]oxy]propanamide 20. (R)-α-[[3-[2(S),3-Dihydroxypropyl]amino-3-methyl-1-oxobutyl]amino]-N-[[2'-(1H-tetrazol-5-yl)[1,1'- biphenyl]-4-yl]methyl]-3-[[(2,6-difluorophenyl)-methyl]oxy]propanamide 21. (R)-4'-[[[2-[(3-Amino-3-methyl-1-oxobutyl)amino]-1-oxo-4-phenylbutyl]amino]methyl]-N-ethyl[1,1'-biphenyl]-2-carboxamide 22. (R)-4'-[[[2-[(2-Amino-2-methyl-1-oxopropyl)-amino]-1-oxo-4-phenylbutyl]amino]methyl]-N-ethyl[1,1'-biphenyl]-2-carboxamide 23. (R)-4'-[[[2-[[3-[2(R)-Hydroxypropyl]amino-3-methyl-1-oxobutyl]amino]-1-oxo-4-phenylbutyl]-amino]methyl]-N-ethyl[1,1'-biphenyl]-2-carboxamide 24. (R)-4'-[[[2-[[3-[2(S),3-Dihydroxypropyl]amino-3-methyl-1-oxobutyl]amino]-1-oxo-4-phenylbutyl]-amino]methyl]-N-ethyl[1,1'-biphenyl]-2-carboxamide 25. (R)-4'-[[[2-[(3-Amino-3-methyl-1-oxobutyl)amino]-1-oxo-5-phenylpentyl]amino]methyl]-N-ethyl [1,1'-biphenyl]-2-carboxamide 26. (R)-4'-[[[2-[(2-Amino-2-methyl-1-oxopropyl)-amino]-1-oxo-5-phenylpentyl]amino]methyl]-N-ethyl[1,1'-biphenyl]-2-carboxamide 27. (R)-4'-[[[2-[[3-[2(R)-Hydroxypropyl]amino-3-methyl-1-oxobutyl]amino]-1-oxo-5-phenylpentyl]-amino]methyl]-N-ethyl[1,1'-biphenyl]-2-carboxamide 28. (R)-4'-[[[2-[[3-[2(S),3-Dihydroxypropyl]amino-3-methyl-1-oxobutyl]amino]-1-oxo-5-phenylpentyl]-amino]methyl]-N-ethyl[1,1'-biphenyl]-2-carboxamide 29. (R)-4'-[[[2-[(3-Amino-3-methyl-1-oxobutyl)amino]-1-oxo-3-(1H-indole-3-yl)propyl]amino]methyl]-N-ethyl[1,1'-biphenyl]-2-carboxamide 30. (R)-4'-[[[2-[(2-Amino-2-methyl-1-oxopropyl)-amino]-1-oxo-3-(1H-indole-3-yl)propyl]amino]-methyl]-N-ethyl[1,1'-biphenyl]-2-carboxamide 31. (R)-4'-[[[2-[[3-[2(R)-Hydroxypropyl]amino-3-methyl-1-oxobutyl]amino]-1-oxo-3-(1H-indole-3-yl)propyl]amino]methyl]-N-ethyl[1,1'-biphenyl]-2-carboxamide 32. (R)-4'-[[[2-[[3-[2(S),3-Dihydroxypropyl]amino-3-methyl-1-oxobutyl]amino]-1-oxo-3-(1H-indole-3-yl)propyl]amino]methyl]-N-ethyl [1,1'-biphenyl]-2-carboxamide 33. (R)-4'-[[[2-[(3-Amino-3-methyl-1-oxobutyl)amino]-1-oxo-3-[(phenylmethyl)oxy]propyl]amino]methyl]-N-ethyl[1,1'-biphenyl]-2-carboxamide 34. (R)-4'-[[[2-[(2-Amino-2-methyl-1-oxopropyl)-amino]-1-oxo-3-[(phenylmethyl)oxy]propyl]amino]-methyl]-N-ethyl[1,1'-biphenyl]-2-carboxamide 35. (R)-4'-[[[2-[[3-[2(R)-Hydroxypropyl]amino-3-methyl-1-oxobutyl]amino]-1-oxo-3-[(phenylmethyl)-oxy]propyl]amino]methyl]-N-ethyl[1,1'-biphenyl]-2-carboxamide 36. (R)-4'-[[[2-[[3-[2(S),3-Dihydroxypropyl]amino-3-methyl-1-oxobutyl]amino]-1-oxo-3-[(phenylmethyl)-oxy]propyl]amino]methyl]-N-ethyl[1,1'-biphenyl]-2-carboxamide 37. (R)-4'-[[[2-[(3-Amino-3-methyl-1-oxobutyl)amino]-1-oxo-3-[[(2,6-difluorophenyl)methyl]oxy]propyl]-amino]methyl]-N-ethyl[1,1'-biphenyl]-2-carboxamide 38. (R)-4'-[[[2-[(2-Amino-2-methyl-1-oxopropyl)-amino]-1-oxo-3-[[(2,6-difluorophenyl)methyl]oxy]-propyl]amino]methyl]-N-ethyl[1,1'-biphenyl]-2-carboxamide 39. (R)-4'-[[[2-[[3-[2(R)-Hydroxypropyl]amino-3-methyl-1-oxobutyl]amino]-1-oxo-3-[[(2,6-difluoro-phenyl)methyl]oxy]propyl]amino]methyl]-N-ethyl-[1,1'-biphenyl]-2-carboxamide 40. (R)-4'-[[[2-[[3-[2(S),3-Dihydroxypropyl]amino-3-methyl-1-oxobutyl]amino]-1-oxo-3-[[(2,6-difluoro-phenyl)methyl]oxy]propyl]amino]methyl]-N-ethyl-[1,1'-biphenyl]-2-carboxamide 41. (R)-α-[(3-Amino-3-methyl-1-oxobutyl)amino]-N-[[2'-[[(methylamino)carbonyl]amino][1,1'-biphenyl]-4-yl]methyl]benzenebutanamide 42. (R)-α-[(2-Amino-2-methyl-1-oxopropyl)amino]-N-[[2'-[[(methylamino)carbonyl]amino][1,1'-biphenyl]-4-yl]methyl]benzenebutanamide 43. (R)-α-[[3-[2(R)-Hydroxypropyl]amino-3-methyl-1-oxobutyl]amino]-N-[[2'-[[(methylamino)carbonyl]amino][1,1'-biphenyl]-4-yl]methyl]benzenebutanamide 44. (R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]benzenebutanamide 45. (R)-α-[(3-Amino-3-methyl-1-oxobutyl)amino]-N-[[2'-[[(methylamino)carbonyl]amino][1,1'-biphenyl]-4-yl]methyl]benzenepentanamide 46. (R)-α-[(2-Amino-2-methyl-1-oxopropyl)amino]-N-[[2'-[[(methylamino)carbonyl]amino][1,1'-biphenyl]-4-yl]methyl]benzenepentanamide 47. (R)-α-[[3-[2(R)-Hydroxypropyl]amino-3-methyl-1-oxobutyl]amino]-N-[[2'-[[(methylamino)carbonyl]amino][1,1'-biphenyl]-4-yl]methyl]benzenepentanamide 48. (R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]benzenepentanamide 49. (R)-α-[(3-Amino-3-methyl-1-oxobutyl)amino]-N-[[2'-[[(methylamino)carbonyl]amino][1,1'-biphenyl]-4-yl]methyl]-1H-indole-3-propanamide 50. (R)-or-[(2-Amino-2-methyl-1-oxopropyl)amino]-N-[[2'-[[(methylamino)carbonyl]amino][1,1'-biphenyl]-4-yl]methyl]-1H-indole-3-propanamide 51. (R)-α-[[3-[2(R)-Hydroxypropyl]amino-3-methyl-1-oxobutyl]amino]-N-[[2'-[[(methyl amino) carbonyl]amino][1,1'-biphenyl]-4-yl]methyl]-1H-indole-3-propanamide 52. (R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]-1H-indole-3-propanamide 53. (R)-α-[(3-Amino-3-methyl-1-oxobutyl)amino]-N-[[2'-[[(methylamino)carbonyl]amino][1,1'-biphenyl]-4-yl]methyl]-3-[(phenylmethyl)oxy]-propanamide 54. (R)-α-[(2-Amino-2-methyl-1-oxopropyl)amino]-N-[[2'-[[(methylamino)carbonyl]amino][1,1'-biphenyl]-4-yl]methyl]-3-[(phenylmethyl)oxy]-propanamide 55. (R)-α-[[3-[2(R)-Hydroxypropyl]amino-3-methyl-1-oxobutyl]amino]-N-[[2'-[[(methylamino)carbonyl]-amino]-[1,1'-biphenyl]-4-yl]methyl]-3-[(phenyl-methyl)oxy]propanamide 56. (R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]-3-[(phenylmethyl)oxy]propanamide 57. (R)-α-[(3-Amino-3-methyl-1-oxobutyl)amino]-N-[[2'-[[(methylamino)carbonyl]amino][1,1'-biphenyl]-4-yl]methyl]-3-[[(2,6-difluorophenyl)-methyl]oxy]propanamide 58. (R)-α-[(2-Amino-2-methyl-1-oxopropyl)amino]-N-[ [2'-[[(methylamino)carbonyl]amino][1,1'-biphenyl]-4-yl]methyl]-3-[[(2,6-difluorophenyl)-methyl]oxy] propanamide 59. (R)-α-[[3-[2(R)-Hydroxypropyl]amino-3-methyl-1-oxobutyl]amino]-N-[[2'-[[(methylamino)carbonyl] amino][1,1'-biphenyl]-4-yl]methyl]-3-[[(2,6-difluorophenyl)methyl]oxy]propanamide 60. (R)-α-[[3-[2(S),3-Dihydroxypropyl]amino-3-methyl-1-oxobutyl]amino]-N-[[2'-[[(methylamino)carbonyl]-amino][1,1'-biphenyl]-4-yl]methyl]-3-[[(2,6-difluorophenyl)methyl]oxy]propanamide 61. (R)-α-[(3-Amino-3-methyl-1-oxobutyl)amino]-N-[ [2'-hydroxymethyl[1,1'-biphenyl]-4-yl]methyl]-benzenebutanamide 62. (R)-α-[(2-Amino-2-methyl-1-oxopropyl)amino]-N-[ [2'-hydroxymethyl[1,1'-biphenyl]4-yl]methyl]-benzenebutanamide 63. (R)-α-[[3-[2(R)-Hydroxypropyl]amino-3-methyl-1-oxobutyl]amino]-N-[[2'-hydroxymethyl[1,1'-biphenyl]-4-yl]methyl]benzenebutanamide 64. (R)-α-[[3-[2(S),3-Dihydroxypropyl]amino-3-methyl-1-oxobutyl]amino]-N-[[2'-hydroxymethyl[1,1'-biphenyl]-4-yl]methyl]benzenebutanamide 65. (R)-α-[(3-Amino-3-methyl-1-oxobutyl)amino]-N-[ [2'-hydroxymethyl[1,1'-biphenyl]-4-yl]methyl]-benzenepentanamide 66. (R)-α-[(2-Amino-2-methyl-1-oxopropyl)amino]-N-[ [2'-hydroxymethyl[1,1'-biphenyl]-4-yl]methyl]-benzenepentanamide 67. (R)-α-[[3-[2(R)-Hydroxypropyl]amino-3-methyl-1-oxobutyl]amino]-N-[[2'-hydroxymethyl[1,1'-biphenyl]-4-yl]methyl]benzenepentanamide 68. (R)-α-[[3-[2(S),3-Dihydroxypropyl]amino-3-methyl-1-oxobutyl]amino]-N-[[2'-hydroxymethyl[1,1'-biphenyl]-4-yl]methyl]benzenepentanamide 69. (R)-α-[(3-Amino-3-methyl-1-oxobutyl)amino]-N-[ [2'-hydroxymethyl[1,1'-biphenyl]-4-yl]methyl]-1H-indole-3-propanamide 70. (R)-α-[(2-Amino-2-methyl-1-oxopropyl)amino]-N-[ [2'-hydroxymethyl[1,1'-biphenyl]-4-yl]methyl]-1H-indole-3-propanamide 71. (R)-α-[[3-[2(R)-Hydroxypropyl]amino-3-methyl-1-oxobutyl]amino]-N-[[2'-hydroxymethyl[1,1'-biphenyl]-4-yl]methyl]-1H-indole-3-propanamide 72. (R)-α-[[3-[2(S),3-Dihydroxypropyl]amino-3-methyl-1-oxobutyl]amino]-N-[[2'-hydroxymethyl[1,1'-biphenyl]-4-yl]methyl]-1H-indole-3-propanamide 73. (R)-α-[(3-Amino-3-methyl-1-oxobutyl)amino]-N-[ [2'-hydroxymethyl[1,1'-biphenyl]-4-yl]methyl]-3-[ (phenylmethyl)oxy]propanamide 74. (R)-α-[(2-Amino-2-methyl-1-oxopropyl)amino]-N-[ [2'-hydroxymethyl[1,1'-biphenyl]-4-yl]methyl]-3-[ (phenylmethyl)oxy]propanamide 75. (R)-α-[[3-[2(R)-Hydroxypropyl]amino-3-methyl-1-oxobutyl]amino]-N-[[2'-hydroxymethyl[1,1'-biphenyl]-4-yl]methyl]-3-[(phenylmethyl)oxy]propanamide 76. (R)-α-[[3-[2(S),3-Dihydroxypropyl]amino-3-methyl-1-oxobutyl]amino]-N-[[2'-hydroxymethyl[1,1'-biphenyl]-4-yl]methyl]-3-[(phenylmethyl)oxy] propanamide 77. (R)-α-[(3-Amino-3-methyl-1-oxobutyl)amino]-N-[ [2'-hydroxymethyl[1,1'-biphenyl]-4-yl ]methyl]-3-[[(2, 6-difluorophenyl)methyl]oxy]propanamide 78. (R)-α-[(2-Amino-2-methyl-1-oxopropyl)amino]-N-[ [2'-hydroxymethyl[1,1'-biphenyl]-4-yl ]methyl ]-3-[[ (2,6-difluorophenyl)methyl]oxy]propanamide 79. (R)-α-[[3-[2(R)-Hydroxypropyl]amino-3-methyl-1-oxobutyl]amino]-N-[[2'-hydroxymethyl[1,1'-biphenyl]-4-yl]methyl]-3-[[(2,6-difluorophenyl)-methyl]oxy] propanamide 80. (R)-α-[[3-[2(S),3-Dihydroxypropyl]amino-3-methyl-1-oxobutyl]amino]-N-[[2'-hydroxymethyl[1,1'-biphenyl]-4-yl]methyl]-3-[[(2,6-difluorophenyl)-methyl]oxy]propanamide 81. (R)-α-[(3-Amino-3-methyl-1-oxobutyl)amino]-N-[ [2'-[[[(methylamino)carbonyl]amino]methyl]-[1,1'-biphenyl]-4-yl]methyl]benzenebutanamide 82. (R)-α-[(2-Amino-2-methyl-1-oxopropyl)amino]-N-[ [2'-[[[(methylamino)carbonyl]amino]methyl]-[1,1'-biphenyl]-4-yl]methyl]benzenebutanamide 83. (R)-α-[[3-[2(R)-Hydroxypropyl]amino-3-methyl-1-oxobutyl]amino]-N-[[2'-[[[(methylamino)carbonyl] amino]methyl][1,1'-biphenyl]-4-yl]methyl] benzenebutanamide 84. (R)-α-[[3-[2(S),3-Dihydroxypropyl]amino-3-methyl-1-oxobutyl]amino]-N-[[2'-[[[(methylamino)carbon-yl]amino]methyl][1,1'-biphenyl]-4-yl]methyl]-benzenebutanamide 85. (R)-α-[(3-Amino-3-methyl-1-oxobutyl)amino]-N-[ [2'-[[[(methylamino)carbonyl]amino]methyl]-[1,1'-biphenyl]-4-yl]methyl]benzenepentanamide 86. (R)-α-[(2-Amino-2-methyl-1-oxopropyl)amino]-N-[ [2'-[[[(methylamino)carbonyl]amino]methyl]-[1,1'-biphenyl]-4-yl]methyl]benzenepentanamide 87. (R)-α-[[3-[2(R)-Hydroxypropyl]amino-3-methyl-1-oxobutyl]amino]-N-[[2'-[[[(methylamino)carbonyl] amino]methyl][1,1'-biphenyl]-4-yl]methyl] benzenepentanamide 88. (R)-α-[[3-[2(S),3-Dihydroxypropyl]amino-3-methyl-1-oxobutyl]amino]-N-[[2'-[[[(methylamino)carbonyl] amino]methyl][1,1'-biphenyl]-4-yl]methyl] benzenepentanamide 89. (R)-α-[(3-Amino-3-methyl-1-oxobutyl)amino]-N-[ [2'-[[[(methylamino)carbonyl]amino]methyl]-[1,1'-biphenyl]-4-yl]methyl]-1H-indole -3-propanamide 90. (R)-α-[(2-Amino-2-methyl-1-oxopropyl)amino]-N-[ [2'-[[[(methylamino)carbonyl]amino]methyl]-[1,1'-biphenyl]-4-yl]methyl]-1H-indole-3-propanamide 91. (R)-α-[[3-[2(R)-Hydroxypropyl]amino-3-methyl-1-oxobutyl]amino]-N-[[2'-[[[(methylamino)carbonyl] amino]methyl][1,1'-biphenyl]-4-yl]methyl]-1H-indole-3-propanamide 92. (R)-α-[[3-[2(S),3-Dihydroxypropyl]amino-3-methyl-1-oxobutyl]amino]-N-[[2'-[[[(methylamino)carbon-yl] amino]methyl][1,1'-biphenyl]-4-yl]methyl]-1H-indole-3-propanamide 93. (R)-α-[(3-Amino-3-methyl-1-oxobutyl)amino]-N-[ [2'-[[[(methylamino)carbonyl]amino]methyl]-[1,1'-biphenyl]-4-yl]methyl]-3-[(phenylmethyl)-oxy] propanamide 94. (R)-α-[(2-Amino-2-methyl-1-oxopropyl)amino]-N-[ [2'-[[[(methylamino)carbonyl]amino]methyl]-[1,1'-biphenyl]-4-yl]methyl]-3-[(phenylmethyl)-oxy] propanamide 95. (R)-α-[[3-[2(R)-Hydroxypropyl]amino-3-methyl-1-oxobutyl]amino]-N-[[2'-[[[(methylamino)carbonyl] amino]methyl][1,1'-biphenyl]-4-yl]methyl]-3-[ (phenylmethyl)oxy]propanamide 96. (R)-α-[[3-[2(S),3-Dihydroxypropyl]amino-3-methyl-1-oxobutyl]amino]-N-[[2'-[[[(methylamino)carbon-yl]amino]methyl][1,1'-biphenyl]-4-yl]methyl]-3-[(phenylmethyl)oxy]propanamide
97. (R)-α-[(3-Amino-3-methyl-1-oxobutyl)amino]-N-[[2'-[[[(methylamino)carbonyl]amino]methyl]-[1,1'-biphenyl]-4-yl]methyl]-3-[[(2,6-difluoro-phenyl)methyl]oxy]propanamide
98. (R)-α-[(2-Amino-2-methyl-1-oxopropyl)amino]-N-[[2'-[[[(methylamino)carbonyl]amino]methyl]-[1,1'-biphenyl]-4-yl]methyl]-3-[[(2,6-difluoro-phenyl)methyl]oxy]propanamide
99. (R)-α-[[3-[2(R)-Hydroxypropyl]amino-3-methyl-1-oxobutyl]amino]-N-[[2'-[[[(methylamino)carbonyl]amino]methyl][1,1'-biphenyl]-4-yl]methyl]-3-[[(2,6-difluorophenyl)methyl]oxy]propanamide
100. (R)-α-[[3-[2(S),3-Dihydroxypropyl]amino-3-methyl-1-oxobutyl]amino]-N-[[2'-[[[(methylamino)carbonyl]amino]methyl][1,1'-biphenyl]-4-yl]methyl]-3-[[(2,6-difluorophenyl)methyl]oxy]propanamide
101. (R)-α-[(3-Amino-3-methyl-1-oxobutyl)amino]-N-[[2'-(1H-tetrazol-5-yl)[1,1'-biphenyl]-4-yl]methyl]benzenepropanamide
102. (R)-α-[(2-Amino-2-methyl-1-oxypropyl)amino]-N-methyl-N-[[2'-(1H-tetrazol-5-yl)-[1,1'-biphenyl]-4-yl]methyl]benzenebutanamide
103. (R)-α-[(2-amino-2-methyl-1-oxypropyl)amino]-N-[[2'-cyano-[1,1'-biphenyl]-4-yl]methyl]-N-methylbenzenebutanamide
104. (R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]benzenebutanamide
105. (R)-α-[(3-Amino-3-methyl-1-oxybutyl)amino]-N-methyl-N-[[(2'-[([methylamino]carbonyl)aminomethyl])-[1,1'-biphenyl]-4-yl]methyl]benzenebutanamide
106. (R)-α-[(4-Amino-4-methyl-1-oxopentyl)amino]-N-methyl-N-[[2'-(1H-tetrazol-5-yl)[1,1'-biphenyl]-4-yl]methyl]benzenebutanamide
107. (R)-α-[(4-Amino-4-methyl-1-oxypentyl)amino]-N-methyl-N-[[(2'-[[[(methylamino)carbonyl]amino]methyl]-[1,1'-biphenyl]-4-yl]-methyl]benzenebutanamide
108. (R)-α-[(2-Amino-2-methyl-1-oxopropyl)amino]-N-methyl-N-[[2'-(1H-tetrazol-5-yl)[1,1'-biphenyl]-4-yl]methyl]-1H-indole-3-propanamide
109. (R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]-1H-indole-3-propanamide
110. (R)-α-[(2-Amino-2-methyl-1-oxypropyl)amino]-N-ethyl-N-[[(2'-[((methylamino)carbonyl)aminomethyl])-[1,1'-biphenyl]-4-yl]methyl]benzenebutanamide
111. (R)-α-[(3-Amino-3-methyl-1-oxybutyl)amino]-N-ethyl-N-[[(2'-[[[(methylamino)carbonyl]amino]methyl]-[1,1-biphenyl]-4-yl]methyl]benzenebutanamide
112. (R)-α-[(2-Amino-2-methyl-1-oxypropyl)amino]-N-[[2'-(1H-tetrazol-5-yl)-[1,1'-biphenyl]-4-yl]methyl]-N-(propyl)benzenebutanamide
113. (R)-α-[(2-Amino-2-methyl-1-oxopropyl)amino]-N-[(2'-[(2-hydroxyethylamino)carbonyl]amino][1,1'-biphenyl]-4-yl]-methyl]-3-[(phenylmethyl)oxy]propanamide
114. (R)-α-[(2-Amino-2-methyl)-1-oxopropyl]amino-N-methyl-N-[(2'-[[(methylamino)carbonyl]amino)methyl][1,1'-biphenyl]-4-yl]-benzenebutanamide
115. (R)-α-[(2-Amino-2-methyl)-1-oxopropyl]amino-N-methyl-N-[2'-(1H-tetrazol-5-yl)[1,1'-biphenyl]-4-yl] butanamide Representative examples of the nomenclature employed are given below:

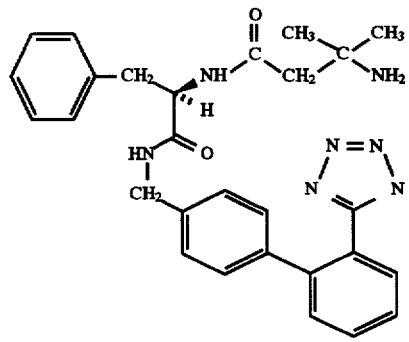

(R)-α-[(3-Amino-3-methyl-1-oxobutyl)amino]-N-[[2'-(1H-tetrazol-5-yl)[1,1'-biphenyl]-4-yl]methyl]benzenepropanamide

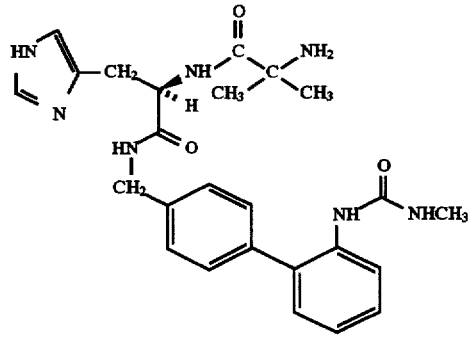

(R)-α-[(2-Amino-2-methyl-1-oxopropyl)amino]-N-[[2'-[[(methylamino)carbonyl]amino][1,1'-biphenyl]-4-yl]-methyl]-1H-imidazole-4-yl-propanamide

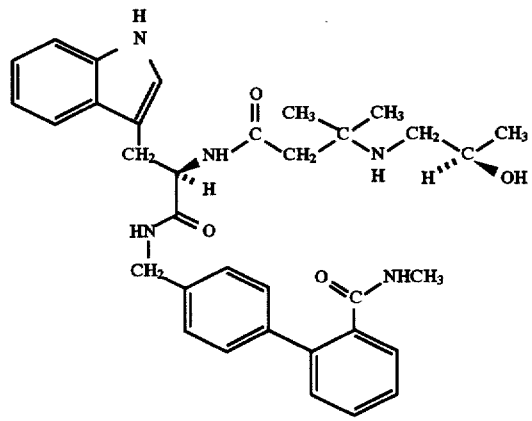

(R)-4'-[[[2-[[3-[2(R)-Hydroxypropyl]amino-3-methyl-1-oxobutyl]-amino]-1-oxo-3-(1H-indole-3-yl)propyl]amino]-methyl]-N-methyl[1,1'-biphenyl]-2-carboxamide

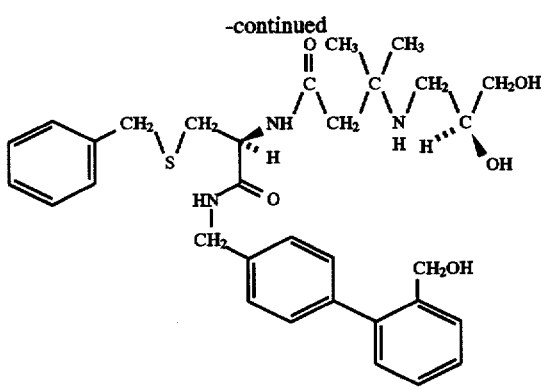

(S)-α-[[3-[2(S),3-Dihydroxypropyl]amino-3-methyl-1-oxobutyl]amino]-
N-[[2'-hydroxymethyl[1,1'-biphenyl]-4-yl]methyl]-3-[(phenylmethyl)-
thiolpropanamide The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. This center will be designated according to the R/S rules as either R or S depending upon the values of X, n, p and $R^{15}$.

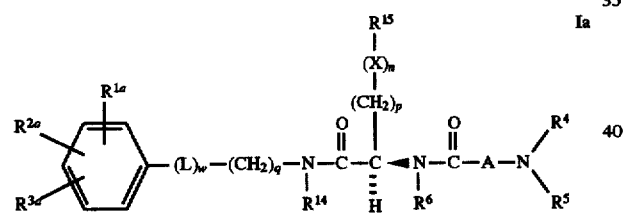

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

Compounds I of the present invention are prepared from amino acid intermediates II as described in the following reaction schemes.

Amino acid intermediates 1 are, in some cases, commercially available in the form of their N-t-butoxycarbonyl or N-benzyloxycarbonyl derivatives. These intermediates can also be prepared by a variety of methods described in the literature and familiar to one skilled in the art. For example, the Strecker synthesis may be employed for the construction of racemic amino acid intermediates. Resolution can be achieved by classical methods, for example separation of diastereomeric salts by fractional crystallization. Alternatively, a chiral amino acid synthesis may be employed using the procedures described by R. M. Williams and M. N. Im (J. Amer. Chem. Soc., 113, 9276–9286, 1991.). Conversion of the free amino acid product to its N-t-butoxycarbonyl (BOC) derivative can be achieved by a number of methods known in the art, for example, treatment with di-t-butyl dicarbonate in an inert solvent such as methylene chloride. Benzyloxycarbonyl (CBz) protected derivatives are obtained by treatment of the amino acid with, for example, benzyl chloroformate.

SCHEME 1

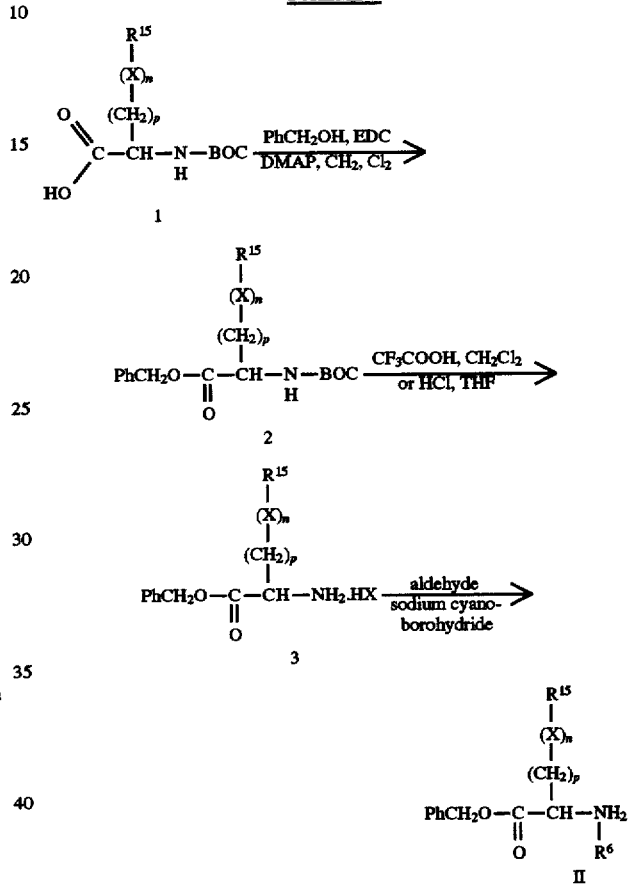

As shown in Scheme 1, formation of the benzyl ester 2 is carried out by treatment with benzyl alcohol in the presence of a coupling agent, such as 1-(3-dimethylaminopropyl)-3-ethylcarbodiimide hydrochloride (EDC), in methylene chloride with a catalytic amount of 4-dimethylaminopyridine. Removal of the BOC protecting group through the use of trifluoroacetic acid in methylene chloride or hydrochloric acid in tetrahydrofuran gives the amine salt 3. Reductive alkylation with an aldehyde and a mild reducing agent, such as sodium cyanoborohydride, leads to the desired intermediate II.

Attachment of the amino acid sidechain to intermediates of formula II is accomplished by the route shown in Scheme 2. Coupling is conveniently carded out by the use of an appropriately protected amino acid derivative, such as that illustrated by formula III, and a coupling reagent such as benzotriazol-1-yloxytris(dimethylamino)phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978)) or by medium pressure liquid chromatography. Removal of the benzyl ester by hydrogenolysis or by saponification in the presence of a strong base, such as sodium hydroxide, affords the product IV. It may be appreciated by one skilled in the art that the protecting group G must be selected to be compatible with the conditions employed for removal of the specific class of ester present in 4. Hence, as illustrated for the benzyl ester 4, G is taken as t-butoxycarbonyl. It may further be appreciated that other combinations of protecting group G and ester functionality may be employed; for example, the benzyloxycarbonyl protecting group is inert to the standard conditions of aqueous sodium hydroxide employed to hydrolyze methyl or ethyl esters.

Reaction of isobutylene with N-chlorosulfonyl-isocyanate 5 in diethyl ether gives the azetidinone derivative 6. Removal of the chlorosulfonyl group with aqueous sodium sulfite followed by reaction with di-t-butyl-dicarbonate gives the BOC-protected intermediate 8. Alkaline hydrolysis gives the protected amino acid derivative 9 in good overall yield.

Attachment of the substituted phenyl sidechain V is achieved as shown in Scheme 4. Using the aforementioned BOP reagent, coupling is conveniently carried out in an inert solvent, such as methylene chloride, to give compounds of formula VII in protected form.

SCHEME 2

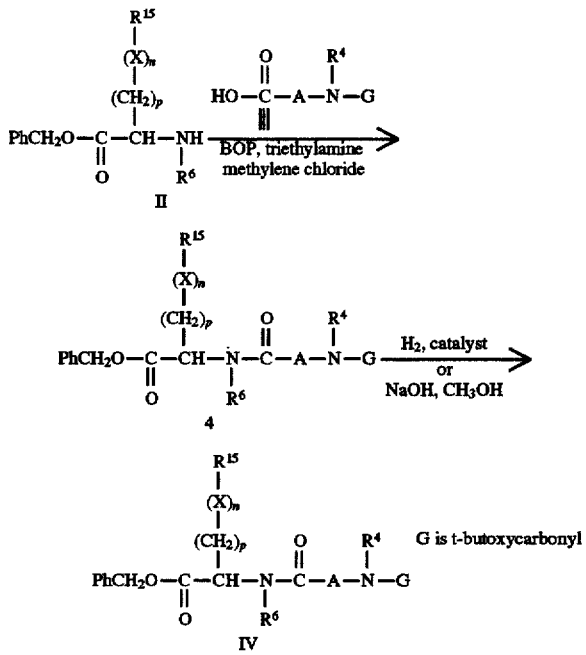

The protected amino acid derivatives III are, in many cases, commercially available in t-butoxycarbonyl (BOC) or benzyloxycarbonyl (CBz) forms. A useful method to prepare the preferred sidechain 9 is shown in Scheme 3.

SCHEME 3

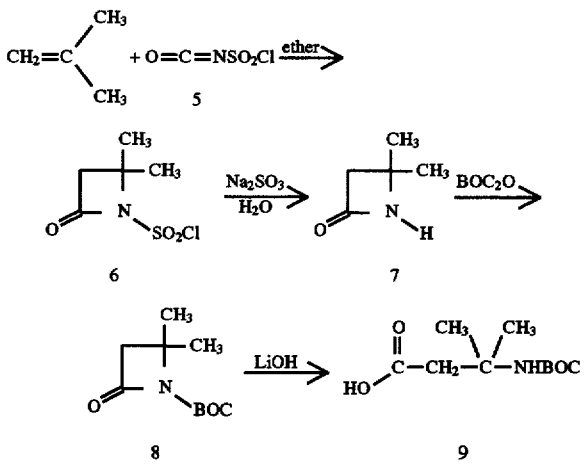

SCHEME 4

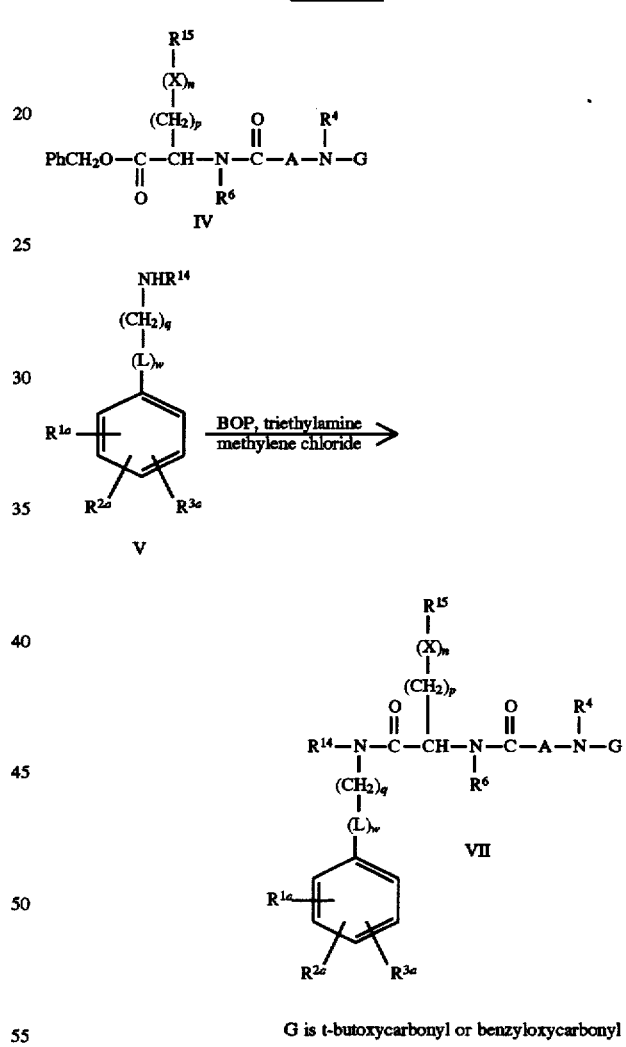

G is t-butoxycarbonyl or benzyloxycarbonyl

The substituted phenyl sidechains V are prepared from the corresponding alkylating agent VI by displacement of the leaving group Y with sodium azide as shown in Scheme 5. Reduction of the azide product by hydrogenation in the presence of a transition metal catalyst, or alternatively by reaction with triphenylphosphine followed by hydrolysis, gives the desired amine derivative 10. Conversion to the desired intermediate V is achieved by the aforementioned reductive alkylation procedure.

SCHEME 5

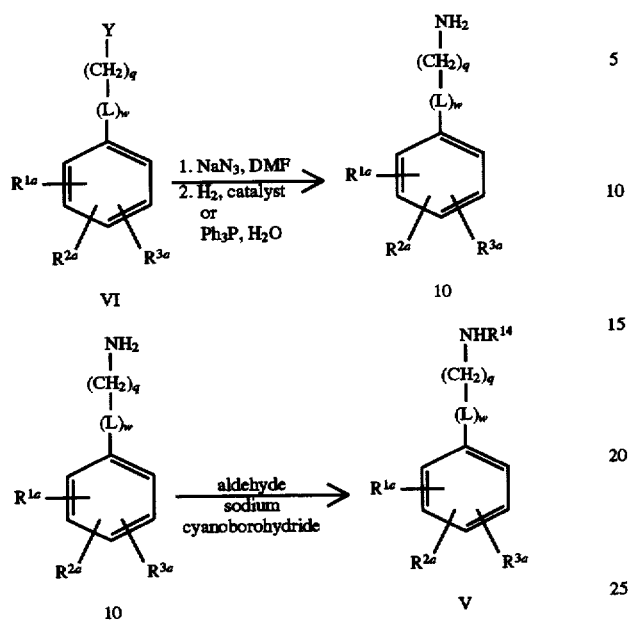

Y is a leaving group

As illustratrated in Scheme 6 an alternative route involves coupling of intermediate IV with $R^{14}NH_2$ using one of the coupling reagents described previously, followed by alkylation of the amide bond with VI. Alkylation is carried out in an inert solvent, such as dimethylformamide, using a strong base such as sodium hydride or potassium t-butoxide at temperatures of 0°–100° C. Alkylating agents VI are, in some cases, commercially available or may be prepared by the procedures described in the following schemes.

SCHEME 6

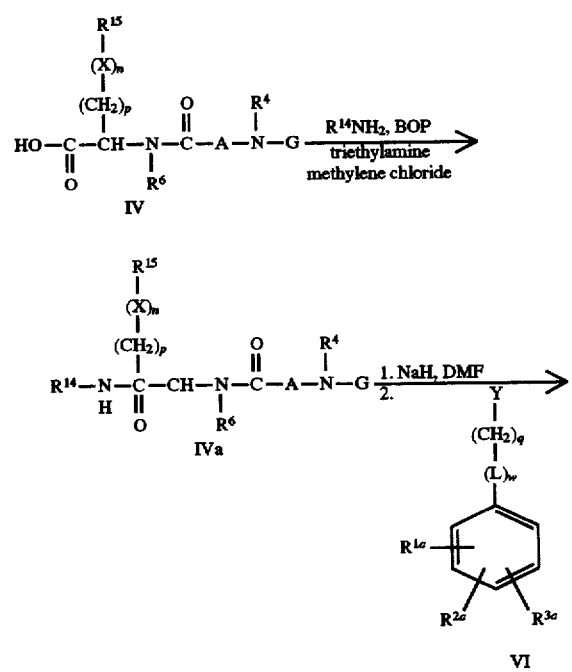

SCHEME 6 -continued

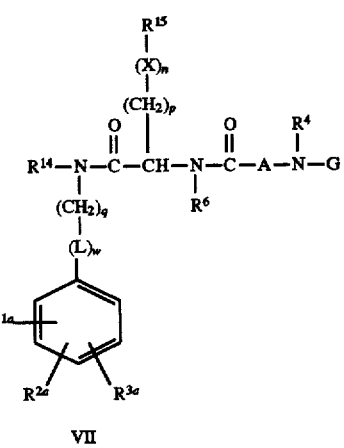

G is t-butoxycarbonyl or benzyloxycarbonyl

Alkylating agents VI are, in some cases commercially available compounds or may be prepared by methods described in the literature and familiar to one skilled in the art.

Compounds of formula I wherein $R^{3a}$ or $R^{3b}$ is a tetrazole (13) are prepared as described in Scheme 7 by reaction of IV with a suitably substituted intermediate 11 containing a nitrile as tetrazole precursor. Elaboration to the desired product 13 is carried out by treatment with trimethyltin azide in boiling toluene.

SCHEME 7

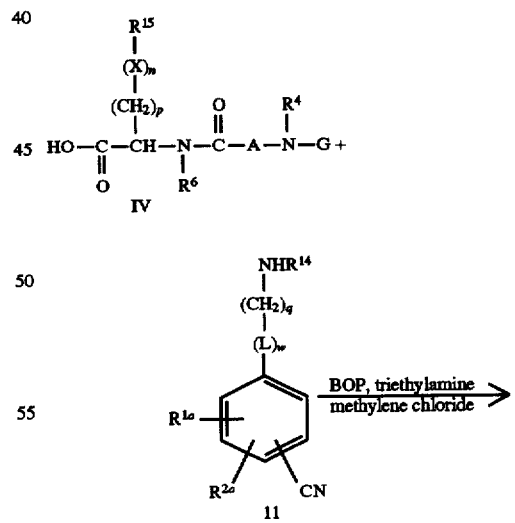

SCHEME 7 -continued
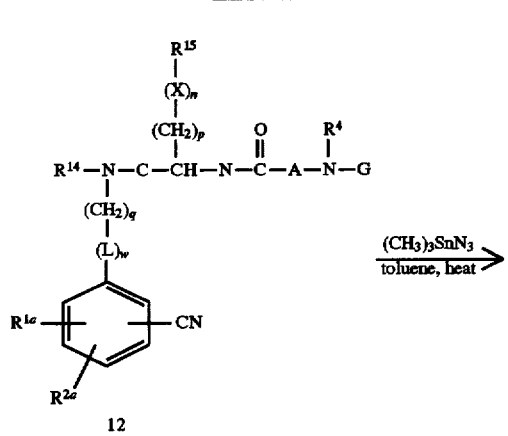
12
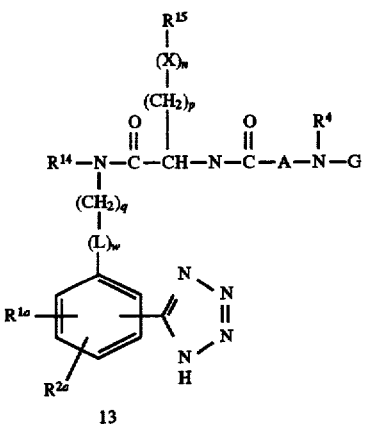
13
G = t-butoxycarbonyl or benzyloxycarbonyl
A useful method to prepare the preferred intermediate 18 is shown in Scheme 8, and in U.S. Pat. No. 5,039,814.
SCHEME 8
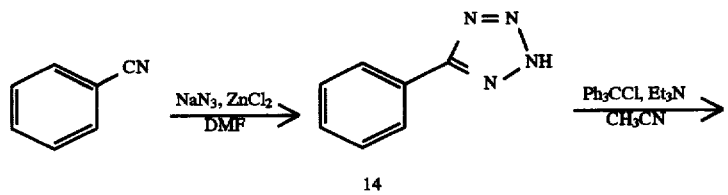
14
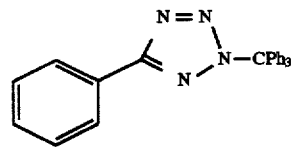
15
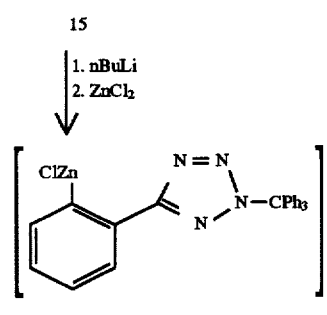
16
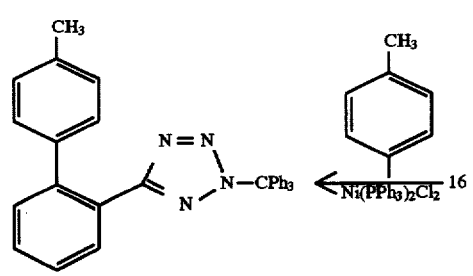
17

-continued
SCHEME 8

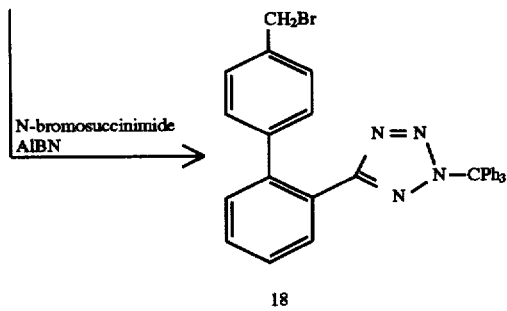

18

As outlined in Scheme 8, benzonitrile is treated with sodium azide and zinc chloride to give 5-phenyltetrazole 14 which is converted to the N-trityl derivative 15 by treatment with triphenylmethyl chloride and triethylamine. The zinc reagent 16 was prepared by treatment with n-butyl lithium followed by zinc chloride. Coupling with 4-iodotoluene using the catalyst bis(triphenylphosphine)nickel(II) dichloride gives the biphenyl product 17 in high yield. Reaction with N-bromosuccinimide and AIBN gives bromide 18. Conversion to the requisite amine derivative V is achieved by the procedure described in Scheme 5.

Compounds of Formula I wherein $R^{3a}$ or $R^{3b}$ are taken as $R^4R^5NCO$ can be prepared by several methods. For example, as shown in Scheme 9, compound 20 wherein $R^4$ and $R^5$ are both hydrogen is conveniently prepared by hydrolysis of a nitrile precursor 19.

SCHEME 9

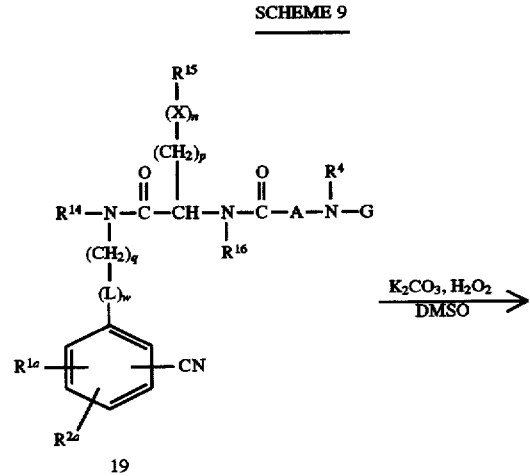

19

-continued
SCHEME 9

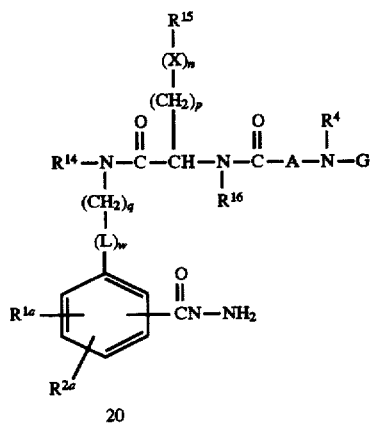

20

Thus, treatment of the nitrile 19 with hydrogen peroxide and a strong base, such as potassium carbonate, in a polar solvent, such as dimethylsulfoxide at temperatures of 25° C. to 150° C. results in formation of the amide derivative 20.

A useful method of preparing the intermediate 23 is outlined in Scheme 10.

SCHEME 10

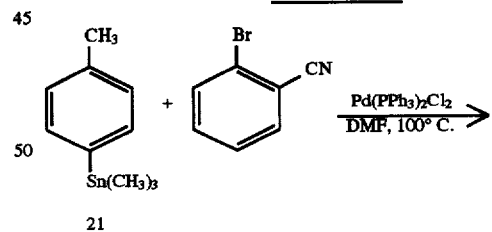

21

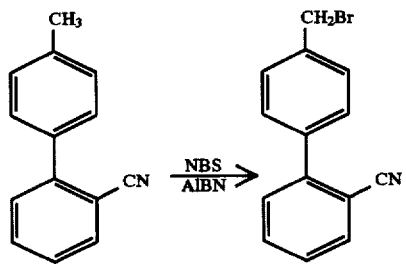

22     23

Thus, treatment of 4-(methylphenyl)trimethyl stannane 21 with 2-bromobenzonitrile in dimethylformamide at 100° C. in the presence of bis-triphenylphosphine palladium (II) chloride results in coupling to form the biphenyl nitrile 22 in high yield. Conversion to bromide 23 is achieved by treatment with N-bromosuccinimide and a radical initiator, such as azobisisobutyronitrile (AIBN), in refluxing carbon tetrachloride. Conversion to the requisite amine derivative V is achieved by the procedure described in Scheme 5.

Compounds of Formula I wherein $R^{3a}$ or $R^{3b}$ are taken as $R^4R^5NCO$ and $R^4$ and/or $R^5$ are other than hydrogen are prepared from the corresponding carboxylic acid derivatives 24 as shown in Scheme 11.

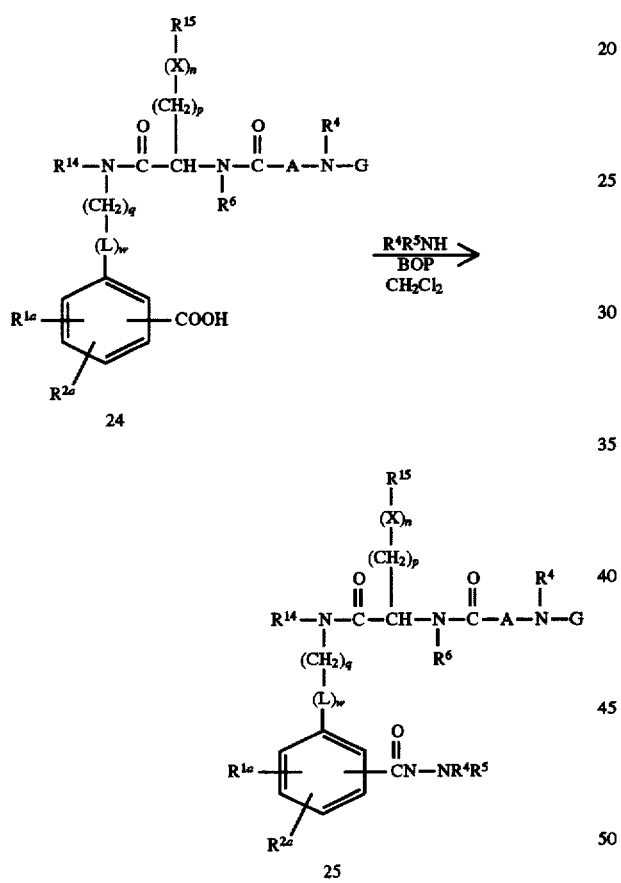

Coupling of the carboxylic acid derivative 24 with $R^4R^5NH$ is conveniently carried out by the use of a coupling reagent such as benzotriazol-1-yloxytris-(dimethylamino) phosphonium hexafluorophosphate ("BOP") in an inert solvent such as methylene chloride.

The requisite carboxylic acid precursors can be prepared as illustrated in Scheme 12 for the biphenyl compound 24.

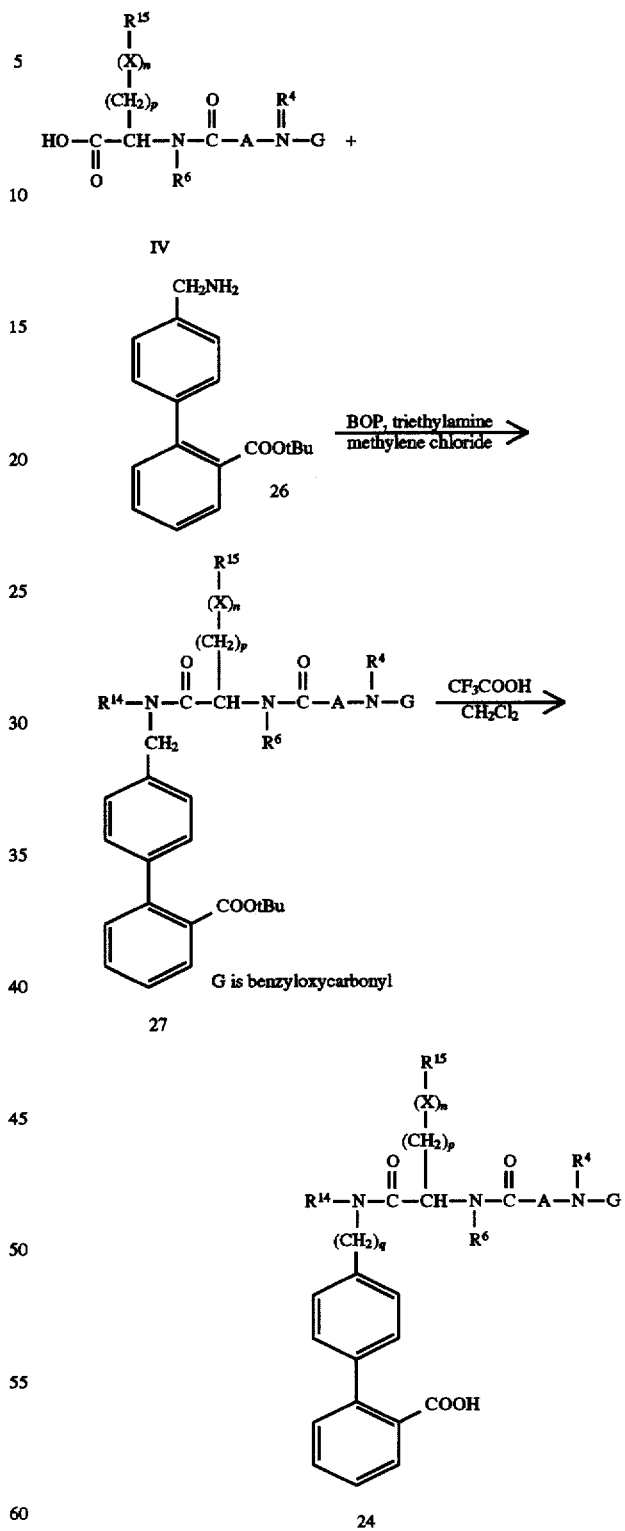

A convenient method to prepare the useful intermediate 30 is shown in Scheme 13. Metallation of 4-iodotoluene with t-butyllithium in tetrahydro-furan, followed by treatment with zinc chloride gives the intermediate zinc reagent 28. Coupling of 28 with t-butyl 2-bromobenzoate in the presence of bis(triphenylphosphine)nickel(II) chloride affords the biphenyl product 29 in high yield. Bromination to give the desired intermediate 30 is carried out under the aforementioned conditions. Conversion to the requisite amine derivative V is achieved by the procedure described in Scheme 5.

SCHEME 13

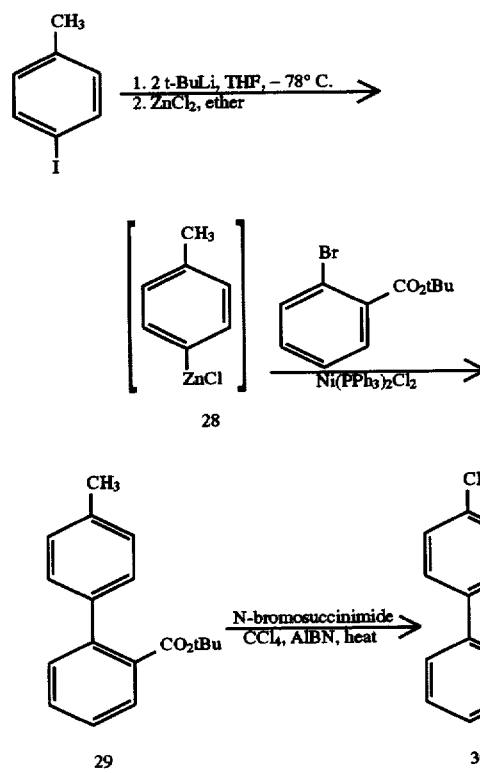

Compounds of formula I where $R^{3a}$ or $R^{3b}$ is a carbamate, semicarbazide or urea derivative, wherein this functionality is attached to the phenyl ring by a nitrogen atom are prepared from intermediate 32, obtained by reaction with a derivative 31 wherein $R^{3a}$ or $R^{3b}$ is a nitro group as shown in Scheme 14.

SCHEME 14

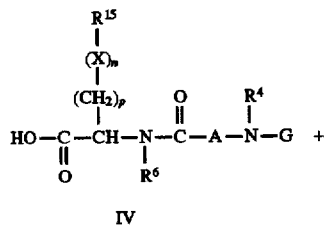

IV

-continued
SCHEME 14

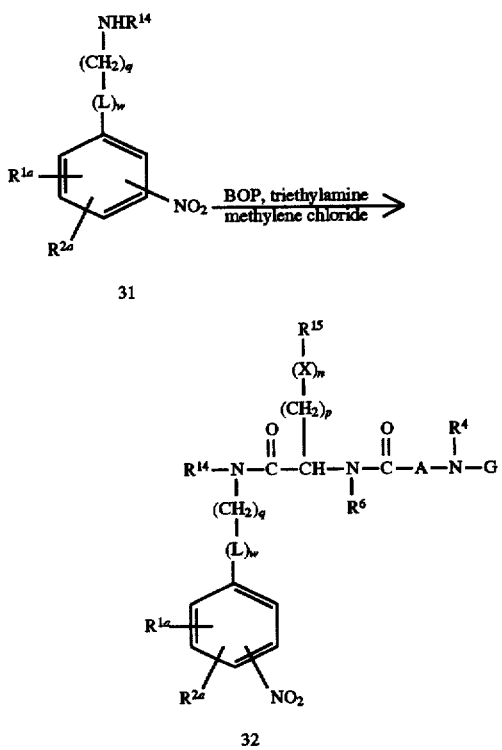

G is t-butoxycarbonyl

A useful method of synthesizing a preferred intermediate 36 is shown in reaction Scheme 15.

SCHEME 15

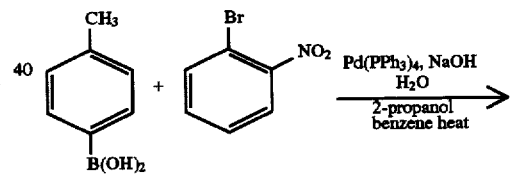

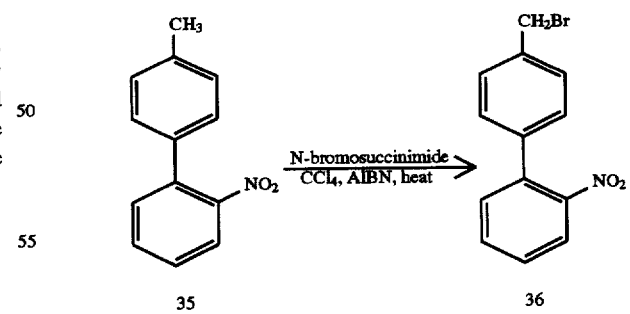

Reaction of 4-tolylboronic acid 33 with 2-bromonitrobenzene 34 in the presence of a transition metal catalyst such as (tetrakis)triphenylphosphine palladium (0) in a mixed solvent system containing aqueous sodium hydroxide, water, 2-propanol and benzene at elevated temperatures for several hours gives the coupled product 3.5 in good overall yield. Chromatographic purification and separation of unwanted by-products is conveniently performed on silica, eluting with common organic solvents such as hexane, ethyl acetate and methylene chloride. Conversion of 35 to the bromide derivative 36 is accomplished by treatment with N-bromosuccinimide in refluxing carbon tetrachloride in the presence of a radical initiator such as benzoyl peroxide or 2,2-azobisisobutyronitrile (AIBN). Conversion to the requisite amine derivative V is acheived by the procedure described in Scheme 5.

As shown in Scheme 16, reduction of the nitro group of 32 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 32 must be compatible with the experimental conditions anticipated for reduction. For example, intermediate 32 wherein G is t-butoxycarbonyl (BOC) are stable to the conditions of catalytic reduction employed in the conversion to 37. Intermediate 37 may also be further elaborated to new intermediate 38 by reductive alkylation with an aldehyde by the aforementioned procedures.

SCHEME 16

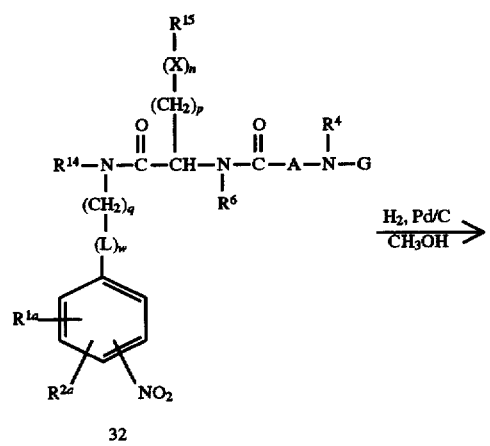

32

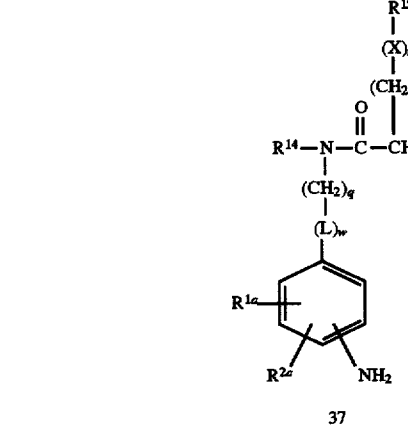

37

G is t-butoxycarbonyl

-continued
SCHEME 16

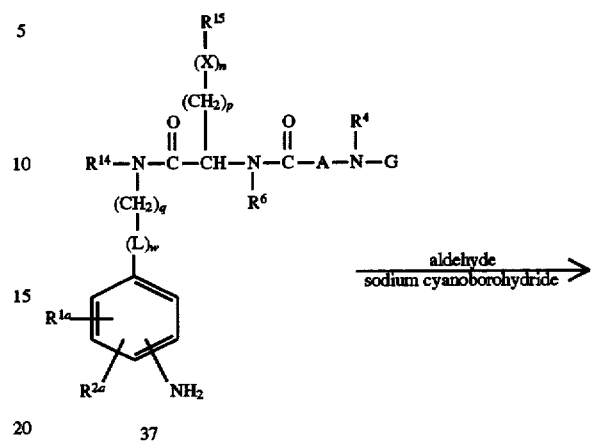

37

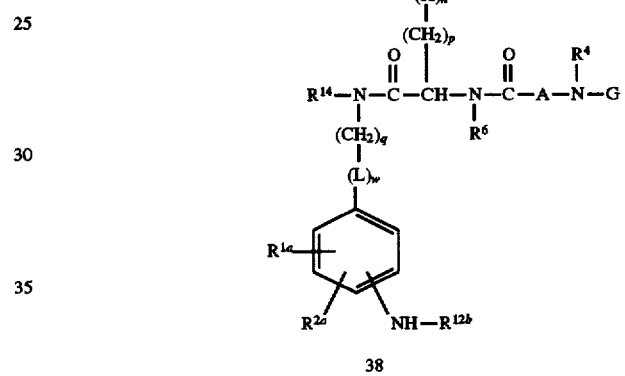

38

G is t-butoxycarbonyl

Elaboration of 37 to carbamate compounds is achieved by reaction with the appropriate chloroformate reagent in pyridine or in methylene chloride with triethylamine as shown in Scheme 17.

SCHEME 17

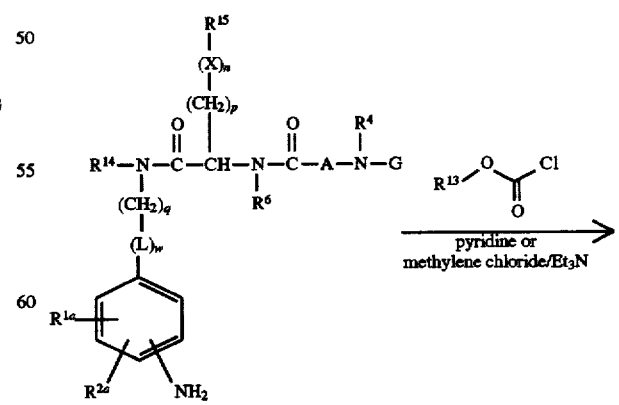

37

31
-continued
SCHEME 17

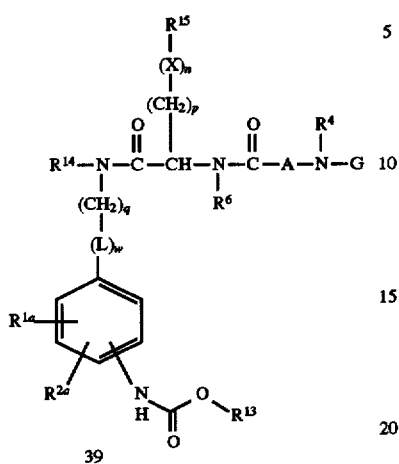

39

Transformation of amine intermediate 37 to urea derivatives is accomplished in several ways. Terminally disubstituted compounds 40 can be obtained directly by reaction of 37 with a disubstituted carbamoyl chloride in an inert solvent such as methylene chloride in the presence of triethylamine or 4-dimethylaminopyridine. In addition, monosubstituted compounds 41 wherein either $R^{4b}$ or $R^{12a}$ is hydrogen are obtained from 37 by reaction with an isocyanate as shown in Scheme 18.

SCHEME 18

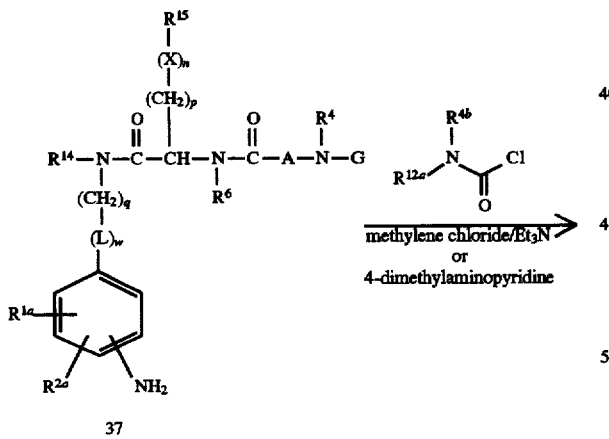

32
-continued
SCHEME 18

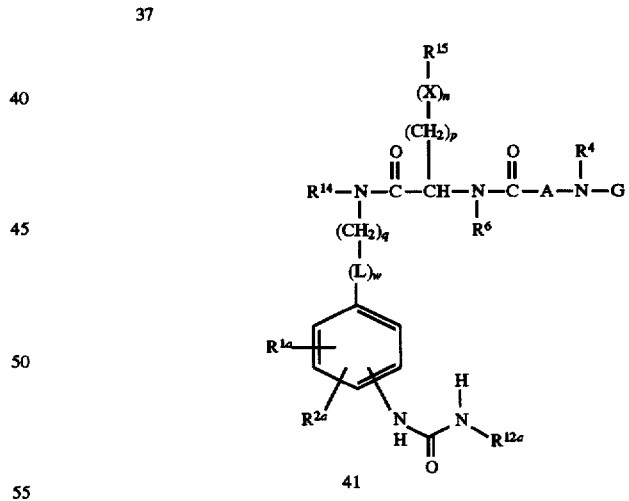

Alternatively, amine 37 is converted to an isocyanate 42 by treatment with phosgene or an equivalent reagent such as bis(trichloromethyl)carbonate (triphosgene) as indicated in Scheme 19. Subsequent reaction of 42 with primary or secondary amines in an inert solvent such as methylene chloride gives the corresponding urea derivates 43 in good yield. Isocyanate 42 is also converted to substituted semicarbazides 44 or hydroxy-or alkoxyureas 45 by reaction with substituted hydrazines or hydroxy-or alkoxylamines, respectively.

SCHEME 19
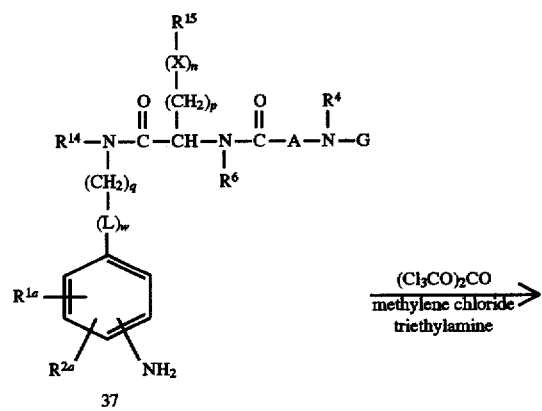
37
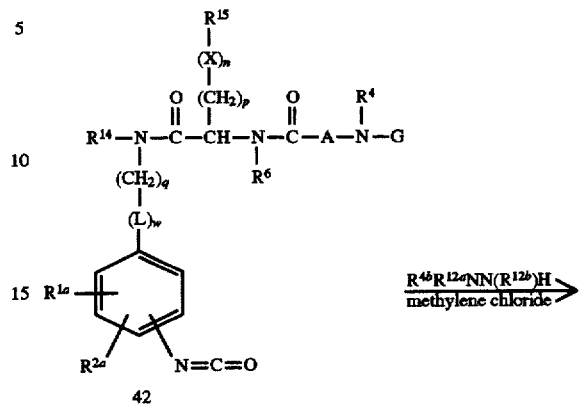
42
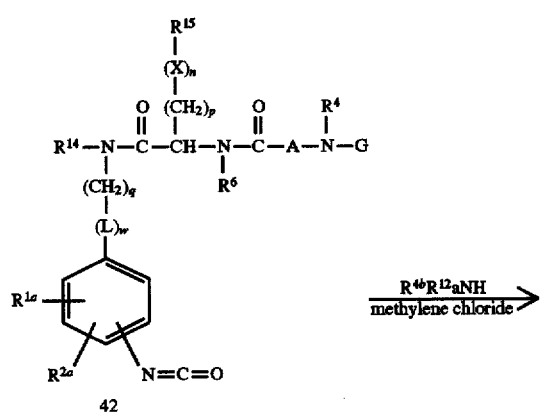
42
G is t-butoxycarbonyl or benzyloxycarbonyl
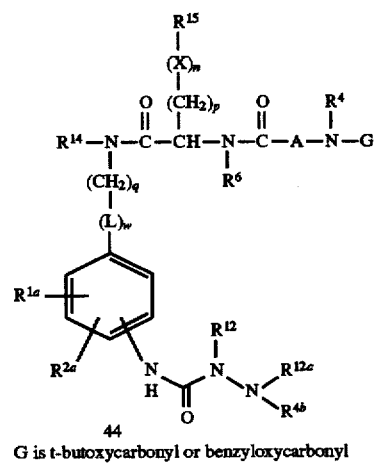
44
G is t-butoxycarbonyl or benzyloxycarbonyl
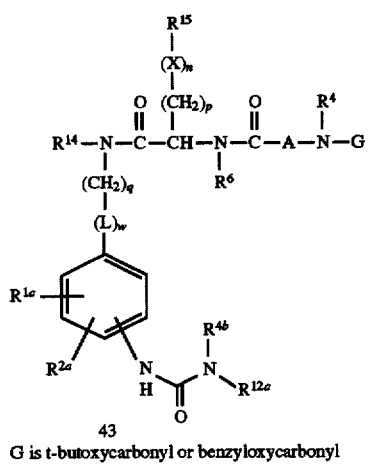
43
G is t-butoxycarbonyl or benzyloxycarbonyl

SCHEME 19 -continued

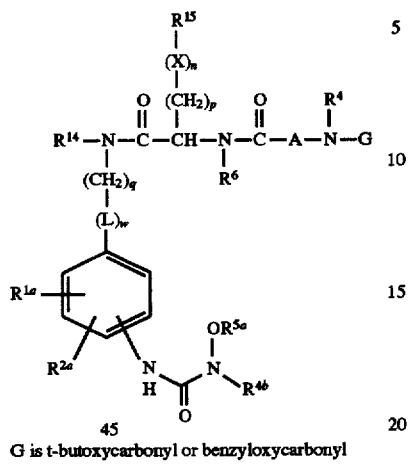

45

G is t-butoxycarbonyl or benzyloxycarbonyl

Compounds of formula I where $R^{3a}$ or $R^{3b}$ is a carbazate or carbamate derivative where attachment to the phenyl ring is through the oxygen atom of the carbazate or carbamate linkage are prepared from acetophenone intermediates 46 as indicated in Scheme 20.

SCHEME 20

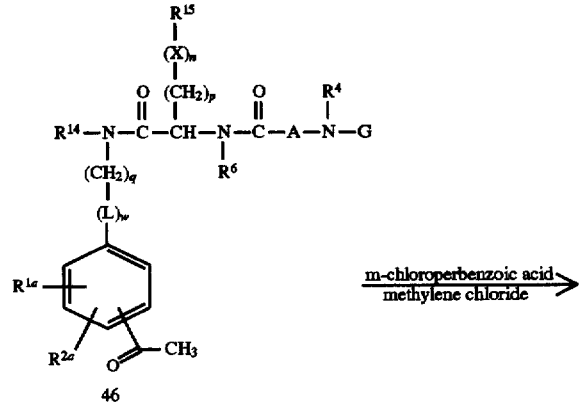

46

→ m-chloroperbenzoic acid / methylene chloride →

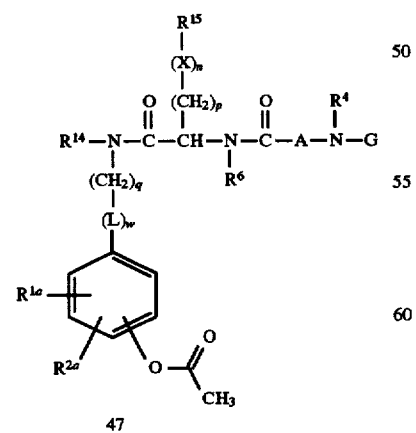

47

SCHEME 20 -continued

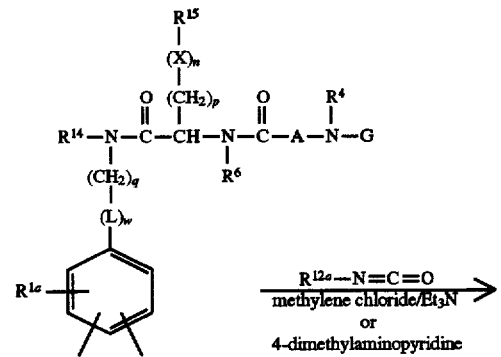

$\xrightarrow{\text{LiOH}}_{\text{H}_2\text{O}}$ 47

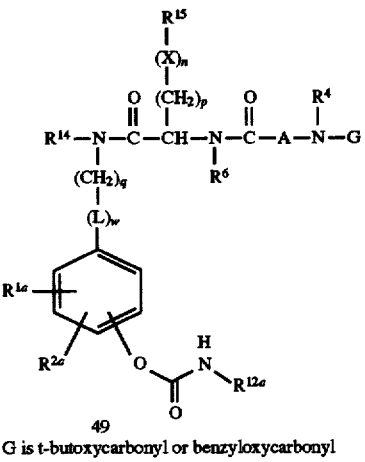

48

$\xrightarrow[\text{or 4-dimethylaminopyridine}]{R^{12a}-N=C=O \text{ methylene chloride/Et}_3\text{N}}$

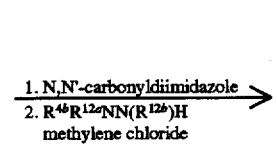

49

G is t-butoxycarbonyl or benzyloxycarbonyl

48

1. N,N'-carbonyldiimidazole
2. $R^{4b}R^{12a}NN(R^{12b})H$ methylene chloride →

-continued
SCHEME 20

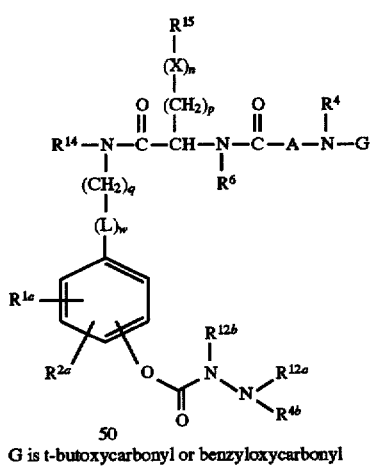

50

G is t-butoxycarbonyl or benzyloxycarbonyl

Oxidative rearrangement of 46 through the use of a peroxy-carboxylic acid (Baeyer-Villager reaction) such as m-chloroperbenzoic acid gives the ester 47 which is hydrolyzed in the presence of a strong base such as sodium or lithium hydroxide to give phenol 48.

Reaction of 48 with an isocyanate leads directly to carbamate analogs 49. Additionally, treatment of 48 with N,N'-carbonyldiimidazole in dimethylformamide can form an activated intermediate which will react with substituted hydrazine reagents to give carbazate products 50.

Compounds of formula I wherein $R^{3a}$ or $R^{3b}$ contains the linkage —$CH_2N(R^{12b})$— can be prepared from the t-butyl ester intermediate 51 as described in Scheme 21. Removal of the t-butyl ester through the use of trifluoroacetic acid gives the carboxylic acid 24. It may be appreciated by one skilled in the art that the protecting group G in 51 must therefore be compatible with the strongly acidic conditions employed for ester cleavage, hence G is taken as benzyloxycarbonyl. Conversion of the carboxylic acid to the benzylamine derivative 52 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 52 can be further elaborated to 53 by the aforementioned reductive amination procedure.

SCHEME 21

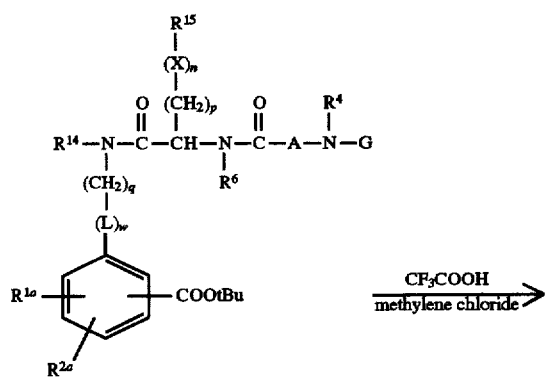

51

-continued
SCHEME 21

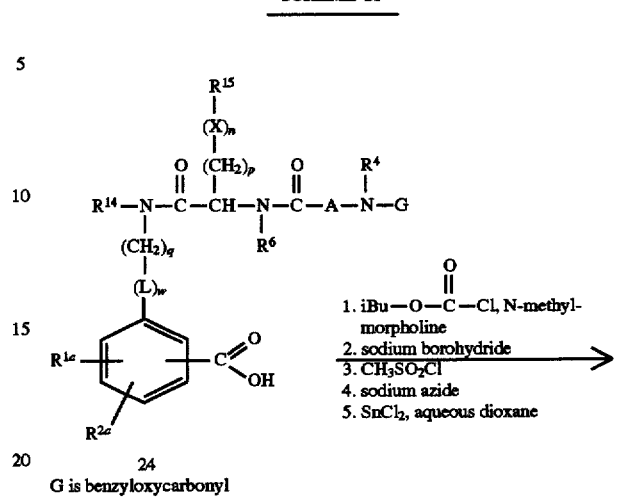

24
G is benzyloxycarbonyl

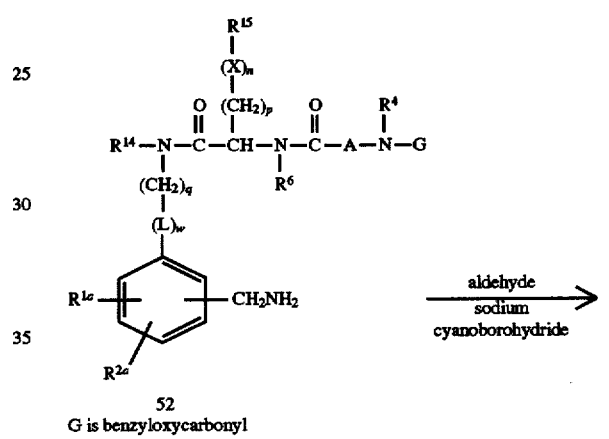

52
G is benzyloxycarbonyl

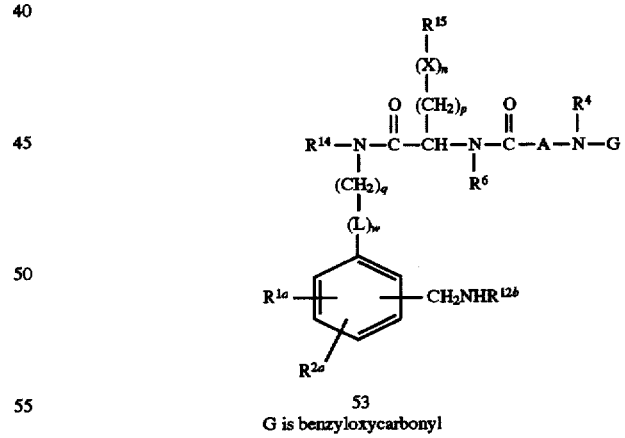

53
G is benzyloxycarbonyl

Reaction of amine 53 with the appropriate reagents to form urea-linked compounds 54 and 55 carbamate-linked compounds 56, and amide-linked structures 57 are illustrated in Scheme 22.

SCHEME 22
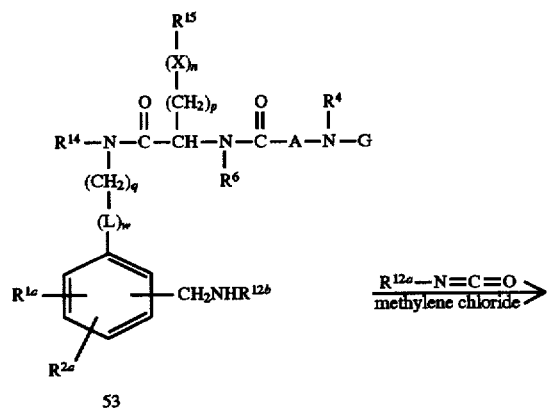
53
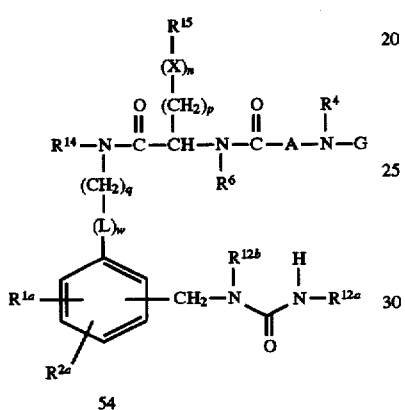
54
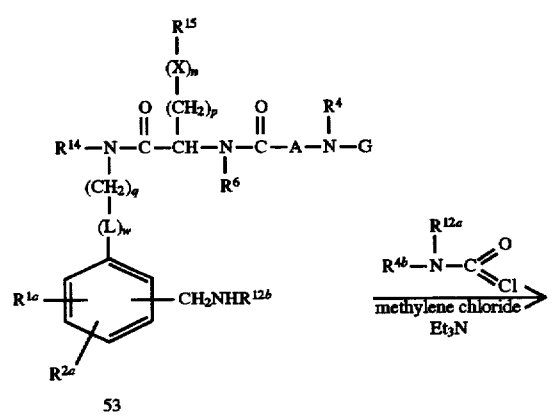
53
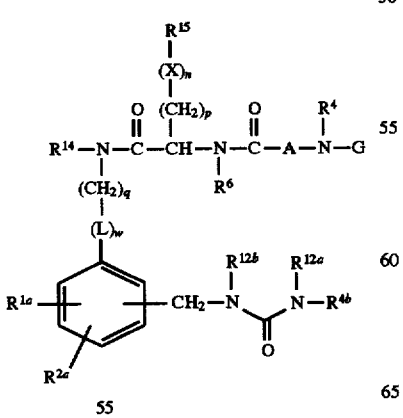
55
-continued
SCHEME 22
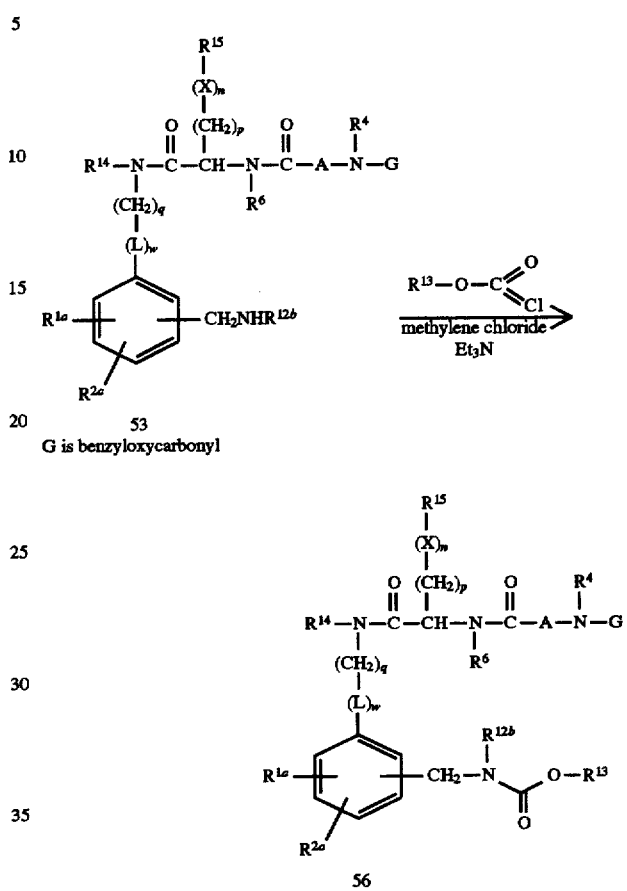
53
G is benzyloxycarbonyl
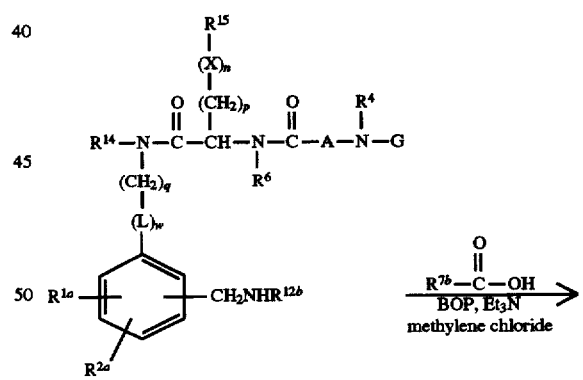
53
G is benzyloxycarbonyl

SCHEME 22 —continued

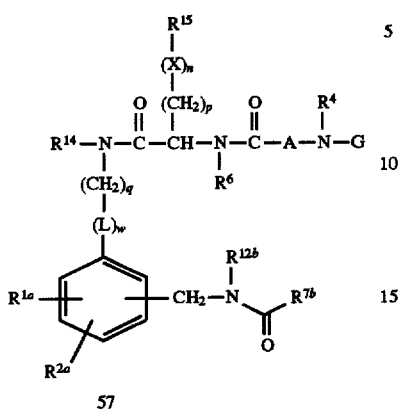

57

A useful preparation of the protected benzylamine intermediate 62 is shown in Scheme 23. Metallation of 4-bromobenzyl t-butyldimethylsilylether 58 with n-butyllithium followed by treatment with trimethyl borate gives the aryl boronic acid 59. Reaction of 59 with 2-bromo-N-(t-butoxycarbonyl)benzylamine 60 in the presence of tetrakis(triphenylphosphine)palladium(0) and barium hydroxide in aqueous 1,2-dimethoxyethane at elevated temperature gives the coupled product 61 in good yield. Desilylation is carried out by treatment with tetra-n-butylammonium fluoride; conversion to the 0-methanesulfonate 62 is achieved by reaction of the intermediate benzyl alcohol with methanesulfonic anhydride. Conversion to the requisite amine derivative V is achieved by the procedure described in Scheme 5.

SCHEME 23

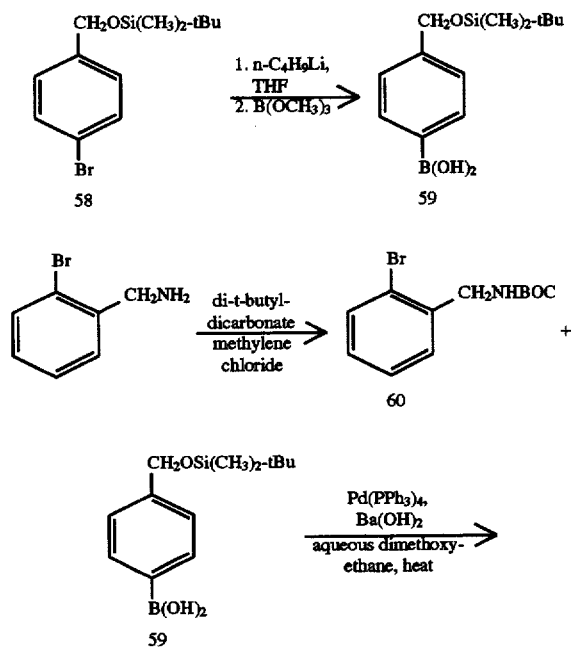

SCHEME 23 —continued

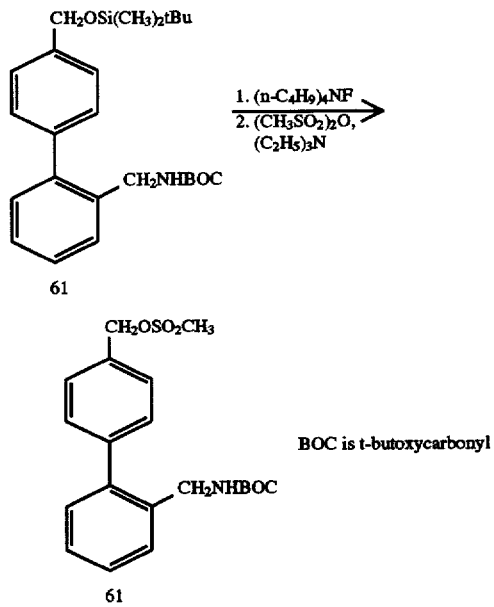

BOC is t-butoxycarbonyl

Conversion to the final products of formula I wherein $R^5$ is hydrogen, is carried out by simultaneous or sequential removal of all protecting groups from intermediate VII as illustrated in Scheme 24. Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Catalytic hydrogenation is also employed in the removal of N-triphenylmethyl (trityl) protecting groups. Removal of t-butoxycarbonyl (BOC) protecting groups is carded out by treatment of a solution in a solvent such as methylene chloride or methanol, with a strong acid, such as hydrochloric acid or trifluoroacetic acid. Conditions required to remove other protecting groups which may be present can be found in Protective Groups in Organic Synthesis.

SCHEME 24

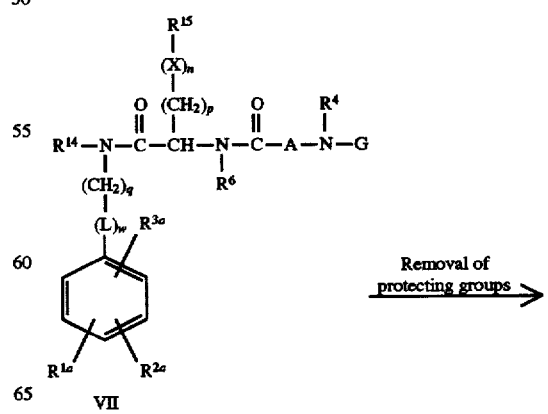

Removal of protecting groups →

-continued
SCHEME 24

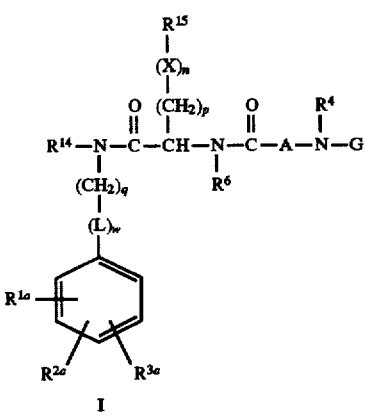

Compounds of formula I wherein $R^4$ and $R^5$ are each hydrogen can be further elaborated by reductive alkylation with an aldehyde by the aforementioned procedures or by alkylations such as by reaction with various epoxides as shown in Scheme 25. The products, obtained as hydrochloride or trifluoroacetate salts, are conveniently purified by reverse phase high performance liquid chromatography (HPLC) or by recrystallization.

SCHEME 25

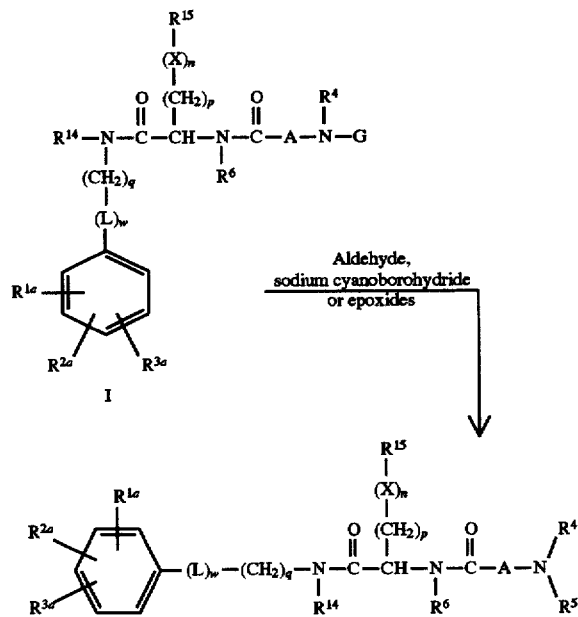

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, pinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel substituted dipeptide analogs is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed novel substituted dipeptide analogs is in combination with α2 adrenergic agonists or β3 adrenergic agonists in the treatment of obesity or in combination with parathyroid hormone or bisphosphonates, such as MK-217 (alendronate), in the treatment of osteoporosis.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

(R)-α-[(3-Amino-3-methyl-1-oxobutyl)amino]-N-[[2'-(1H-tetrazol-5-yl)[1,1'-biphenyl]-4-yl]methyl]benzene-butanamide, trifluoroacetate Step A: 5-Phenyltetrazole Zinc chloride (3.3 g, 24.3 mmol, 0.5 eq) was added to 15 mL of N,N-dimethylformamide in small portions while maintaining the temperature below 60° C. The suspension of zinc chloride was cooled to room temperature and treated with 5.0 g of benzonitrile (48.5 mmol, 1.0 eq) followed by 3.2 g of sodium azide (48.5 mmol, 1.0 eq). The heterogeneous mixture was heated at 115° C. with agitation for 18 hours. The mixture was cooled to room temperature, water (30 mL) was added and the mixture acidified by the addition of 5.1 mL of concentrated hydrochloric acid. The mixture was cooled to 0° C. and aged for one hour, then filtered and the filter cake washed with 15 mL of cold 0.1N HCl then dried at 60° C. under vacuum to afford 6.38 g (43.7 mmol, 90%) of the product.

Step B: 5-Phenyl-2-trityltetrazole

To a suspension of 5.0 g (34.2 mmol) of 5-phenyltetrazole in 55 mL of acetone was added 5.0 mL of triethylamine (3.6 g, 35.6 mmol, 1.04 eq). After 15 minutes, a solution of 10.0 g of triphenylmethyl chloride (35.9 mmol, 1.05 eq) in 20 mL of tetrahydrofuran was added and the mixture stirred at room temperature for one hour. Water (75 mL) was slowly added and the mixture stirred for one hour at room temperature. The product was collected by filtration, washed with 75 mL of water and dried at 60° C. under vacuum to give 13.3 g (34.2 mmol, 100%) of the product.

Step C: N-Triphenylmethyl-5-[2-(4'-methylbiphen-4-yl)]tetrazole

A solution of zinc chloride (6.3 g, 46.2 mmol, 0.6 eq) in 35 mL of tetrahydrofuran was dried over molecular sieves. 5-Phenyl-2-trityltetrazole (30.0 g, 77.3 mmol, 1.0 eq) was dissolved in 300 mL of dry tetrahydrofuran and the solution gently stirred while being degassed three times by alternating vacuum and nitrogen purges. The stirred solution was cooled to −15° C. and treated slowly with 50.5 mL of 1.6M n-butyllithium in hexane (80.0 mmol, 1.05 eq) so as to maintain the temperature below −5° C. The solution was maintained at −5° to −15° C. for 1.5 hours then treated with the dried zinc chloride solution and allowed to warm to room temperature.

In a separate flask, 4-iodotoluene (20.17 g, 92.5 mmol, 1.2 eq) and bis(triphenylphosphine)nickel(II)dichloride (1.5 g, 2.3 mmol, 0.03 eq) were dissolved in 60 mL of tetrahydrofuran, then degassed and left under an atmosphere of nitrogen. The mixture was cooled to 5° C. and treated with 1.5 mL of 3.0M solution of methylmagnesium chloride in tetrahydrofuran (4.5 mmol, 0.06 eq) so as to keep the temperature below 10° C. The solution was warmed to room temperature and added, under nitrogen purge, to the arylzinc solution. The reaction mixture was stirred vigorously for 8 hours at room temperature then quenched by the slow addition of a solution of 10 mL of glacial acetic acid (1.6 mmol, 0.02 eq) in 60 mL of tetrahydrofuran at a rate so that the temperature was maintained below 40° C. The mixture was stirred for 30 minutes and 150 mL of 80% saturated aqueous sodium chloride was added; the reaction mixture was extracted for 30 minutes and the layers allowed to separate. The organic layer was removed and washed with 150 mL of 80% saturated aqueous sodium chloride buffered to pH>10 by the addition of ammonium hydroxide. The organic phase was removed and concentrated under vacuum to approximately 50 mL then 250 mL of acetonitrile was added. The mixture was again concentrated under vacuum to 50 mL and acetonitrile added to make the final volume 150 mL. The resulting slurry was cooled at 5° C. for 1 hour then filtered and washed with 50 mL of cold acetonitrile followed by 150 mL of distilled water. The filter cake was air dried to a free flowing solid then further dried under vacuum at 50° C. for 12 hours to afford 30.0 g (62.8 mmol, 81%) of the product.

$^1$H NMR (200 MHz, CDCl$_3$): 2.28 (s,3H), 6.9–7.05 (m, 10H), 7.2–7.5 (m, 12H), 7.9 (m, 1H).

Step D: N-Triphenylmethyl-5-[2-(4'-bromomethylbiphen-4-yl)]tetrazole

A solution of 3.15 g (6.6 mmol) of N-triphenylmethyl-5-[2-(4'-methylbiphen-4-yl)]tetrazole in 25 mL of methylene chloride was treated with 1.29 g (7.25 mmol, 1.1 eq) of N-bromosuccinimide, 80 mg (0.5 mmol, 0.07 eq) of AIBN, 200 mg of sodium acetate and 200 mg of acetic acid. The mixture was heated at reflux for 16 hours then cooled and washed with saturated aqueous sodium bicarbonate. The organic layer was removed, dried over sodium sulfate, filtered and concentrated to a minimum volume by atmospheric distillation. Methyl t-butyl ether was added and distillation continued until almost all the methylene chloride was removed the the total volume reduced to approximately 12 mL and 12 mL of hexanes was then added. The mixture was kept at room temperature for 2 hours and the product isolated by filtration, washed with hexanes then dried under vacuum at 50° C. to give 2.81 g (5.04 mmol, 76%) of the product.

$^1$H NMR (200 MHz, CDCl$_3$): 4.38 (s, 2H), 6.9–8.0 (m, 23H). NMR indicates presence of approximately 1% of the starting material and 7% of the dibromo derivative.

Step E: N-Triphenylmethyl-5-[2-(4'-azidomethylbiphen-4-yl)]tetrazole

To 5.57 g (10 mmol) of N-triphenylmethyl-5-[2-(4'-bromomethylbiphen-4-yl)]tetrazole in 20 mL of dimethyl sulfoxide was added 614 mg (12.5 mmol, 1.25 eq) of pulverized lithium azide. The reaction was stirred at room temperature for 4 hours, during which time a thick precipitate formed. The precipitated solids were collected by filtration and washed with methanol, water, and then methanol again, and dried under vacuum for 16 hours to yield 4.06 g (78%) of the product as a white solid. $^1$H NMR (200 MHz, CDCl$_3$): 3.46 (s, 2H), 6.82–7.55 (m, 22H), 7.95 (m, 1H).

Step F: N-Triphenylmethyl-5-[2-(4'-aminomethylbiphen-4-yl)]tetrazole

To a solution of 4.06 g (7.8 mmol) of N-triphenylmethyl-5-[2-(4'azidomethylbiphen-4-yl)]-tetrazole in 15 mL of tetrahydrofuran was added 2.05 g (7.8 mmol, 1 eq) of triphenylphosphine in small portions. The mixture was stirred at room temperature for 2 hours, at which time 0.2 mL of water was added and the reaction mixture stirred for 16 hours. The reaction mixture was concentrated to dryness under vacuum and the crude product chromatographed on a silica flash column, eluting with chloroform, to give 1.5 g (3.03 mmol, 39%) of the product.

$^1$H NMR (200 MHz, CDCl$_3$): 2.21 (br s, 2H), 3.75 (s, 2H), 6.80–7.94 (m, 22H), 7.94 (m, 1H).

Step G: (R)-α-[t-Butoxycarbonylamino]-N-[[2'-N-triphenylmethyl-tetrazol-5-yl)[1,1'-biphenyl]-4-yl]methyl]benzenebutanamide To a solution of 30.5 mg (0.11 mmol) of N-BOC-D-homophenylalanine in 1 mL of methylene chloride at room temperature under a nitrogen atmosphere was added 54 mg (0.11 mmol, 1 eq) of N-triphenylmethyl-5-[2-(4'aminomethylbiphen-4-yl)]tetrazole (Step F), 25 mg (0.13 mmol, 1.2 eq) of 1-(3-dimethylaminopropyl)-3-ethylcarbodiimide hydrochloride and 13 mg (0.13 mmol, 1.2 eq) of triethylamine. The reaction was stirred at room temperature for 16 hours, then transferred to a separatory funnel and washed with 2 mL of 5 % aqueous citric acid and 2 mL of saturated aqueous sodium bicarbonate. The organic layer was removed, dried over magnesium sulfate, filtered and evaporated to dryness under vacuum. The residue was chromatographed on a silica flash column, eluting with hexane/ethyl acetate (5:1), to give 29 mg (35%) of the product.

$^1$H NMR (200 MHz, CDCl$_3$): 1.43 (s, 9H), 2.05 (m, 2H), 2.67 (t, 8 Hz, 2H), 4.05 (m, 1H), 4.32 (m, 1H), 4.99 (m, 1H), 6.19 (m, 1H), 6.78–7.15 (m, 27H), 7.95 (m, 1H).

Step H: (R)-α-[t-Butoxycarbonylamino]-N-[[2'-(1H-tetrazol-5-yl)[1,1'-biphenyl]-4-yl]methyl]benzenebutanamide A solution of 29 mg (0.038 mmol) of the intermediate obtained in Step G in 1 mL of methanol was hydrogenated at room temperature and one atmosphere over 4 mg of 20% palladium hydroxide on carbon for two hours. The reaction mixture was then filtered through Celite to remove the catalyst, the solvent removed under vacuum and the residue flash chromatographed on silica to yield 19 mg (95%) of the title compound.

$^1$H NMR (200 MHz, CD$_3$OD): 1.43 (s, 9H), 1.95 (m, 2H), 2.64 (m, 2H), 4.00 (m, 1H), 4.34 (t, 5 Hz, 2H), 7.00–7.30 (m, 8H), 7.50 (m, 5H). FAB-MS: calculated for C$_{29}$H$_{32}$N$_6$O$_3$ 512; found 513 (M+1, 24%).

Step I: (R)-α-Amino-N-[[2'-(1H-tetrazol-5-yl)[1,1'-biphenyl]-4yl]methyl]benzenebutanamide, hydrochloride A solution of 19 mg (0.037 mmol) of the intermediate obtained in Step H in 1 mL of methanol was treated with one drop of concentrated hydrochloric acid. The mixture was stirred at room temperature for 16 hours then evaporated to dryness under vacuum. The crude product was purified on reverse phase HPLC on C18, eluting with methanol/0.1% aqueous trifluoroacetic acid [linear gradient: 60% methanol to 80% methanol over 10 minutes], to yield 14 mg (84%) of the product.

$^1$H NMR (200 MHz, CD$_3$OD): 2.11 (m, 2H), 2.64 (m, 2H), 3.89 (t, 6 Hz, 1H), 4.42 (s, 2H), 7.05–7.32 (m, 8H), 7.58 (m, 5H). FAB-MS: calculated for C$_{24}$H$_{24}$N$_6$O 412; found 413 (M+1,100%).

49

Step J: 2,2-Dimethylbutanedioic acid, 4-methyl ester

2,2-Dimethylsuccinic acid (20 g, 137 mmol) dissolved in 200 mL of absolute methanol at 0° C. was treated dropwise with 2 mL of concentrated sulfuric acid. After the addition was complete, the mixture was allowed to warm to room temperature and stir for 16 hours. The mixture was concentrated under vacuum to 50 mL and slowly treated with 200 mL of saturated aqueous sodium bicarbonate. The mixture was washed with hexane (3×) and the aqueous layer removed and cooled in an ice bath. The mixture was acidified to pH 2 by slow addition of 6N HCl then extracted with ether (8×). The combined extracts were washed with brine, dried over magnesium sulfate, filtered and solvents removed under vacuum. The residue was dried at room temperature under vacuum to afford 14.7 g (91.8 mmol, 67%) of the product as a viscous oil that slowly solidified upon standing. $^1$H NMR (200 MHz, CDCl$_3$): 1.29 (s, 6H), 2.60 (s, 2H), 3.65 (s, 3H).

Step K: 3-Benzyloxycarbonylamino-3-methylbutanoic acid, methyl ester

To 14.7 g (91.8 mmol) of 2,2-dimethylbutanedioic acid-4-methyl ester in 150 mL of benzene was added 13 mL of triethylamine (9.4 g, 93 mmol) followed by 21.8 mL of diphenylphosphoryl azide (27.8 g, 101 mmol). The mixture was heated under nitrogen at reflux for 45 minutes then 19 mL (19.9 g, 184 mmol) of benzyl alcohol was added and refluxing continued for 16 hours. The mixture was cooled, filtered and the filtrate concentrated to a minimum volume under vacuum. The residue was redissolved in 250 mL of ethyl acetate, washed with water, saturated aqueous sodium bicarbonate (2×) and brine. The organic layer was removed, dried over magnesium sulfate, filtered and the filtrate concentrated to a minimum volume under vacuum. The crude product was purified by medium pressure liquid chromatography on silica, eluting with hexane/ethyl acetate (4:1), to afford 18.27 g (68.9 mmol, 75%) of the product.

$^1$H NMR (200 MHz, CDCl$_3$): 1.40 (s, 6H), 2.69 (s, 2H), 3.63 (s, 3H), 5.05 (s, 2H), 5.22 (br s, 1H), 7.32 (s, 5H).

Step L: 3-Benzyloxycarbonylamino-3-methylbutanoic acid

A solution of 18.27 g (68.9 mmol) of 3-benzyloxycarbonylamino-3-methylbutanoic acid methyl ester in 20 mL of methanol at room temperature was treated dropwise with 51 mL of 2N NaOH (102 mmol). The mixture was stirred at room temperature for 16 hours then transferred to a separatory funnel and washed with hexane (3×). The aqueous layer was removed, cooled to 0° C. and slowly acidified to pH 2 (paper) by dropwise addition of 6N HCl. This mixture was extracted with ether (6×); combined extracts were washed with 1N HCl and brine, then dried over magnesium sulfate, filtered and solvent removed under vacuum to afford 17.26 g (68.7 mmol, 99%) of the product.

$^1$H NMR (200 MHz, CDCl$_3$): 1.42 (s, 6H), 2.77 (s, 2H), 5.06 (s, 2H), 5.2 (br s, 1H), 7.3 (s, 5H).

Step M: 3-Benzyloxycarbonylamino-3-methylbutanoic acid, N-hydroxysuccinimide ester

A solution of 2.93 g (11.7 mmol, 0.85 eq) of 3-benzyloxycarbonylamino-3-methylbutanoic acid in 5 mL of methylene chloride at room temperature was treated with 1.61 g (14.0 mmol) of N-hydroxysuccinimide followed by 2.67 g (14.0 mmol, 1 eq) of 1(3-dimethylaminopropyl)-3-ethylcarbodiimide hydrochloride. The reaction mixture was stirred for 16 hours then transferred to a separatory funnel, washed with water and dilute aqueous sodium bicarbonate. The organic layer was removed, dried over magnesium sulfate, filtered, and solvents removed under vacuum. The crude product was chromatographed on a silica flash column, eluting with hexane/ethyl acetate (1:1), to give 3.9 g (quantitative) of the product.

50

$^1$H NMR (200 MHz, CDCl$_3$): 1.51 (s, 6H), 2.80 (s, 4H), 3.12 (s, 2H), 5.13 (s, 2H), 7.37 (s, 5H). FAB-MS: calculated for C$_{17}$H$_{20}$N$_2$O$_6$ 348; found 349 (M+1, 40%).

Step N: (R)-α-[(3-Benzyloxycarbonylamino-3-methyl-1-oxobutyl)amino]-N-[[2'-(1H-tetrazol-5-yl)-[1,1'-biphenyl]-4yl]methyl]benzenebutanamide

A solution of 12 mg (0.023 mmol) of the intermediate obtained in Step I in 0.5 mL of methylene chloride at room temperature was treated with 9.2 mg (0.027 mmol, 1.2 eq) of 3-benzyloxycarbonylamino-3-methylbutanoic acid, N-hydroxysuccinimide ester (Step M) and 3.5 mg (0.027 mmol, 1.2 eq) of diisopropylethylamine. The reaction mixture was stirred at room temperature for 48 hours. Solvents were removed under vacuum and the crude residue was purified on HPLC to give 14 mg of product.

$^1$H NMR (200 MHz, CD$_3$OD): 1.29 (s, 3H), 1.36 (s, 3H), 1.90 (m, 3H), 2.45 (m, 3H), 4.31 (m, 1H), 4.72 (d, 20 Hz, 1H), 5.02 (d, 20 Hz, 1H), 7.00–7.62 (m, 18H). FAB-MS: calculated for C$_{37}$H$_{39}$N$_7$O$_4$ 645; found 646 (M+1, 100%).

Step O: (R)-α-[(3-Amino-3-methyl-1-oxobutyl)amino]-N-[[2'-(1H-tetrazol-5-yl)[1,1'-biphenyl]-4-yl]methyl]benzenebutanamide, tri-fluoroacetate

A solution of 14 mg (0.21 mmol) of the intermediate obtained in Step N in 1 mL of methanol was hydrogenated at room temperature and one atmosphere over 1 mg of 20% palladium hydroxide on carbon for 16 hours. The reaction mixture was filtered through Celite and the filtrate concentrated under vacuum and the residue chromatographed on reverse phase high pressure liquid chromatography on C18, eluting with methanol/0.1% aqueous trifluoroacetic acid (linear gradient; 65% methanol increased to 85% over 10 minutes), to give 10 mg (72%) of the title compound.

$^1$H NMR (200 MHz, CD$_3$OD): 1.32 (s, 3H), 1.36 (s, 3H), 1.81 (m, 1H), 1.95 (m, 2H), 2.26 (m, 1H), 2.52 (s, 1H), 2.63 (m, 1H), 4.34 (m, 1H), 4.76 (d, 14 Hz, 1H), 4.95 (d, 14 Hz, 1H), 7.01–7.70 (m, 13H). FAB-MS: calculated for C$_{29}$H$_{33}$N$_7$O$_2$ 511; found 512 (M+1, 100%).

EXAMPLE 2

(R)-α-[(3-Amino-3-methyl-1-oxobutyl)amino]-N-[[2'-(1H-tetrazol-5-yl)[1,1'-biphenyl]-4-yl]methyl]benzene-propanamide, trifluoroacetate

The title compound was prepared from N-BOC-D-phenylalanine by the methods described in Example 1.

$^1$H NMR (200 MHz, CDCl$_3$): 1.27 (s, 3H), 1.40 (s, 3H), 2.49 (d, 15 Hz, 1H), 2.62 (d, 15 Hz, 1H), 3.10 (m, 2H), 4.44 (m, 2H), 4.80 (m, 1H), 7.16 (s, 4H), 7.35 (s, 5H); 7.70 (m, 4H). FAB-MS: calculated for C$_{28}$H$_{31}$N$_7$O$_2$ 497; found 498 (M+1,100%).

EXAMPLE 3

(R)-α-[(3-Amino-3-methyl-1-oxobutyl)amino]-N-[[2'-(1H-tetrazol-5-yl)[1,1'-biphenyl]-4-yl]methyl]-1H-indole-3-propanamide, trifluoroacetate

Step A: (R)-α-[t-Butoxycarbonylamino]-N-[[2'-N-triphenylmethyl-tetrazol-5-yl)[1,1'-biphenyl]-4-yl]methyl]-(N$_{im}$-formyl)indole-3-propanamide

Prepared from N-triphenylmethyl-5-[2-(4'-aminomethylbiphen-4-yl)]tetrazole and N$_{im}$-formyl-N$_α$-BOC-D-tryptophan by the procedure described in Example 1, Step G.

$^1$H NMR (200 MHz, CDCl$_3$): 1.40 (s, 9H), 3.18 (br s, 2H), 4.24 (br s, 2H), 4.48 (m, 1H), 5.24 (s, 1H), 6.28 (s, 1H), 6.70–7.70 (m, 27H), 7.90 (m, 1H), 8.82 (br s, 1H).

51

Step B: (R)-α-[t-Butoxycarbonylamino]-N-[[2'-(1H-tetrazol-5-yl)[1,1'-biphenyl]-4-yl]methyl]-(N$_{im}$-formyl) indole-3-propanamide Prepared from the intermediate obtained in Step A by the procedure described in Example 1, Step H.

¹H NMR (200 MHz, CD₃OD): 1.38 (s, 9H), 3.14 (m, 3H), 6.90–7.70 (m, 13H), 9.02 (br s, 1H). FAB-MS: calculated for C₃₀H₃₁N₇O₄ 553; found 554 (M+1,40%).

Step C: (R)-α-Amino-N-[[2'-(1H-tetrazol-5-yl)[1,1'-biphenyl-4-yl]methyl]-(N$_{im}$-formyl)indole-3-propanamide, trifluoroacetate A solution of 80 mg (0.14 mmol) of the intermediate obtained in Step B in 4 mL methylene chloride was treated with 1 mL of anisole followed by 4 mL of trifluoroacetic acid. The reaction mixture was stirred at room temperature for 1 hour, then all volatiles were removed under vacuum. The residue was purified by reverse phase high pressure liquid chromatography on C18, eluting with methanol/0.1% aqueous trifluoroacetic acid (45:55), to give 64 mg (77%) of the product.

¹H NMR (200 MHz, CD₃OD): 3.26 (m, 2H), 4.11 (t, 6 Hz, 1H), 4.28 (m, 2H), 6.99 (s, 4H), 7.28–7.70 (m, 9H), 8.75 (br s, 1H). FAB-MS: calculated for C₂₆H₂₃N₇O₂ 465; found 466 (M+1, 22%).

Step D: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well-stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step E without purification.

52

¹H NMR (200 MHz, CDCl₃): 1.45 (s, 6H), 2.75 (d, 3 Hz, 2H), 5.9 (br s, 1H).

Step E: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one, 800 mL of methylene chloride, 150 mL of triethylamine (1.08 mol) and 10.9 g (0.089 mol) of 4-dimethylaminopyridine. To the stirred solution at room temperature was added dropwise over 15 minutes a solution of 235 g (1.077 mol) of di-t-butyl-dicarbonate in 300 mL of methylene chloride. The reaction mixture was stirred at room temperature overnight then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step F without purification.

¹H NMR (200 MHz, CDCl₃): 1.50 (s, 9H), 1.54 (s, 6H), 2.77 (s, 2H).

Step F: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°–5° C. and treated dropwise with 890 mL of 1.0M aqueous lithium hydroxide over 30 minutes. The reaction mixture was stirred at 0°–5° C. for 2 hours then diluted with 1 L of ether and 1 L of water. The layers were allowed to separate and the aqueous layer was reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to give 173 g of a yellow oil that solidified upon standing. The material was slurried with warm hexane then filtered and dried under high vacuum to afford 168.5 g (0.775 mol, 87%) of product as a white solid.

¹H NMR (200 MHz, CDCl₃): 1.39 (s, 6H), 1.44 (s, 9H), 2.72 (s, 2H). FAB-MS: calculated for C₁₀H₁₉NO₄ 217; found 218 (M+H, 54%).

Step G: (R)-α-[(3-t-Butoxycarbonylamino-3-methyl-1-oxobutyl)amino]-N-[[2'-(1H-tetrazol-5-yl)-[1,1'-biphenyl]-4-yl]methyl]-(N$_{im}$-formyl)-indole-3-propanamide A solution of 64 mg (0.11 mmol) of the intermediate obtained in Step C in 1 mL of methylene chloride at 0° C. was treated with 25 mg (0.12 mmol, 1.1 eq) of dicyclohexylcarbodiimide and the resulting solution stirred at 0° C. for 30 minutes. A solution of 53 mg (0.24 mmol, 2 eq) of 3-t-butoxycarbonylamino-3-methylbutanoic acid and 12 mg (0.12 mmol, 0.017 mL, 1.1 eq) of triethylamine in 1 mL of methylene chloride was added and the mixture stirred for 5 hours at room temperature. The reaction mixture was evaporated to dryness under vacuum and the residue was dissolved in 1 mL of anisole and treated with 4 mL of trifluoroacetic acid. The mixture was stirred at room temperature for 30 minutes the concentrated under vacuum. The residue was taken up in methanol and the solids removed by filtration. The filtrate was concentrated under vacuum; the residue was purified by reverse phase high pressure liquid chromatography on C18 to yield 31 mg (42%) of the product.

¹H NMR (200 MHz, CD₃OD): 1.14 (s, 3H), 1.25 (s, 3H), 2.37 (d, 15 Hz, 1H), 2.48 (d, 15 Hz, 1H), 3.11 (m, 2H), 4.26

(m, 2H), 4.72 (m, 1H), 6.92–7.70 (m, 13H), 8.55 (br s, 1H). FAB-MS: calculated for $C_{31}H_{32}N_8O_3$ 564; found 565 (M+1, 80%).

Step H: (R)-α-[(3-Amino-3-methyl-1-oxobutyl)amino]-N-[[2'-(1H-tetrazol-5-yl)[1,1'-biphenyl]-4-yl]methyl]-1H-indole-3-propanamide, trifluoroacetate A solution of 31 mg (0.046 mmol) of the intermediate obtained in Step G in 1 mL of methanol was treated with 0.2 mL of concentrated hydrochloric acid and the resulting mixture heated at 65° C. for 1.5 hours. All volatiles were removed under vacuum and the residue purified by reverse phase high pressure liquid chromatography on C18, eluting with methanol/0.1% aqueous trifluoroacetic acid (50:50), to give 20 mg (67%) of the title compound.

$^1$H NMR (200 MHz, CD$_3$OD): 1.15 (s, 3H), 1.28 (s, 3H), 2.38 (d, 16 Hz, 1H), 2.50 (d, 16 Hz, 1H), 3.19 (m, 2H), 4.20 (d, 14 Hz, 1H), 4.32 (d, 14 Hz, 1H), 4.73 (t, 7 Hz, 1H), 6.90–7.70 (m, 13H). FAB-MS: calculated for $C_{30}H_{32}N_8O_2$ 536; found 536 (70%).

EXAMPLE 4

(R)-2-[(3-Amino-3-methyl-1-oxobutyl)amino]-N-phenyl-N-[[2'-(1H-tetrazol-5-yl)[1,1'-biphenyl]-4-yl]methyl]butanamide, trifluoroacetate Step A: (R)-2-(t-Butoxycarbonylamino)-N-phenylbutanamide Prepared from N-BOC-D-2-aminobutanoic acid and aniline by the method described in Example 1, Step G.

$^1$H NMR (200 MHz, CDCl$_3$): 1.00 (t, 6 Hz, 3H), 1.45 (s, 9H), 1.82 (m, 2H), 4.30 (m, 1H), 5.59 (d, 7 Hz, 1H), 7.00–7.62 (m, 5H), 8.90 (br s, 1H). FAB-MS: calculated for $C_{15}H_{22}N_2O_3$ 278; found 279 (M+1, 40%).

Step B: (R)-2-(t-Butoxycarbonylamino)-N-phenyl-N-[[2'-(N-triphenylmethyl-tetrazol-5-yl)-[1,1'-biphenyl]-4-yl]methyl]butanamide A solution of 70 mg (0.25 mmol) of (R)-2-(t-butoxycarbonylamino)-N-phenyl-butanamide in 0.5 mL of dry dimethylformamide was treated with 10 mg (0.25 mmol, 1 eq) of 60% sodium hydride oil dispersion. The mixture was stirred at room temperature for 20 minutes, then treated with a solution of 140 mg (0.25 mmol, 1 eq) of N-triphenylmethyl-5-[2-(4'-bromomethylbiphen-4-yl)] tetrazole (Example 1, Step D) in 0.5 mL of dry dimethylformamide. The mixture was stirred at room temperature for 2 hours, then quenched by the addition of 2 mL of water. The mixture was extracted several times with ethyl acetate; the combined extracts were washed with 5% aqueous citric acid, saturated aqueous sodium bicarbonate then dried over magnesium sulfate, filtered and the filtrate dried under vacuum. The crude material was chromatographed on a flash silica column, eluting with hexane/ethyl acetate (1:1), to give 91 mg (48%) of the product.

$^1$H NMR (200 MHz, CDCl$_3$): 0.74 (t, 6 Hz, 3H), 1.32 (s, 9H), 1.58 (m, 2H), 4.20 (m, 1H), 4.79 (s, 2H), 6.82–7.60 (m, 27H), 7.86 (m, 1H).

Step C: (R)-2-(t-Butoxycarbonylamino)-N-phenyl-N-[[2'-(1H-tetrazol-5-yl)-[1,1'-biphenyl]-4-yl]methyl]butanamide Prepared from the intermediate obtained in Step B by the procedure described in Example 1, Step H.

$^1$H NMR (200 MHz, CDCl$_3$): 0.74 (t, 6 Hz, 3H), 1.36 (s, 9H), 1.55 (m, 2H), 4.13 (m, 1H), 4.70 (d, 14 Hz, 1H), 5.02 (d, 14 Hz, 1H), 5.22 (m, 1H), 7.00–7.62 (m, 12H), 8.01 (m, 1H). FAB-MS: calculated for $C_{29}H_{32}N_6O_3$ 512; found 513 (M+1, 100%).

Step D: (R)-2-Amino-N-phenyl-N-[[2'-(1H-tetrazol-5-yl)[1,1'-biphenyl]-4-yl]methyl]butanamide, hydrochloride Prepared from the intermediate obtained in Step C by the method described in Example 1, Step I.

$^1$H NMR (200 MHz, CD$_3$OD): 0.83 (t, 7 Hz, 3H), 1.68 (m, 2H), 3.80 (m, 1H), 4.81 (d, 14 Hz, 1H), 5.01 (d, 14 Hz, 1H), 7.00–7.70 (m, 13H). FAB-MS: calculated for $C_{24}H_{24}N_6O$ 412; found 413 (M+1, 100%).

Step E: 3-t-Butoxycarbonylamino-3-methylbutanoic acid, N-hydroxysuccinimide ester Prepared from 3-t-butoxycarbonylamino-3-methylbutanoic acid (Example 3, Step F) and N-hydroxysuccinimide by the procedure describe in Example 1, Step M.

$^1$H NMR (200 MHz, CDCl$_3$): 1.41 (s, 9H), 1.43 (s, 6H), 2.82 (s, 4H), 3.07 (s, 2H), 4.72 (br s, 1H).

Step F: (R)-2-[(3-t-Butoxycarbonylamino-3-methyl-1-oxobutyl)amino]-N-phenyl-N-[[2'-(1H-tetrazol-5-yl)[1,1'-biphenyl]-4-yl]methyl]butanamide Prepared as in Example 1, Step N from (R)-2-amino-N-phenyl-N-[[2'-(1H-tetrazol-5-yl)[1,1'-biphenyl]-4-yl]methyl]butanamide, hydrochloride and 3-t-butoxycarbonylamino-3-methylbutanoic acid, N-hydroxysuccinimide ester.

$^1$H NMR (200 MHz, CD$_3$OD): 0.74 (t, 7 Hz, 3H), 1.32 (s, 6H), 1.40 (s, 9H), 1.58 (m, 2H), 2.45 (d, 13 Hz, 1H), 2.58 (d, 13 Hz, 1H), 4.29 (m, 1H), 4.78 (d, 14 Hz, 1H), 4.95 (d, 14 Hz, 1H), 6.97–7.79 (m, 13H). FAB-MS: calculated for $C_{34}H_{41}N_7O_4$ 611; found 612 (M+1, 100%).

Step G: (R)-2-[(3-Amino-3-methyl-1-oxobutyl)amino]-N-phenyl-N-[[2'-(1H-tetrazol-5-yl)[1,1'-biphenyl]-4-yl]methyl]butanamide, trifluoroacetate The title compound was prepared from the intermediate obtained in Step F by the procedure described in Example 3, Step H.

$^1$H NMR (200 MHz, CD$_3$OD): 0.72 (t, 7 Hz, 3H), 1.32 (s, 3H), 1.40 (s, H), 1.58 (m, 2H), 2.51 (m, 2H), 4.28 (m, 1H), 4.73 (d, 14 Hz, 1H), 4.99 (d, 14 Hz, 1H), 6.95–7.83 (m, 13H). FAB-MS: calculated for $C_{29}H_{33}N_7O_2$ 511; found 512 (M+1, 100%).

EXAMPLE 5

2-[(3-Amino-3-methyl-1-oxobutyl)amino]-N-[[2'-(1H-tetrazol-5-yl)[1,1'-biphenyl]-4-yl]methyl] acetamide, trifluoroacetate Step A: 2-t-Butoxycarbonylamino-N-[[2'-(N-triphenylmethyltetrazol-5-yl)[1,1'-biphenyl]-4-yl]methyl] acetamide Prepared from N-triphenylmethyl-5-[2-(4'-aminomethylbiphen-4-yl)]tetrazole (Example 1, Step F) and N-BOC-glycine by the procedure described in Example 1, Step G.

$^1$H NMR (200 MHz, CDCl$_3$): 1.43 (s, 9H), 3.72 (d, 5 Hz, 2H), 4.32 (d, 6 Hz, 2H), 5.06 (m, 1H), 6.30 (m, 1H), 6.82–7.68 (m, 22H), 7.95 (m, 1H).

Step B: 2-t-Butoxycarbonylamino-N-[[2'-(1H-tetrazol-5-yl)[1,1'-biphenyl]-4-yl]methyl]acetamide Prepared from the intermediate obtained in Step A by the procedure described in Example 1, Step H.

$^1$H NMR (200 MHz, CD$_3$OD): 1.42 (s, 9H), 3.69 (s, 2H), 4.38 (d, 6 Hz, 2H), 6.90–7.28 (m, 4H), 7.42–7.69 (m, 4H). FAB-MS: calculated for $C_{21}H_{24}N_6O_3$, 408; found 409 (M+1, 20%).

Step C: 2-Amino-N-[[2'-(1H-tetrazol-5-yl)[1,1'-biphenyl]-4-yl]methyl]acetamide, hydrochloride Prepared from the intermediate obtained in Step B by the procedure described in Example 1, Step I.

¹H NMR (200 MHz, CD₃OD): 3.84 (s, 2H), 4.35 (s, 2H), 7.10–7.83 (m, 8H). FAB-MS: calculated for C₁₆H₁₆N₆O 308; found 309 (M+1, 100%).

Step D: 2-[(3-Benzyloxycarbonylamino-3-methyl-1-oxobutyl)amino]-N-[[2'-(1H-tetrazol-5-yl)[1,1'-biphenyl]-4-yl]methyl]acetamide Prepared from the intermediate obtained in Step C and 3-benzyloxycarbonylamino-3-methylbutanoic acid, N-hydroxysuccinimide ester by the procedure described in Example 1, Step N.

¹H NMR (200 MHz, CD₃OD): 1.37 (s, 6H), 2.60 (s, 2H), 3.79 (s, 2H), 4.33 (s, 2H), 5.00 (s, 2H), 6.95–7.65 (m, 13H). FAB-MS: calculated for C₂₆H₃₃N₇O₄ 507; found 508 (M+1, 20%).

Step E: 2-[(3-Amino-3-methyl-1-oxobutyl)amino]-N-[[2'-(1H-tetrazol-5-yl)[1,1'-biphenyl]-4-yl]methyl]acetamide, trifluoroacetate Prepared from the intermediate obtained in Step D by the procedure described in Example 1, Step O.

¹H NMR (200 MHz, CD₃OD): 1.38 (s, 6H), 2.52 (s, 2H), 3.89 (s, 2H), 4.38 (s, 2H), 7.00–7.70 (m, 8H). FAB-MS: calculated for C₂₁H₂₅N₇O₂ 407; found 408 (M+1,100%).

EXAMPLE 6

(R)-α-[(2-Amino-2-methyl-1-oxopropyl)amino]-N-[[2'-[[(methylamino)carbonyl]amino][1,1'-biphenyl]-4-yl]methyl]-1H-indole-3-propanamide, trifluoroacetate Step A: N-(t-Butoxycarbonyl)-D-tryptophan benzyl ester Finely divided t-butoxycarbonyl-D-tryptophan (3 g, 10 mmol) was suspended in methylene chloride and benzyl alcohol (1.08 mL, 10 mmol) and 4-dimethylaminopyridine (0.12 g, 1 mmol) were added and stirred at room temperature. Solid 1-(3-dimethylaminopropyl)-3-ethylcarbodiimide hydrochloride (1.92 g, 10 mmol) was then added in three roughly equal portions over 5 minutes. The reaction mixture was stirred for 3 hours at room temperature during which time the reaction mixture became a homogeneous solution. The reaction mixture was poured into water (100 mL) and extracted with methylene chloride (2×50 mL). The combined methylene chloride layers were washed with 5% aqueous citric acid solution (100 mL) and 5% aqueous sodium bicarbonate solution (100 mL). The resulting methylene chloride layer was dried over magnesium sulfate, filtered and evaporated under vaccum to give an off-white solid. This solid material was chromatographed on silica gel using ethyl acetate/hexanes (2:3 v/v) as eluant. This afforded 3.56 g (91%) of the desired benzyl ester as a white amorphous powder.

¹H NMR (400 MHz, CDCl₃): 1.42 (s, 9H), 3.27 (d, 2H), 4.69 (m, 1H), 5.17 (ABq, 2H), 6.78 (br s, 1H), 7.15–7.42 (m, 8H), 7.53 (d, 1H), 7.97 (br s, 1H).

Step B: D-Tryptophan benzyl ester

N-(t-Butoxycarbonyl)-D-tryptophan benzyl ester (3.5 g, 8.87 mmol) was dissolved in methylene chloride (10 mL) and stirred at room temperature and trifluoroacetic acid (20 mL) was added dropwise to the ester. The reaction mixture was stirred at room temperature for one hour during which time the reaction darkened. The reaction mixture was directly evaporated under vacuum to give a white solid. This solid was dissolved in chloroform (100 mL) and washed with saturated aqueous sodium bicarbonate. The aqueous layer was extracted with chloroform (2×25 mL) and the combined chloroform layers were dried over potassium carbonate. Filtration and concentration of the chloroform solution under vacuum gave a pale yellow oil (3.14 g, 82%) which was mainly the desired product.

¹H NMR (400 MHz, CDCl₃): 1.58 (s, 9H), 3.09 (dd, 1H), 3.27 (dd, 1H), 3.88 (m, 1H), 5.10 (s, 2H), 6.93 (br s, 1H), 7.15–7.39 (m, 8H), 7.59 (d, 1H), 8.03 (br s, 1H).

Step C: (R)-α-[(2-t-Butoxycarbonylamino-2-methyl-1-oxopropyl)amino]-1H-indole-3-propanoic acid, benzyl ester Crude D-tryptophan benzyl ester (1.0 g, 3.40 mmol), 1-hydroxybenztriazole hydrate (0.63 g, 4.1 mmol) and t-butoxycarbonyl-α-methylalanine (0.84 g, 4.11 mmol) were stirred together at room temperature in chloroform (20 mL). 1-(3-Dimethylaminopropyl)-3-ethylcarbodiimide hydrochloride (980 mg, 5.11 mmol) was added to this mixture in a single portion. The reaction mixture was stirred at room temperature for 4 hours and worked up by pouring into water (50 mL). The chloroform layer was separated and washed with 5% aqueous citric acid solution (25 mL) and 5% aqueous sodium bicarbonate solution (25 mL). The chloroform layer was dried over magnesium sulfate, filtered and evaporated under vacuum to afford a thick oily foam. Chromatography on silica gel using ethyl acetate/hexanes (2:3 v/v) afforded a yellow foam (0.822 g 50%).

¹H NMR (400 MHz, CDCl₃): 1.30 (s, 9H), 1.39 (s, 6H), 3.29 (m, 2H), 4.88 (m, 1H), 5.03 (s, 2H), 6.88 (br s, 1H), 7.05–7.35 (m, 8H), 8.53 (d, 1H), 7.98 (br s, 1H).

Step D: (R)-α-[(2-t-Butoxycarbonylamino-2-methyl-1-oxopropyl)amino]-1H-indole-3-propanoic acid The benzyl ester (0.82 g, 1.71 mmol) obtained in Step C and 10% palladium on carbon (150 mg) were stirred together in ethyl acetate (5 mL). The solution was degassed and a hydrogen atmosphere introduced over the reactants using a balloon for 32 hours. The reaction products were isolated by filtering the reaction mixture through a Celite plug. The plug was washed with additional ethyl acetate (3×10 mL). The combined filtrates were evaporated under vacuum to afford the product (680 mg, 102%). ¹H NMR (400 MHz, CDCl₃): 1.30 (s, 9H), 1.41 (s, 6H), 3.32 (dd, 1H), 3.42 (m, 1H), 4.87 (br s, 1H), 6.82 (d, 1H), 7.13–7.35 (m, 8H), 7.60 (d, 1H), 8.28 (br s, 1H).

Step E: 4-Methyl-2'-nitro-1,1'-biphenyl

A vigorously stirred mixture of 34 g (0.25 mol) of 4-tolylboronic acid and 34 g (0.17 mol) of 2-bromo-1-nitrobenzene in a mixture of 170 mL of 5N sodium hydroxide, 57 mL of water, 215 mL of 2-propanol and 1080 mL of benzene was treated with 11.9 g of (tetrakis)triphenylphosphine palladium(0). The two-phase mixture was heated at reflux for three hours. The cooled reaction mixture was filtered through Celite and the filter cake washed with fresh benzene. The organic layer was separated and washed with water (3×), dried over magnesium sulfate and filtered. The filtrate was evaporated under vacuum and the residue (46.1 g) purified by preparative high pressure liquid chromatography on silica gel, eluting with hexane/ethyl acetate (20:1), to give 28.05 g of the product.

¹H NMR (400 MHz, CDCl₃): 2.38 (s, 3H), 7.20 (m, 4H), 7.43 (m, 2H), 7.59 (t, 1H), 7.8 (d, 1H). EI-MS: calculated for C₁₃H₁₁NO₂ 213; found 213 (M⁺).

Step F: 4-Bromomethyl-2'-nitro-1,1'-biphenyl

Prepared from 4-methyl-2'-nitro-1,1'-biphenyl by the procedure described in Example 1, Step D.

¹H NMR (200 MHz, CDCl₃): 4.53 (s, 2H), 7.2–7.7 (m, 7H), 7.85 (m, 1H).

Step G: 4-Azidomethyl-2'-nitro-1,1'-biphenyl

Prepared from 4-bromomethyl-2'-nitro-1,1'-biphenyl by the procedure described in Example 1, Step E.

¹H NMR (200 MHz, CDCl₃): 4.39 (s, 2H), 7.2–7.7 (m, 7H), 7.85 (d, 1H).

Step H: 4-Aminomethyl-2'-nitro-1,1'-biphenyl

Prepared from 4-azidomethyl-2'-nitro-1,1'-biphenyl by the procedure described in Example 1, Step E.

¹H NMR (200 MHz, CDCl₃): 3.90 (s, 2H), 7.2–7.7 (m, 7H), 7.83 (d, 1H).

Step I: (R)-α-[(2-t-Butoxycarbonylamino-2-methyl-1-oxopropyl)amino]-N-[[(2'-nitro)[1,1'-biphenyl]-4-yl]methyl]-1H-indole-3-propanamide The acid (338 mg, 0.87 mmol) from Step D and 4-aminomethyl-2'-nitro-1,1'-biphenyl (200 mg, 0.87 mmol) and triethylamine (0.245 mL, 1.76 mmol) were dissolved in methylene chloride (8 mL) and stirred at room temperature. Benzotriazolyl-1-yloxytris(dimethylamino)phosphonium hexafluorophosphate (388 mg, 0.87 mmol) was added in a single portion. The reaction mixture was stirred together for 3.5 hours then the reaction was quenched by adding saturated aqueous sodium chloride (10 mL) and extracted with methylene chloride (3×20 mL). The combined extracts were dried over magnesium sulfate, filtered and evaporated under vacuum. The resulting thick gum was chromatographed on silica gel using ethyl acetate/hexanes (1:2 v/v) to give 297 mg (50%) of an orange semi-solid.

¹H NMR (400 MHz, CD₃OD): 1.08 (s, 9H), 1.26 (s, 3H), 1.32 (s, 3H), 3.29 (dd, 1H), 3.43 (dd, 1H), 4.35 (m, 2H), 4.64 (m, 1H), 7.00–7.20 (m, 7H), 7.34 (d, 1H), 7.42 (m, 1H), 7.53 (t, 1H), 7.61 (d, 1H), 7.67 (t, 1H), 7.83 (d, 1H), 8.22 (s, 1H).

Step J: R-α-[(2-t-Butoxycarbonylamino-2-methyl-1-oxopropyl)amino]-N-[[2'-[[(methylamino)carbonyl]amino]-[1,1'-biphenyl]-4-yl]methyl]-1H-indole-3-propanamide The amide (120 mg, 0.20 mmol) from step I of this example was dissolved in ethanol (5 mL) and 10%-palladium on carbon (10 mg) was added. The ethanolic mixture was degassed and a hydrogen atmosphere introduced and maintained above the reaction mixture for 2.5 h using a balloon. The hydrogenation catalyst was removed by filtration through a Celite pad. The pad was washed carefully with methylene chloride. The combined filtrates were evaporated under vacuum to give a powdery white foam (108 mg, 95%).

¹H NMR (400 MHz,CDCl₃): 1.01 (s, 9H), 1.30 (s, 3H), 1.41 (s, 3H), 3.15 (dd, 1H), 3.55 (d, 1H), 4.23 (dd, 2H), 4.45 (d, 1H), 4.77(m, 1H) 6.87 to 7.65 (m, 13H). FAB-MS: calculated for C₃₃H₃₉N₅O₄ 569.3; found 570.1 (M+1).

Step K: R-α-[(2-Amino-2-methyl-1-oxopropyl)amino]-N-[[2'-[[(methylamino)carbonyl]amino][1,1'-biphenyl]-4-yl]methyl]-1H-indole-3-propanamide The amine (25mg, 0.04 mmol) from Step J of this example was dissolved in methylene chloride (0.5 mL) and methyl isocyanate (9 μL, 0.15 mmol) was added to the amine. The reaction mixture was stirred together at room temperature for 24 h then the volatiles were removed directly under vacuum. The resultant residues were chromatographed on silica gel using ethyl acetate: hexanes (4:1 v/v) to afford the desired urea (22.6 mg, 82%).

¹H NMR (200 MHz,CD₃OD): 1.10 (s, 9H), 1.24 (s, 3H), 1.30 (s, 3H), 2.64 (d, 3H), 3.33 (m, 2H), 4.33 (m, 2H), 4.58 (m, 1H), 6.96–7.80 (m, 13H). FAB-MS: calculated for C₃₅H₄₂N₆O₅ 626.3; found 627.2 (M+1).

Step L: R-α-[(2-Amino-2-methyl-1-oxopropyl)amino]-N-[[2'-[[(methylamino)carbonyl]amino][1,1'-biphenyl]-4-yl]methyl]-1H-indole-3-propanamide, trifluoroacetate The urea (15 mg, 0.024 mmol) from Step K of this example and anisole (10 μL) were dissolved in methanol (0.5 mL) and hexanes (0.5 ml) added. To this solution 9N hydrochloric acid (0.5 mL) was added. The reactants were stirred at room temperature for 0.5 h then the hexanes layer was removed using a pipette. The aqueous methanolic layer was evaporated at atmospheric pressure using a stream of nitrogen gas at room temperature. The solid material thus obtained was purified by reverse phase medium pressure liquid chromatography on C8 column, eluting with methanol: 0.1% aqueous trifluoroacetic acid (85:15 v/v). This afforded 11.3 mg (73 %) of the desired product.

¹H NMR (400 MHz,CD₃OD): 1.38 (s, 3H), 1.56 (s, 3H), 2.66 (s, 3H), 3.18(dd, 1H), 3.33 (dd, 1H), 4.35 (ABq, 2H), 4.78 (t, 1H), 6.98–7.47(m, 10H), 7.62 (d, 1H), 7.64 (d, 1H). FAB-MS: calculated for C₃₀H₃₄N₆O₃ 526.3; found 527.8.

EXAMPLE 7

(R)-α-[(2-Amino-2-methyl-1-oxypropyl)amino]-N-methyl-N-[[2'-(1H-tetrazol-5-yl)-[1,1'-biphenyl]-4-yl]methyl]benzenebutanamide trifluoroacetate and (R)-α-[(2-amino-2-methyl-1-oxypropyl)amino]-N-[[2'-cyano-[1,1'-biphenyl]-4-yl]methyl]-N-methyl-benzenebutanamide trifluoroacetate Step A: N-(t-Butoxycarbonyl)-D-homophenylalanine benzylester N-(t-Butoxycarbonyl)-D-homophenylalanine (2.0 g; 7.16 mmol) was dissolved in dry methylene chloride (14 ml) and benzyl alcohol (740 ml; 7.15 mmol) and 4-dimethylaminopyridine (DMAP) (87 mg, 0.7 mmol) were added. The mixture was stirred at room temperature and 1-(3-dimethylaminopropyl)-3-ethylcarbodiimide (EDC) was added in small batches over 5 minutes. The resulting homogeneous mixture was stirred at room temperature overnight. The reaction mixture was quenched by adding water (25 ml) and extracted with chloroform (50 ml). The chloroform layer was separated from the aqueous layer and then washed successively with 10% aqueous citric acid solution (50 ml) and with a 5% aqueous solution of sodium bicarbonate. The chloroform layer was then dried over magnesium sulfate powder, filtered and the volatiles evaporated under reduced pressure. The resultant thick yellow oil was chromatographed on silica gel using an eluant of 30% ethyl acetate and 70% hexane. This afforded a colorless oil that slowly solidified on standing at room temperature. The yield of N-(t-butoxycarbonyl)-D-homophenylalanine benzyl ester was 2.32 g (87.8%). FAB-MS: -calculated for C₂₂H₂₇NO₄ 369.2; found 370.1 (M+1).

Step B: D-Homophenylalanine benzyl ester

N-(t-Butoxycarbonyl)-D-homophenylalanine benzyl ester (2.32 g; 6.29 mmol) from Step A of this example was dissolved in dry methylene chloride (6.5 ml) and anisole (3.4 ml) was added. The reaction mixture was stirred vigorously at room temperature and trifluoroacetic acid (TFA) added. The reaction mixture was stirred at room temperature for 0.5 h and then the volatiles removed on a rotorvapor at reduced pressure. The residues were stored in the freezer overnight. The gummy residues were dissolved in methylene chloride (20 ml) and the methylene chloride layer washed with 10% sodium bicarbonate (ca 20 ml), dried over potassium carbonate powder. After filtering off the drying agent the methylene chloride phase was evaporated on a rotorvapor under reduced pressure. The gum thus obtained was chromatographed on silica gel using a solvent mixture comprising hexanes and ethyl acetate in the ratio 1:1 to remove the anisole and non polar materials then a 9:1 mixture to obtain the product amine. The yield of D-homophenylalanine benzyl ester was 1.28 g (75.5%). FAB-MS: -calculated for C₁₇H₁₉NO₂ 269.1; found 270.0 (M+1).

Step C: (R)-α-[(2-t-Butoxycarbonylamino-2-methyl-1-oxopropyl)amino]benzenebutanoic acid benzyl ester D-Homophenylalanine benzyl ester (0.87 g; 3.23 mmol), triethylamine (900 ml) and N-(t-butoxycarbonyl)-α-methylalanine (656 mg; 3.23 mmol) were dissolved in dry methylene chloride (6.5 ml) and benzotriazol-1-yloxytris (dimethylamino)phosphonium hexafluorophosphate (BOP-reagent) (1.43 g; 3.23 mmol) was added with stirring in small batches over 10 minutes. The reaction mixture was stirred at room temperature for 2.5 h then quenched by adding saturated brine (25 ml). The two phase system was extracted with methylene chloride (3×25 ml) and the combined methylene chloride extracts dried over magnesium sulfate powder, filtered and evaporated on a rotary evaporator under reduced pressure to give a colorless oil that solidified to an off white solid on standing at room temperature. This solid material was taken up in the minimum volume of methylene chloride and chromatographed on silica gel using an eluant composed of ethyl acetate and hexanes in the ratio 1:3 v/v. The product was isolated after evaporation of the volatiles as a white solid. The yield of the desired product was 1.30 g (88.5%). FAB-MS: -calculated for $C_{26}H_{34}N_2O_5$ 454.2; found 455.5 (M+1).

Step D: (R)-α-[(2-t-Butoxycarbonylamino-2-methyl-1-oxopropyl)amino]benzenebutanoic acid The ester (1.25 g; 2.75 mmol)) from Step C of this example was dissolved in ethanol (20 ml) and the hydrogenation catalyst, 10% palladium on charcoal (100 mg) added. The reaction mixture was stirred at room temperature and degassed using aspirator vacuum and an hydrogen atmosphere introduced over the reaction solution with a balloon. Hydrogenation at room temperature using the balloon was continued for 6 h and then the products isolated by filtration through a Celite pad contained in a sintered glass funnel. The pad was carefully washed with more methanol and methylene chloride and the combined filtrates were concentrated under reduced pressure. The thick oil that remained was dried under the high vacuum line. The isolated yield was 762 mg (76%). FAB-MS: -calculated for $C_{19}H_{28}N_2O_5$ 364.2; found 365.1 (M+1).

Step E: 4-Hydroxymethyl-2'-cyano-1,1'-biphenylmethanesulfonate ester

The alcohol, 4-hydroxymethyl-2'(t-butoxycarbonylaminomethyl)-1,1'-biphenyl (250 mg; 1.195 mmol) and methanesulfonyl chloride (116 μl; 1.50 mmol) were dissolved in methylene chloride (2.5 ml) and triethylamine was added (250 μl; 1.79 mmol) in a single portion. The reaction mixture was stirred at room temperature for 2.5 h and then the volatiles removed on a rotary evaporator under reduced pressure. The residues thus obtained were directly chromatographed on silica gel using a mixture of hexane and ethyl acetate 1:1 v/v. The sample was evaporated to dryness to give an amorphous powder. The yield of the methanesulfonate ester was 242 mg (71%).

Step F: 4-[(N-Methylamino)methyl]-2'-cyano-1,1'-biphenyl

The methanesulfonate ester (242 mg; 0.842 mmol) described in Step E of this example was dissolved in dry methylene chloride (50 ml) and an aqueous 40% solution of methylamine (50 ml) added. The two phase system was stirred at room temperature for 1.5 h and then the aqueous layer was removed and extracted with an equal volume of methylene chloride. The combined methylene chloride layers were dried over powdered anhydrous potassium carbonate, filtered and evaporated under reduced pressure and the residues stored in the refrigerator overnight. The residues were then chromatographed on silica gel on a short column using first neat ethyl acetate as the solvent then a mixture of ethyl acetate and ethanol (9:1 v/v) and finally with neat ethanol. In this way, 170.2 mg (91%) of the 4-[(N-methylamino)methyl]-2'-cyano-1,1'-biphenyl, was obtained as an oil that slowly solidified on standing. FAB-MS:- calculated for $C_{15}H_{14}N_2$ 222.1; found 222.7 (M).

Step G: (R)-α-[(2-t-Butoxycarbonylamino-2-methyl-1-oxypropyl)amino]-N-methyl-N-[[(2'-cyano)-[1,1'-biphenyl]-4-yl]methyl]benzenebutanamide The acid from Step D (82 mg; 0.225 mmol), the amine (50 mg; 0.225 mmol) from Step F of this example and triethylamine (63 μl; 0.052 mmol) were dissolved in dry methylene chloride (1 ml) and stirred at room temperature. BOP (100 mg; 0.226 mmol) was added in a single portion and the reactants stirred at room temperature overnight for 17 h. The reaction was then quenched by adding brine (5 ml) and extracting with methylene chloride (2×10 ml). The combined methylene chloride layers were dried over anhydrous magnesium sulfate powder, filtered and evaporated under reduced pressure to give a golden yellow oil. The oil was then chromatographed on silica gel using an eluant of ethyl acetate and hexanes 2:1 v/v. This afforded the product as a colorless oil and the yield was 131 mg. FAB-MS:- calculated for $C_{34}H_{40}N_4O_4$ 568.3; found 569.6 (M+1).

Step H: (R)-α-[(2-Amino-2-methyl-1-oxypropyl)amino]-N-methyl-N-[[2'-(1H-tetrazol-5-yl)-[1,1'-biphenyl]-4-yl] methyl]benzenebutanamide, trifluoroacetate and (R)-α-[(2-Amino-2-methyl-1-oxypropyl)amino]-N-[[2'-cyano-[1,1'-biphenyl]-4-yl]methyl]-N-methyl-benzenebutanamide, trifluoroacetate The nitrile (131 mg, 0.23 mmol) from Step G of this example was dissolved in toluene (2 ml) and stirred at room temperature. Trimethyltin azide (142 mg; 0.69 mmol) was added in a single portion and the reaction mixture was then heated to reflux for 44 h. The volatiles were then removed on a rotary evaporator under reduced pressure to leave a thick gum. This crude product was then dissolved up in a mixture of methanol (1 ml), anisole (0.5 ml) and hexanes (1 ml). Hydrochloric acid (9N, 0.5 ml) was added to the crude product solution and the reactants stirred at room temperature for 1 h. The hexanes layer was then removed using a Pasteur pipette and the aqueous methanolic solution of the products evaporated to dryness using a nitrogen gas stream overnight. The resulting solid was then purified by hplc using a C18 reversed phase column using a solvent gradient of methanol and 0.1% aqueous trifluoroacetic acid. The were two products that were isolated. The faster moving product on reversed phase hplc was (R)-α-[(2-amino-2-methyl-1-oxypropyl)amino]-N-methyl N-[[2'-(1H-tetrazol-5-yl)-[1,1'-biphenyl]-4-yl]methyl]benzenebutenamide trifluoroacetic acid salt, 28.2 mg (19.6 %).

$^1$H NMR (400 MHz, $CD_3OD$): 1.62 (s, 3H) 1.65 (s, 3H) 2.05 (m, 2H) 2.5–2.85 (m, 2H) 2.81 (s, 3H) 4.33 and 4.56 (2×ABq, 2H total) 4.83 (m, 1H) 7.15–7.3 and 7.5–7.8 (m, 13H), 8.28 (t, 1H, incompletely exchanged NH). FAB-MS:- calculated for $C_{29}H_{33}N_7O_2$ 511.3; found 512.5 (M+1).

The slower moving compound on reversed phase hplc was the nitrile compound (R)-α-[(2-amino-2-methyl-1-oxypropyl)amino]-N-[[2'-cyano-[1,1'-biphenyl]-4-yl]methyl]-N-methyl-benzenebutanamide trifluoro-acetic acid salt 48.5 mg (36.2%).

$^1$H NMR (400 MHz, $CD_3OD$): 1.63 (d, 3H) 1.66 (d, 3H) 1.9–2.16 (m, 2H) 2.5–2.85 (m, 2H) 2.88 (s, 3H) 4.47–4.54 and 4.8–4.9 (complex, 2H) 4.78 (m, 1H) 7.05–7.85 (m, 13H). FAB-MS:- calculated for $C_{29}H_{32}N_4O_2$ 468.3; found 469.3 (M+1).

EXAMPLE 8

(R)-α-[(3-Amino-3-methyl-1-oxybutyl)amino]-N-methyl-N-[[2'-(1H-tetrazol-5-yl)-[1,1'-biphenyl]-4-yl]methyl]benzenebutanamide, trifluoroacetate and (R)-α-[(2-Amino-2-methyl-1-oxypropyl)amino]-N-[[2'-cyano-[1,1'-biphenyl]-4-yl]methyl]-N-methyl-benzenebutanamide, trifluoroacetate Step A: (R)-α-[(3-t-Butoxycarbonylamino-3-methyl-1-oxobutyl)amino]benzenebutanoic acid benzyl ester D-Homophenylalanine benzyl ester (725 mg; 3.23 mmol) whose preparation was described in Example 7 Step B, triethylamine (750 ml; 5.38 mmol) and 3-t-butoxycarbonylamino-3-methylbutanoic acid (585 mg; 2.69 mmol) were dissolved in dry methylene chloride (10 ml) and BOP (1.19 g, 2.69 mmol) was added with stirring in small batches to give a slightly cloudy solution. The reaction mixture was stirred at room temperature for 24 h then quenched by adding saturated brine (10 ml). The two phase system was extracted with methylene chloride (2×25 ml) and the combined methylene chloride extracts dried over magnesium sulfate powder, filtered and evaporated on a rotary evaporator under reduced pressure to give a cloudy, colorless oil. This material was taken up in the minimum volume of methylene chloride and chromatographed on silica gel using an eluant composed of ethyl acetate and hexanes in the ratio 1:1 v/v. The product was isolated after evaporation of the volatiles as a clear oil. The yield was 710 mg (88.5%). FAB-MS: -calculated for $C_{27}H_{36}N_2O_5$ 468.3; found 469.6 (M+1).

Step B: (R)-α-[(3-t-Butoxycarbonylamino-3-methyl-1-oxobutyl)amino]benzenebutanoic acid The benzyl ester (710 mg; 1.52 mmol) whose preparation is described in step A of this example was dissolved in methanol (15 ml) and the hydrogenation catalyst, 10% palladium on charcoal (125 mg) added. The reaction mixture was stirred at room temperature and degassed using aspirator vacuum and a hydrogen atmosphere introduced over the reaction solution with the aid of a balloon. Hydrogenation at room temperature using the balloon was continued overnight and then the products isolated by filtration through a Celite pad contained in a sintered glass funnel. The pad was carefully washed with methylene chloride and the combined filtrates were concentrated under reduced pressure. The thick oil that remained was dried under high vacuum. The isolated yield was 427 mg (74.2%). FAB-MS: -calculated for $C_{20}H_{30}N_2O_5$ 378.2; found 379.1 (M+1).

Step C: (R)-α-[(3-t-Butoxycarbonylamino-3-methyl-1-oxybutyl)amino]-N-methyl-N-[[(2'-cyano)-[1,1'-biphenyl]-4-yl]methyl]benzenebutanamide The acid from step C (85 mg; 0.225 mmol) of this example, the amine (50 mg; 0.225 mmol) from Step F of Example 7 and triethylamine (63 μl; 0.452 mmol) were dissolved in dry methylene chloride (1 ml) and stirred at room temperature. BOP (100 mg; 0.226 mmol) was added in a single portion and the reactants stirred at room temperature overnight for 17 h. The reaction was then quenched by adding brine (5 ml) and extracting with methylene chloride (2×10 ml). The combined methylene chloride layers were dried over anhydrous magnesium sulfate powder, filtered and evaporated under reduced pressure to give a golden yellow oil. The oil was then chromatographed on silica gel using an eluant of ethyl acetate and hexanes 2:1 v/v. This afforded the product as a colorless oil. The yield was 75 mg (57.2 %). FAB-MS:-cacluated for $C_{35}H_{42}N_4O_4$ 582.3 found 583.6 (M+1).

Step D: (R)-α-[(3-Amino-3-methyl-1-oxybutyl)amino]-N-methyl-N-[[2'-(1H-tetrazol-5-yl)-[1,1'-biphenyl]-4-yl]methyl]benzenebutanamide, trifluoroacetate and (R)-α-[(2-Amino-2-methyl-1-oxypropyl)amino]-N-[[2'-cyano-[1,1'-biphenyl]-4-yl]methyl]-N-methylbenzenebutanamide, trifluoroacetate The nitrile (71 mg, 0.122 mmol) from Step C of this Example was dissolved in toluene (2 ml) and stirred at room temperature. Trimethyltin azide (75 mg; 0.364 mmol) was added in a single portion and the reaction mixture was then heated to reflux for 44 h. The volatiles were then removed on a rotary evaporator under reduced pressure to leave a thick gum. This crude product was then dissolved up in a mixture of methanol (1 ml), anisole (0.5 ml) and hexanes (1 ml). Hydrochloric acid (9N, 0.5 ml) was added to the crude product solution and the reactants stirred at room temperature for 1 h. The hexanes layer was then removed using a Pasteur pipette and the aqueous methanolic solution of the products evaporated to dryness using a nitrogen gas stream overnight. The resulting solid was then purified by hplc using a C18 reversed phase column using a solvent gradient of methanol and 0.1% aqueous trifluoroacetic acid. The were two products that were isolated. The faster product was the title compound which contained the triazole (7.1 mg; 9.1%). $^1$H NMR (400 MHz, CD$_3$OD): 1.37 (s, 3H) 1.42 (s, 3H) 1.97 (m, 2H) 2.55 (2×s, 2H) 2.55–2.9 (m, 2H) 2.83 (d, 3H) 4.30–4.48 and 4.63–4.85 (m, 3H) 7.06–7.33 and 7.50–7.82 (m, 13H). FAB-MS:- calculated for $C_{30}H_{35}N_7O_2$ 525.3; found 526.5 (M+1).

The slower moving compound was the nitrile compound (R)-α-[(2-amino-2-methyl-1-oxypropyl)amino]-N-[[2'-cyano-[1,1'-biphenyl]-4-yl]methyl]-N-methyl-benzenebutanamide trifluoroacetic acid salt (40.6 mg; 55.8 %). $^1$H NMR (400 MHz, CD$_3$OD): 1.38 (d, 3H) 1.41(d, 3H) 2.01 (m, 2H) 2.50–2.65 (2×d, 2H) 2.50–2.85 (m, 2H) 2.92 (s, 3H) 4.45–4.58 and 4.73–4.85 (m, 3H) 7.07–7.85 (m, 13H). FAB-MS: -calculated for $C_{30}H_{34}N_4O_2$ 482.3; found 483.4 (M+1).

EXAMPLE 9

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl] benzenebutanamide, trifluoroacetate Step A: N-(t-Butoxycarbonyl)-D-homophenylalanine allyl ester N-(t-Butoxycarbonyl)-D-homophenylalanine (2.0 g; 7.16 mmol), allyl alcohol (500 ml; 7.35 mmol) and 4-dimethylaminopyridine (88 mg; 0.72 mmol) were dissolved in dry methylene chloride and stirred at room temperature. EDC (1.4 g; 7.30 mmol) was added to the solution in small batches over 15 minutes and the reaction mixture stirred at room temperature for 6 h. The reaction was quenched by pouring the reaction mixture into water (10 ml) and extracted with methylene chloride (2×25 ml). The combined methylene chloride extracts were washed successively with 5% aqueous citric acid solution (50 ml) and a 10% aqueous sodium carbonate solution. The methylene chloride layer was dried over anhydrous magnesium surf ate powder, filtered and evaporated to leave a thick oily residue which was purified by column chromatography on silica gel using an eluant comprising ethyl acetate and hexanes in the ratio 2:1. The yield of the desired allyl ester product was 1.96 g (85.7%). FAB-MS:- calculated for $C_{18}H_{25}NO_4$ 319.2; found 320. (M+1).

Step B: D-Homophenylalanine allyl ester

The allyl ester from Step A of this Example (1.96 g; 6.136 mmol) was dissolved in dry methylene chloride (10 ml) and anisole (5 ml) was added. The mixture was stirred at room temperature and trifluoroacetic acid was added drop by drop to the ester over 5 minutes. The reaction mixture was stirred at room temperature for a further 2 h then the volatiles removed on a rotary evaporator under reduced pressure to give a thick oil. The oil was dissolved in methylene chloride (50 ml) and shaken with a saturated aqueous solution of sodium bicarbonate. The aqueous layer was discarded and the methylene chloride layer dried over anhydrous magnesium sulfate powder, filtered and the volatiles removed under reduced pressure. The oil that remained after evaporation was chromatographed on silica gel using a solvent gradient beginning with ethyl acetate and hexanes (1:1) to neat ethyl acetate and then with a eluant of ethanol and ethyl acetate in the ratio 1:4 v/v. The product (1.1 g; 81.7%) was isolated after the chromatography. FAB-MS:- calculated for $C13H_{17}NO_2$ 219.1; found 219.8 (M).

Step C: (R)-α-[(2-Benzyloxycarbonylamino-2-methyl-1-oxopropyl)amino]benzenebutanoic acid allyl ester The amine obtained in Step B of this Example (300 mg; 1.37 mmol) triethylamine (380 ml; 2.73 mmol) and N-carbobenzyloxy-2-methylalanine (278 mg; 1.37 mmol) were dissolved in dry methylene chloride (3 ml) and BOP (605 mg; 1.37 mmol) was added. The reaction mixture was stirred at room temperature for 2 h and the resultant homogenous yellow solution quenched by addition of brine. The two phase system was extracted with methylene chloride (2×25 ml) and the combined methylene chloride layers dried over powdered anhydrous magnesium sulfate. Filtration of the methylene chloride solution to remove the spent drying agent followed by evaporation of solvent afforded an oil which was purified by column chromatography on silica gel using a solvent mixture of ethyl acetate and hexanes (1:1 v/v) as eluant. The desired product (419 mg; 69.7%) was isolated as a white amorphous solid. FAB-MS:- calculated for $C_{25}H_{30}N_2O_5$ 438.2; found 439.3 (M+1).

Step D: (R)-α-[(2-Benzyloxycarbonylamino-2-methyl-1-oxopropyl)amino]benzenebutanoic acid The allyl ester from Step C of this Example was deallylated using a modification of the method reported by P. D. Jeffrey and S. W. McCombie (J. Org. Chem., 1982, 47, 587). The allyl ester (120 mg; 0.27 mmol), triphenylphosphine (3 mg) were dissolved in dry methylene chloride and tetrakis(triphenyl-phosphine)palladium(0) (3 mg) added. A solution of potassium 2-methylhexanoate (0.5M in ethyl acetate)(0.6 ml; 0.3 mmol) was added. The reaction mixture was stirred at room temperature for 12 h under nitrogen and the volatiles removed under reduced pressure. The products were chromatographed on a short silica gel column using a solvent gradient of ethyl acetate and hexanes (2:1 v/v) then neat ethyl acetate and finally ethyl acetate and ethanol (1:9 v/v). The product (48.2 mg; 44.8%) was isolated as a white solid. FAB-MS:- calculated for $C_{22}H_{26}N_2O_5$ 398.2; found 421.1 (M+Na).

Step E: 4-Hydroxymethyl-2'(t-butoxycarbonylaminomethyl)-1,1'-biphenyl methanesulfonate ester 4-Hydroxymethyl-2'(t-butoxycarbonylaminomethyl)-1,1'-biphenyl (250 mg; 0.8 mmol) was dissolved in dry methylene chloride (3 ml) and triethylamine (167 ml; 1.20 mmol) was added at room temperature followed by methanesulfonyl chloride (77.3 ml; 1.0 mmol). The reactants were stirred together for 2.5 h and the volatiles removed under reduced pressure using a rotary evaporator. The residue, a thick pasty solid, was chromatographed on a short column containing silica gel and using an eluant comprising ether hexanes mixture in the ratio 1:2. The product was isolated as a white solid. The yield was 84 mg (27%). Some starting material (164 mg) was also recovered.

Step F: 4-[N-Methylamino)methyl]-2'(t-butoxycarbonylaminomethyl)-1,1'-biphenyl

The mesylate (84 mg; 0.215 mmol) was dissolved in methylene chloride (10 ml) and stirred at room temperature and a 40% aqueous solution of methylamine (5 ml) added. The reactants were stirred together for 0.5 h at room temperature and the layers separated. The aqueous layer was extracted with methylene chloride (2×10 ml) and the combined methylene chloride layers dried over powdered potassium carbonate. After filtration and evaporation of solvents, the crude product was isolated as a thick yellow oil which was purified by chromatography on silica gel using a short column and an eluant of ethyl acetate and ethanol in the ratio (1:9 v/v) to give the product as a thick yellow oil. The yield was 42 mg (59.8%). FAB-MS: -calculated for $C_{20}H_{26}N_2O_2$ 326.2; found 327.3 (M+1).

Step G: (R)-α-[(2-Benzyloxycarbonylamino-2-methyl-1-oxypropyl)amino]-N-methyl-N-[[(2'-(t-butoxycarbonylaminomethyl))-[1,1'-biphenyl]-4-yl]methyl]benzenebutanamide The acid (24.5 mg; 0.06 mmol) prepared in Step D and amine (20 mg; 0.06 mmol) were dissolved in dry methylene chloride and triethylamine (17 ml; 0.12 mmol) was added. This mixture was stirred at room temperature and BOP was added in a single portion. The reaction mixture was stirred and maintained at room temperature overnight then worked up as follows. The reaction was diluted with brine (5 ml) and extracted with methylene chloride (4×10 ml). The combined methylene chloride extracts were dried over powdered anhydrous magnesium sulfate, filtered and evaporated under reduced pressure using a rotorvapor. The resulting residues were subjected to column chromatography on silica gel using a solvent system of ethyl acetate and hexanes (55:45 v/v). The desired product was isolated as a thick oil (27.2 mg; 64.1%). FAB-MS:- calculated for $C_{42}H_{50}N_4O_6$ 706.4; found 707.6 (M+1).

Step H: (R)-α-[(2-Benzyloxycarbonylamino-2-methyl-1-oxypropyl)amino]-N-methyl-N-[[(2'-(aminomethyl))-1,1'-biphenyl]-4-yl]methyl]benzenebutanamide The product from Step G (27.2 mg; 0.038 mmol) of this Example was dissolved in dry methylene chloride (3 ml) and anisole (1 ml) added and stirred at room temperature. TFA (2 ml) was added in a single portion and the resulting homogeneous pale yellow solution stirred at room temperature for 1 h. The volatiles were removed under reduced pressure and the reduced residues dissolved in chloroform and washed with saturated aqueous sodium bicarbonate solution. The chloroform solution was dried over anhydrous potassium carbonate powder, filtered and the filtrates evaporated under reduced pressure to leave a mobile pale yellow liquid which was chromatographed on silica gel using a solvent gradient starting with ethyl acetate and hexanes (1:1 v/v), neat ethyl acetate then ethyl acetate and ethanol (9:1 v/v). The required amine product (18 mg; 78%) was isolated as a yellow oil. FAB-MS:- calculated for $C_{37}H_{42}N_4O_4$ 606.3; found 629.7 (M+Na).

Step I: (R)-α-[(2-Amino-2-methyl-1-oxypropyl)amino]-N-methyl-N-[[(2'-[[[(methylamino)carbonyl]amino]-methyl]-[1,1'-biphenyl]-4-yl]methyl]benzene-butanamide, trifluoroacetate The amine (18 mg; 0.030 mmol) from Step H of this Example was dissolved in dry methylene chloride (0.5 ml) and methyl isocyanate (30 ml; 0.051 mmol) added in a single portion. The reactants were stirred together overnight at room temperature, then the volatiles removed under reduced pressure using a rotary evaporator. The resulting residues were partially purified by chromatography on silica gel using a gradient of ethyl acetate and hexanes 4:1, neat ethyl acetate then ethyl acetate and ethanol (9:1 v/v). A yield of 14 mg of partially purified product was obtained. This material was dissolved in methanol (5 ml) and 30% palladium (11) hydroxide on carbon (5 mg) added. The methanol solution with catalyst was degassed and an hydrogen atmosphere introduced over the solution using a balloon. Hydrogenation at room temperature was maintained for 1.5 h and the reaction stopped. The suspended catalyst was removed by filtration through a Celite pad and the filtrate evaporated under reduced pressure to leave the crude product as a glassy solid. The material was stored overnight in the refrigerator and then purified by hplc using a C18 reversed phase column using a methanol and 0.1% aqueous trifluoroacetic acid solvent gradient. This gave the final compound as a glassy solid. The yield was 10.2 mg (52.8%). $^1$H NMR (400 MHz, CD$_3$OD): 1.62 (d, 3H) 1.63 (d, 3H) 2.07 (m, 2H) 2.50–2.85 (m, 2H), 2.66 (d, 3H), 2.89 (d, 3H) 4.19 (ABq, 2H) 4.45–4.85 (m, 3H) 7.10–7.45 (m, 13H). FAB-MS:- calculated for $C_{31}H_{39}N_5O_3$ 529.3; found 530 (M+1).

EXAMPLE 10

(R)-α-[(3-Amino-3-methyl-1-oxybutyl)amino]-N-methyl-N-[[(2'-[([methylaminolcarbonyl)aminomethyl])-[1,1'-biphenyl]-4-yl]methyl] benzenebutanamide, trifluoroacetate Step A: (R)-α-[(3-Benzyloxycarbonylamino-3-methyl-1-oxobutyl)amino]benzenebutanoic acid allyl ester D-Homophenylalanine allyl ester (350 mg; 1.60 mmol), triethylamine (445 µl; 3.19 mmol) and 3-t-butoxycarbonylamino-3-methylbutanoic acid (412.8 mg; 1.64 mmol) were dissolved in dry methylene chloride (3 ml) and stirred at room temperature to give a homogeneous solution. BOP was added to the solution over 5 minutes and the reaction mixture stirred together at room temperature for 12 h. The reaction mixture was quenched by adding brine (10 ml) directly to the reaction. The crude products were isolated by extraction with methylene chloride (2×25 ml); the combined methylene chloride extracts dried with powdered anhydrous magnesium sulfate, filtered and evaporated under reduced pressure. The pale yellow oil thus obtained was subjected to column chromatography on silica gel using an eluant of ethyl acetate and hexanes (1:1 v/v). In this way, 432 mg (59.7%) of the desired product was isolated as a colorless oil. FAB-MS: -calculated for $C_{26}H_{32}N_2O_5$ 452.2; found 453.4 (M+1).

Step B: (R)-α-[(3-Benzyloxycarbonylamino-3-methyl-1-oxobutyl)amino]benzenebutanoic acid The allyl ester (120 mg; 0.27 mmol) was dissolved in dry methylene chloride and triphenylphosphine (3 mg) and tetrakis(triphenylphosphine)palladium(0) (3 mg) were added under nitrogen. The mixture was stirred at room temperature and a solution of 2-methylhexanoic acid potassium salt (0.5M in ethyl acetate) (0.58 ml) added. The reaction mixture was stirred at room temperature for 16 h and the volatiles were removed on a rotorvapor. The oil that remained was subjected to column chromatography on silica gel using a solvent gradient comprising initially ethyl acetate and hexanes (2:1 v/v), neat ethyl acetate, then ethyl acetate and ethanol (1:9 v/v). The material (52.3 mg) was substantially the desired product contaminated with a small amount of 2-methylhexanoic acid potassium salt. FAB-MS: -calculated for $C_{23}H_{28}N_2O_5$ 412.2; found 435.2 (M+Na).

Step C: 4-[(N-Methylamino)methyl]-2'(t-butoxycarbonylaminomethyl)-1,1'-biphenyl

The urethane (250 mg; 0.8 mmol) from Step B of this Example and triethylamine (139 µl; 1.00 mmol) were dissolved in dry methylene chloride (2 ml) and added to a solution of methanesulfonyl chloride (77.3 µl; mmol) in dry methylene chloride (1.5 ml) at room temperature over 2.5 minutes. The resulting homogeneous solution was stirred at room temperature for a further 3 h and then a 40% aqueous methylamine solution added in a single portion. The two phase reaction was vigorously stirred together for 0.5 h and then extracted with methylene chloride (4×15 ml). The combined methylene chloride extracts were dried over anhydrous potassium carbonate powder, filtered and evaporated under reduced pressure to leave a thick oil. The oil was purified by a short column chromatography on silica gel using first a mixture of ethyl acetate and hexanes (2:1 v/v) and then with a mixture of ethyl acetate and methanol (4:1 v/v ). In this way, 216 mg (82.7%) of a pale yellow oil was obtained which was the desired product for which satisfactory analytical data were obtained.

Step D: (R)-α-[(3-Benzyloxycarbonylamino-3-methyl-1-oxybutyl)amino]-N-methyl-N-[[(2'-(t-butoxycarbonylaminomethyl))-[1,1'-biphenyl]-4-yl]methyl]benzenebutanamide The acid (25.3 mg; 0.06 mmol) obtained in Step B and the amine (20 mg; 0.19 mmol) in Step C of this Example and triethylamine (17 µl; 0.12 mmol) were dissolved in dry methylene chloride (1 ml). BOP (85 mg; 0.19 mmol) was added in a single batch and the reaction mixture stirred at room temperature overnight. Saturated brine (5 ml) was added to quench the reaction and the products isolated by extraction with methylene chloride (4×10 ml). The combined methylene chloride extracts were dried over powdered anhydrous magnesium sulfate and filtered. Removal of volatiles from the methylene chloride solution under reduced pressure gave a yellow oil which was purified by column chromatography on silica gel using a solvent mixture of ethyl acetate and hexanes in the ratio (55:45 v/v). The product (24.3 mg; 64.5%) was isolated as a colorless oil. FAB-MS:- calculated for $C_{43}H_{52}N_4O_6$ 720.4; found 721.8 (M+1).

Step E: (R)-α-[(3-Benzyloxycarbonylamino-3-methyl-1-oxybutyl)amino]-N-methyl-N-[[(2'-(aminomethyl))-[1,1'-biphenyl]-4-yl]methyl]benzenebutanamide The product from Step D (24.3 mg; 0.06 mmol) of this example was dissolved in dry methylene chloride (3 m) and anisole (1 ml) added. The resulting homogeneous solution was rapidly stirred at room temperature and TFA (2 ml) added and the reaction mixture turned yellow. The reaction was stirred at room temperature for 2.5 h and then the volatiles removed under reduced pressure to give a oil. The residues were dissolved in chloroform, washed with saturated aqueous sodium bicarbonate solution and the chloroform layer dried over anhydrous potassium carbonate powder. Evaporation of the volatiles afforded a pale yellow oil that was subsequently purified by column chromatography on silica gel using a solvent gradient of ethyl acetate and hexanes (1:1 v/v) then neat ethyl acetate and finally with ethyl acetate and ethanol (9:1 v/v). This gave an almost colorless oil which was the required product amine (15mg; 40.2%). FAB-MS: -calculated for $C_{38}H_{44}N_4O_4$ 620.3; found 621.2 (M+1).

Step F: (R)-α-[(3-Amino-3-methyl-1-oxybutyl)amino]-N-methyl-N-[[(2'-[[[(methylamino)carbonyl]amino]methyl]-[1,1'-biphenyl]-4-yl]methyl]benzene-butanamide, trifluoroacetate The amine from Step E (15 mg; 0.024 mmol) of this Example was dissolved in dry methylene chloride (0.5 ml) and methyl isocyanate (30 µl; 0.51 mmol) was added to the amine in a single portion. The reaction mixture was stirred at room temperature overnight and then the volatiles removed under reduced pressure on a rotorvapor. The residues were then chromatographed on silica gel using a solvent gradient of ethyl acetate and hexanes (4:1 v/v), neat ethyl acetate and then ethyl acetate and ethanol (9:1 v/v). The combined product fractions were evaporated to leave a thick oil (12 mg) which was substantially the expected methyl urea. This urea product was hydrogenated in methanol (5 ml) in the presence of a suspension of 30% palladium (II) hydroxide on carbon (5 mg) using a balloon to introduce a hydrogen atmosphere for 1.5 h. The spent catalyst was removed by filtration of the hydrogenation reaction mixture through a Celite pad, the pad being carefully washed with methanol. Evaporation of the volatiles under reduced pressure afforded a glassy solid. This glass was stored overnight in the refrigerator and then purified by hplc on a C18 reversed phase column using a solvent gradient comprising methanol and 0.1% aqueous trifluoroacetic acid. In this way, 8.1 mg (51.3%) of a glassy solid was obtained which was the desired product. $^1$H NMR (400 MHz, CD$_3$OD): 1.38 (d, 3H) 1.39 (d, 3H) 2.01 (m, 2H) 2.50 and 2.57 (2×s, 2H), 2.50–2.85 (m, 2H) 2.66 (d, 3H) 2.92 (s, 3H) 4.20 (m, 2H) 4.45–4.85 (complex, 3H), 7.10–7.45 (m, 13H). FAB-MS:- calculated for C$_{32}$H$_{42}$N$_5$O$_3$ 543.3; found 544 (M+1).

EXAMPLE 11

(R)-α-[(4-Amino-4-methyl-1-oxopentyl)amino]-N-methyl-N-[[2'-(1H-tetrazol-5-yl)[1,1'-biphenyl]-4-yl]methyl]benzenebutan amide, trifluoroacetate Step A: 2,2-Dimethylpentanedioic acid, 5-methyl ester 2,2-Dimethylglutaric acid (10 g, 62.5 mmol) was dissolved in methanol (100 ml) and cooled to approximately 0° C. using an iced water bath and sulfuric acid (1 ml) was added drop by drop. The reaction mixture was stirred at 0° C. for 2 h and then the homogeneous solution stored for 14 h in the refrigerator. The volatiles were removed under reduced pressure with a rotary evaporator to leave a mobile liquid which was treated with an aqueous solution of potassium carbonate (20 g of potassium carbonate in 150 ml of water). The emulsion was shaken with two portions of hexanes to remove the dimethyl ester and the remaining aqueous solution was carefully acidified with ice-cold 6N hydrochloric acid until the acidity was around pH=2. This acidic aqueous solution was extracted with ether (3×150 ml) and the combined ethereal layers dried over anhydrous magnesium sulfate powder. Filtration of the ethereal solution followed by evaporation of solvent gave 10.5 g (96.5%) of a colorless mobile liquid which was the title mono methyl ester. FAB-MS:- calculated for C$_8$H$_{14}$O$_4$ 174; found 143 (M-MeO).

Step B: 4-(Benzyloxycarbonylamino)-4-methyl-pentanoic acid methyl ester

The monoester from Step A (4.5 g, 25.8 mmol) of this Example and triethylamine (5.3 ml; 38.0 mmol) were dissolved in toluene (50 ml) and chilled in an iced-water bath and diphenylphosphoryl azide (7.82 ml; 36.3 mmol) added. The solution turned yellow and the reaction mixture was warmed to reflux and maintained at reflux for 8 h during which gas evolution was observed. The reaction mixture was cooled to room temperature and dry benzyl alcohol (6.7 ml; 72.6 mmol) added. The reaction mixture was heated to reflux and maintained at reflux for 18 h. The flask was cooled and the products partitioned between diethyl ether (50 ml) and brine (50 ml). The ether layer was separated and washed with saturated aqueous sodium bicarbonate solution (50 ml) then dried over anhydrous powdered magnesium sulfate. After filtration, the ethereal filtrates were evaporated on a rotary evaporator under reduced pressure. The residues were stored overnight and then chromatographed on silica gel using a solvent system comprising ethyl acetate and hexanes 1:4 v/v. This gave 3.6 g (ca. 50%) benzyl carbamate that contained traces of benzyl alcohol. FAB-MS:- calculated for C$_{15}$H$_{21}$NO$_4$ 279.1; found 280.0 (M+1).

Step C: 4-(Benzyloxycarbonylamino)-4-methyl-pentanoic acid

A solution of the methyl ester (3.5 g; 12.53 mmol) [prepared in Step B of this Example] in methanol (5 ml) was stirred at room temperature and 2N aqueous sodium hydroxide solution (5 ml) added and stirred together for 24 h. The methanol was removed under reduced pressure and the remaining slightly opaque aqueous layer was washed with hexanes (3×25 ml) then acidified to pH=2 using an ice cold solution of 6N hydrochloric acid. The resulting white emulsion was extracted with methylene chloride (3×30 ml) and the combined extracts dried over magnesium sulfate, filtered and evaporated under reduced pressure. The residue 3.2 g (ca 95%) was substantially the title compound containing traces of benzyl alcohol. FAB-MS:- calculated for C$_{14}$H$_{19}$NO$_4$ 265.1; found 266.0 (M+1).

Step D: (R)-α-[(4-Benzyloxycarbonylamino-4-methyl-1-oxopentyl)amino]benzenebutanoic acid allyl ester D-Homophenylalanine allyl ester (175 mg; 0.80 mmol) (see Example 9, Step B), triethylamine (222 μl; 1.59 mmol) were dissolved in dry methylene chloride (2 ml) and 4-(benzyloxycarbonylamino)-4-methyl-pentanoic acid (211 mg; 0.80 mmol) added. The solution was stirred at room temperature and BOP (353 mg; 0.80 mmol) was added over 5 minutes, and this reaction mixture stirred at room temperature for 17 h. The reaction was quenched by adding brine and then the products of the reaction isolated by extraction with methylene chloride (3×15 ml). The methylene chloride layers were combined and dried with anhydrous magnesium sulfate powder, filtered and evaporated under reduced pressure. A thick golden yellow gum was obtained which was purified by column chromatography on silica gel using ethyl acetate and hexanes 1:2 v/v. The product (182 mg; 48.9%) was isolated as a pale yellow gum. FAB-MS:- calculated for C$_{27}$H$_{34}$N$_2$O$_5$ 466.3; found 467.7 (M+1).

Step E: (R)-α-[(4-Benzyloxycarbonylamino-4-methyl-1-oxopentyl)amino]benzenebutanoic acid The allyl ester (180 mg; 0.385 mmol) from Step D and tetrakis(triphenylphosphine)palladium(0) (12.0 mg) were dissolved together in dry methylene chloride and stirred at room temperature and a solution of 2-methylhexanoic acid potassium salt (0.5M in ethyl acetate) (0.96 ml) added under nitrogen to the ester. The reaction mixture was stirred at room temperature for 72 h and then the volatiles removed on a rotary evaporator to leave a thick gum. The gum was dissolved in the minimum volume of methylene chloride and subjected to column chromatography on silica gel ethyl acetate then ethyl acetate and ethanol 9:1 v/v. The desired product (138.4 mg; 84.2%) was isolated as a colorless glass. FAB-MS:- calculated for C$_{24}$H$_{30}$N$_2$O$_5$ 426.2; found 465.2 (M+K).

Step F: N-Triphenylmethyl-5-[2-(4'-N-methylamino)methyl]biphen-4-yl)tetrazole

N-Triphenylmethyl-5-[2-(4'-[bromomethyl]-biphen-4-yl) tetrazole (500 mg; 0.90 mmol) was dissolved in methylene chloride (5 ml) and a solution of 40% aqueous methylamine (5 ml) added. The two phase system was stirred vigorously for 2 h at room temperature and then the layers separated and the aqueous layer discarded and the methylene chloride layer dried over powdered anhydrous potassium carbonate, filtered and evaporated under reduced pressure. This afforded a thick yellow oil which was chromatographed on a short column of silica a gel using first a solvent mixture of ethyl acetate and hexanes in the ratio of 2:1 v/v and then with neat methanol. The product was isolated as a white solid (414.3 mg; 91%).

Step G: (R)-α-[(4-Benzyloxycarbonylamino-4-methyl-1-oxopentyl)amino]-N-methyl-N-[[2'-(N-triphenylmethyltetrazol-5-yl)[1,1'-biphenyl]-4-yl]methyl]-benzenebutanamide The acid (30 mg; 0.07 mmol) from Step E of this Example, amine (35.7 mg; 0.07 mmol) from Step F and triethylamine (20 μl; 0.14 mmol) were dissolved in dry methylene chloride (1 ml) and stirred at room temperature.

BOP reagent (31.1 mg; 0.07 mmol) was added and the reaction mixture stirred overnight at room temperature. The reaction was quenched by adding brine (5 ml) and extracted with methylene chloride (3×10 ml). The combined methylene chloride layers were dried over anhydrous magnesium sulfate powder, filtered and evaporated under reduced pressure to give a brown gum. Column chromatography of the gum on silica gel using an eluant comprising ethyl acetate and hexanes 2:1 v/v. The product (35.8 mg; 55.6%) was isolated as an almost colorless glassy solid. FAB-MS:- calculated for $C_{58}H_{57}N_7O_4$ 915.4; found 922.9(M+Li).

Step H: (R)-α-[(4-Amino-4-methyl-1-oxopentyl)amino]-N-methyl-N-[[2'-(1H-tetrazol-5-yl)[1,1'-biphenyl]-4-yl]methyl]benzenebutanamide, trifluoroacetate The product from Step G (32 mg; 0.034 mmol) of this Example was dissolved in methanol (5 ml) and the hydrogenation catalyst, 30%-palladium (II) hydroxide on carbon (5 mg) was added. The solution was degassed using an aspirator vacuum and then an hydrogen atmosphere introduced over the reaction solvent using a balloon. Hydrogenation was maintained for 3 h and then the reaction mixture filtered through a Celite pad to remove the spent palladium catalyst. The filtrates were evaporated to give a white solid which was futher purified by reversed phase hplc using a C18 column using a methanol and 0.1% aqueous trifluoroacetic acid solvent gradient. In this way, 18.1 mg (81.5%) of the desired final product was obtained. $^1$H NMR (400 MHz, $CD_3OD$):

$^1$H NMR (400 MHz, $CD_3OD$): 1.33 (dd, 6H) 1.96–2.90 (m, 8H) 2.84 (d, 3H) 4.30–4.47 and 4.62–4.80 (m, 3H) 7.05–7.33 and 7.52–7.73 (m, 13H). FAB-MS:- calculated for $C_{31}H_{37}N_7O_2$ 539.3; found 540.7 (M+1).

EXAMPLE 12

(R)-α-[(4-Amino-4-methyl-1-oxypentyl)amino]-N-methyl-N-[[(2'-[[[(methylamino)carbonyl]amino]methyl]-[1,1'-biphenyl]-4-yl]methyl]benzenebutanamide, trifluoroacetate Step A: (R)-α-[(4-t-Butoxycarbonylamino-4-methyl-1-oxypentyl)amino]-N-methyl-N-[[(2'-(t-butoxycarbonylaminomethyl))-[1,1'-biphenyl]-4-yl]methyl]-benzenebutanamide The acid (41 mg; 0.096 mmol) from Step E of Example 11, triethylamine (27 μl; 0.194 mmol) and amine (31.4 mg; 0.096 mmol) from Step C, Example 10 were dissolved in dry methylene chloride (1 ml). BOP reagent (42.5 mg; 0.096 mmol) was added in a single portion and the reactants stirred at room temperature overnight. The reaction was quenched by addition of brine (5 ml) and then extracted with methylene chloride (3×10 ml). The methylene chloride solution was dried with anhydrous magnesium sulfate and filtered. The filtrates were evaporated under reduced pressure to remove the volatiles to leave a golden yellow gum which was chromatographed on silica gel using ethyl acetate and hexanes (1:2 v/v) as eluant. A yield of 31.7 mg (45%) of the desired product was obtained as a pale yellow oil. FAB-MS:- calculated for $C_{44}H_{54}N_4O_6$ 734.4; found 735.7 (M+1).

Step B: (R)-α-[(4-Amino-4-methyl-1-oxypentyl)amino]-N-methyl-N-[[(2'-aminomethyl)-[1,1'-biphenyl]-4-yl]methyl]benzenebutanamide The carbamate (30 mg; 0.041 mmol) whose preparation was described in Step A of this Example was dissolved in dry methylene chloride (1.5 ml) and anisole (0.5 ml) added. The resulting solution was stirred at room temperature and TFA (0.5 ml) was added to the carbamate solution. After 1 h, the volatiles were removed under reduced pressure and the residues chromatographed using a short column of silica gel using a solvent gradient of ethyl acetate and hexanes 1:1 v/v then neat ethyl acetate and finally neat ethanol. The product (22.4 mg, 86%) was isolated as an oily solid. FAB-MS:- calculated for $C_{39}H_{46}N_4O_6$ 634.4; found 642.9 (M+Li).

Step C: (R)-α-[(4-Benzyloxycarbonylamino-4-methyl-1-oxypentyl)amino]-N-methyl-N-[[(2'-[[[(methylamino)carbonyl]amino]methyl]-[1,1'-biphenyl]-4-yl]methyl] benzenebutanamide The amine product (20 mg; 0.031 mmol) from Step B was dissolved in dry methylene chloride and stirred at room temperature and methyl isocyanate (100 μl; 1.70 mmol) added to the amine in a single portion. The reaction mixture was stirred at room temperature overnight and the volatiles removed under reduced pressure and the residues subjected to column chromatography on silica gel using ethyl acetate and methanol 95:5 v/v as eluant. In this way, the urea was obtained as a glass (17.8mg; 83%). FAB-MS:- calculated for $C_{41}H_{49}N_5O_5$ 691.4; found 692 (M+1).

Step D: (R)-α-[(4-Amino-4-methyl-1-oxypentyl)amino]-N-methyl-N-[[(2'-[[[(methylamino)carbonyl]amino]-methyl]-[1,1'-biphenyl]-4-yl]methyl]-benzenebutanamide, trifluoroacetate The urea (17.2 mg; 0.025 mmol) was dissolved in methanol (5 ml) and the hydrogenation catalyst 30%-palladium (II) hydroxide on carbon (5 mg) added to the methanol solution. The solution was stirred and degassed and then an hydrogen atmosphere introduced over the reaction mixture using a balloon for 3 h. After this time, the catalyst was removed by filtration through a celite bed, the bed carefully washed with methanol and then the filtrates were evaporated under reduced pressure to obtain a glassy solid. The solid was further purified by hplc on a C18 reversed phase column using a solvent gradient of methanol and 0.1% aqueous trifluoroacetic acid. The title compound (11.4 mg; 68.3%) was obtained as a glass.

$^1$H NMR (400 MHz, $CD_3OD$): 1.34 (d, 6H) 1.97 to 2.85 (m, 8H) 2.67 (d, 3H) 2.89 (d, 3H) 4.20 (m, 2H) 4.35–4.85 (m, 3H) 7.10–7.45 (m, 13H). FAB-MS:- calculated for $C_{33}H_{43}N_5O_3$ 557.3; found 558.7 (M+1).

EXPERIMENT 13

(R)-α-[(2-Amino-2-methyl-1-oxopropyl)amino]-N-methyl-N-[[2'-(1H-tetrazol-5-yl)[1,1'-biphenyl]-4-yl]methyl]-1H-indole-3-propanamide, trifluoroacetate Step A: (R)-α-[(2-t-Butoxycarbonylamino-2-methyl-1-oxopropyl)amino]-N-methyl-N-[[2'-N-triphenylmethyltetrazol-5-yl)[1,1'-biphenyl]-4-yl]methyl]-1H-indole-3-propanamide The acid (97 mg; 0.249 mmol) from Example 6, Step D, triethylamine (90 μl; 0.646 mmol) and amine (110 mg; 0.217 mmol) from Example 11, Step F were dissolved in dry methylene chloride to give a yellow solution. BOP reagent (144 mg; 0.326 mmol) was added and this reaction mixture stirred overnight and then the volatiles removed under reduced pressure. The resulting residues were chromatographed on silica gel using ethyl acetate and hexanes 7:3 v/v and the product was isolated as an off white solid. The yield was (67.3 mg; 30.7%). FAB-MS:- calculated for $C_{54}H_{54}N_8O_4$ 878.4; found 879.4 (M+1).

Step B: (R)-α-[(2-Amino-2-methyl-1-oxopropyl)amino]-N-methyl-N-[[2'-(1H-tetrazol-5-yl)[1,1'-biphenyl]-4-yl]methyl]-1H-indole-3-propanamide, trifluoroacetate The product from Step A (30 mg; 0.034 mmol) of this Example was dissolved in methanol (1.5 ml) and added to a solution comprising 9N-hydrochloric acid (0.5 ml) and methanol (0.5 ml) with vigorous stirring at room temperature. After 2 h, the solvent was removed overnight using a stream of nitrogen gas. The solid material that remained was carefully purified by hplc on a C18 reversed phase column using a solvent gradient of methanol and 0.1% aqueous trifluoroacetic acid. The product was isolated as a pale off white amorphous solid. The yield was 19.8 mg (89 %). $^1$H NMR (400 MHz, CD$_3$OD): 1.50 (d, 3H) and 1.55 (d, 3H) 2.71 (s, 3H) 3.13–3.35 (m, 2H) 4.13–4.47 (m, 2H) 5.21 (m, 1H) 6.84–7.72 (m, 13H). FAB-MS:- calculated for C$_{30}$H$_{32}$N$_8$O$_2$ 536.2; found 537.0 (M+1).

EXAMPLE 14

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]1H-indole-3-propanamide, trifluoroacetate Step A: N-(t-Butoxycarbonyl)-D-tryptophan Allyl Ester N-(t-Butoxycarbonyl)-D-tryptophan (3 g; 9.868 mmol) was dissolved in acetone and an aqueous solution of potassium carbonate (2.84 g; 20.58 mmol) added followed by allyl bromide (1.55 g; 12.81 mmol). The reaction mixture was stirred for 18 h and then the acetone was substantially removed by evaporation under reduced pressure. The oily water layer that remained was acidified to approximately pH=5 with 1N-hydrochloric acid and then extracted with methylene chloride. The methylene chloride layer was dried over anhydrous magnesium sulfate powder, filtered and evaporated under reduced pressure to give a foamy solid. The foam was further purified by column chromatography using silica gel and ethyl acetate and hexanes 2:1 v/v as eluant. In this manner, a 1.92 g yield (56%) of the desired product was obtained as an off white solid. FAB-MS:- calculated for C$_{19}$H$_{24}$N$_2$O$_4$ 344; found 344 (M).

Step B: D-Tryptophan Allyl Ester

The allyl ester (1.92 g, 5.58 mmol) from Step A and anisole (3 ml) were dissolved in anhydrous methylene chloride (10 ml) and stirred at room temperature. Trifluoroacetic acid (5 ml) was added and the resulting solution stirred at room temperature for 2 h. After this period of stirring, the volatiles were removed under reduced pressure and the residues redissolved in pure methylene chloride and washed with a solution of saturated aqueous sodium carbonate. The methylene chloride layer was dried, filtered and evaporated under reduced pressure to give a golden yellow mobile liquid which was chromatographed on silica gel using a solvent gradient starting with ethyl acetate and hexanes 1:1 v/v and increasing polarity to neat ethyl acetate then finally ethyl acetate and ethanol 9;1 v/v. The product (1.12 g, 66%) was isolated as an oil. FAB-MS:- calculated for C$_{14}$H$_{16}$N$_2$O$_2$ 244; found 245 (M+1).

Step C: (R)-α-[(2-Benzyloxycarbonylamino-2-methyl-1-oxopropyl)amino]-1H-indole-3-propanoic acid, allyl ester D-Tryptophan allyl ester (250 mg; 0.822 mmol), triethylamine (230 μl; 1.650 mmol) and N-benzyloxycarbonyl-α-methylalanine (167.9 mg; 0.826 mmol) were dissolved in dry methylene chloride (5 ml) and BOP (363.7 mg; 0.822 mmol) added. The reaction mixture was stirred at room temperature for 16 h and then the reaction quenched with saturated brine (5 ml). The methylene chloride layer was separated, dried with magnesium sulfate and filtered then the volatiles removed under reduced pressure to leave a dark brown oil. Chromatography of this oil on silica gel using ethyl acetate and hexanes 2:1 v/v afforded 322 mg (84.5%) of the desired product. FAB-MS:- calculated for C$_{26}$H$_{29}$N$_3$O$_5$ 463.2; found 464.5 (M+1).

Step D: (R)-α-[(2-Benzyloxycarbonylamino-2-methyl-1-oxopropyl)amino]-1H-indole-3-propanoic acid The allyl ester (200 mg; 0.43 mmol) whose preparation was described in Step C of this Example was dissolved in anhydrous methylene chloride and triphenylphosphine (3 mg) and tetrakis(triphenylphosphine)palladium(0) (6 mg) added. The solution was stirred at room temperature and then a solution of 2-methylhexanoic acid potassium salt added (0.95 ml). The reaction mixture was stirred for 3 days under nitrogen at room temperature and then the volatiles removed under reduced pressure. Chromatography of the residues on silica gel using a solvent gradient starting with ethyl acetate and hexanes 2:1 v/v then neat ethyl acetate followed by ethyl acetate and ethanol 19:1 v/v gave the desired product (Yield: 94.2 mg; 51.8%). FAB-MS:- calculated for C$_{22}$H$_{25}$N$_3$O$_5$ 423.2; found 462.4 (M+K).

Step E: (R)-α-[(2-Benzyloxycarbonylamino-2-methyl-1-oxopropyl)amino]-N-methyl-N-[[(2'-((t-butoxy-carbonyl)aminomethyl))-[1,1'-biphenyl]-4-yl]methyl]1H-indole-3-propanamide The acid (89 mg; 0.23 mmol) from Step E, triethylamine (96 μl; 0.69 mmol) and the amine (75 mg; 0.23 mol) prepared in Example 9, Step F were dissolved in dry methylene chloride and BOP (152.5 mg; 0.34 mmol) reagent was added. The reaction mixture was stirred for 21 h at room temperature and the volatiles removed under reduced pressure. The residues thus obtained were purified by column chromatography on silica gel using an eluant comprising ethyl acetate and hexanes 3:1 v/v. In this way, 135 mg (80%) of the desired product was obtained. FAB-MS:- calculated for C$_{43}$H$_{51}$N$_5$O$_6$ 733.4; found 755.3 (M+Na).

Step F: (R)-α-[(2-Benzyloxycarbonylamino-2-methyl-1-oxopropyl)amino]-N-methyl-N-[[(2'-(aminomethyl))-[1,1'-biphenyl]-4-yl]methyl]-1H-indole-3-propanamide The amide (130 mg; 0.18 mmol) from Step E was dissolved in methanol (5 ml) and added to 9N hydrochloric acid (2.5 ml) with vigorous stirring. After stirring for 3 h, the volatiles were removed under reduced pressure. The aqueous phase that remained was partitioned between saturated aqueous sodium carbonate solution and methylene chloride. The organic phase was separated, dried over potassium carbonate, filtered and evaporated under reduced pressure to give the product as a pale yellow oil. The yield was 102 mg (89.7%) FAB-MS:- calculated for C$_{38}$H$_{41}$N$_5$O$_4$ 631.3; found 632 (M+1).

Step G: (R)-α-[(2-Benzyloxycarbonylamino-2-methyl-1-oxopropyl)amino]-N-methyl-N-[[(2'-((methylamino)carbonyl)-aminomethyl))-[1,1'-biphenyl]-4-yl]methyl]1H-indole-3-propanamide The amine (60 mg; 0.095 mmol) from Step F were mixed together with methyl isocyanate (50 μl; 0.848 mmol) in dry methylene chloride (1 ml). The reaction mixture was stirred at room temperature overnight and the volatiles were removed under reduced pressure. The residues were chromatographed on silica gel using a solvent mixture of ethyl acetate and methanol 19:1 v/v. This afforded 57 mg (ca. 85%) of the product which was substantially the required compound.

Step H: (R)-α-[(2-Amino-2-methyl-1-oxopropyl)amino]-N-methyl-N-[[(2'-[[[(methylamino)carbonyl]amino]methyl]-[1,1'-biphenyl]-4-yl]methyl]-1H-indole-3-propanamide, trifluoroacetate The urea (50 mg; 0.073 mmol) from Step G was dissolved in methanol and hydrogenation catalyst, 10% palladium (II) hydroxide on carbon (20 mg) was added and then degassed. A hydrogen atmosphere was introduced over the reaction mixture with the aid of a balloon and after 4.5 h the reaction halted. The catalyst was removed by filtration through a Celite bed and the bed carefully washed with more methanol. The filtrates were evaporated under reduced pressure and the residues further purified by HPLC on a reversed phase C18 column using a solvent gradient of methanol and 0.1% aqueous trifluoroacetic acid. The mass of the title compound was 33.2 mg (68.5%) which was isolated as a glass.

$^1$H NMR (400 MHz, CD$_3$OD): 1.48 and 1.55 (2×d, 6H) 2.66 (d, 3H) 2.75 and 2.80 (2×s, 3H) 3.10–3.40 (m, 2H) 4.15–4.55 (m, 4H) 5.27 (m, 1H) 6.90–7.65 (m, 13H). FAB-MS:- calculated for C$_{32}$H$_{38}$N$_6$O$_3$ 554.3; found 555.1 (M+1).

EXPERIMENT 15

(R)-α-[(3-Amino-3-methyl-1-oxobutyl)amino]-N-[[2'-[[(methylamino)carbonyl]amino][1,1'-biphenyl]-4-yl]-methyl]-1H-indole-3-propanamide, trifluoroacetate Step A: (R)-α-[(3-t-Butoxycarbonylamino-3-methyl-1-oxobutyl)amino]-1-H-indole-3-propanoic acid benzyl ester Prepared from D-tryptophan benzyl ester (1 g; 3.40 mmol) and 3-t-butoxycarbonylamino-3-methylbutanoic acid (0.91 g; 4.19 mmol) by the procedure described in Example 6, Step C. The yield was 0.981 g (58%).

$^1$H NMR (400 MHz, CDCl$_3$): 1.24 (s, 3H) 1.26 (s, 3H) 1.37 (s, 9H) 2.46 (ABq, 2H) 3.24 (dt, 2H) 4.92 (q, 1H) 5.14 (q, 2H) 6.81 (d, 1H) 7.18 (t, 1H) 7.15–7.35 (m, 7H) 7.5 (d, 1H).

Step B: (R)-α-[(3-t-Butoxycarbonylamino-3-methyl-1-oxobutyl)amino]-1-H-indole-3-propanoic acid The ester (0.98 g; 1.98 mmol) prepared in Step A of this Example was hydrogenated according to the procedure described in Example 6, Step D. The yield of the acid was 0.86 g and used without further purification.

Step C: (R)-α-[(3-t-Butoxycarbonylamino-3-methyl-1-oxobutyl)amino]-N-[[(2'-nitro)[1,1'-biphenyl]-4-yl]methyl]-1H-indole-3-propanamide The acid (345 mg; 0.855 mmol) prepared in Step B of this Example and 4-aminomethyl-2'-nitro-1,1'-biphenyl (200 mg; 0.876 mmol) whose preparation was described in Example 6, Step H was converted into the desired product using the procedure desribed in Example 6, Step I. This gave 155 mg (29.5%) of (R)-α-[3-(t-butoxycarbonylamino-3-methyl-1-oxobutyl)amino]-N-[[(2'-nitro)[1,1'-biphenyl]-4-yl]methyl]-1H-indole-3-propanamide.

$^1$H NMR (400 MHz, CD$_3$OD): 1.24 (s, 3H) 1.26 (s, 3H) 1.38 (s, 9H) 2.50 (ABq, 2H) 3.13 (dd, 1H) 3.24 (dd, 1H) 4.28 (ABq, 2H) 4.68 (t, 1H) 6.97–7.17 (m, 7H) 7.33 (d, 1H) 7.42 (d, 1H) 7.52 (t, 1H) 7.64 (m, 2H) 7.82 (d, 1H).

Step D: (R)-α-[(3-t-Butoxycarbonylamino-3-methyl-1-oxobutyl)amino]-N-[[(2'-amino)[1,1'-biphenyl]-4-yl]methyl]-1H-indole-3-propanamide The nitro compound (150 mg; 0.244 mmol) obtained in Step D above was hydrogenated in ethanol (5 ml) using 5%-platinum on carbon using a balloon as described above in Example 6, Step J. In this way, 124 mg (87%) yield of the amine was obtained.

$^1$H NMR (400 MHz, CD$_3$OD): 1.23 (s, 3H) 1.25 (s, 3H) 1.38 (s, 9H) 2.5 (ABq, 2H) 3.13 (dd, 1H) 3.25 (dd 1H) 4.20 (dd, 1H) 4.34 (dd, 1H) 4.70 (m, 1H) 6.74 (t, 1H) 6.80 (d, 1H) 6.96–7.13 (m, 7H) 7.23 (d, 2H) 7.32 (d, 1H) 7.62 (d, 1H)

Step E: (R)-α-[(3-t-Butoxycarbonylamino-3-methyl-1-oxobutyl)amino]-N-[[(2'((methylamino)carbonyl)-amino)[1,1'-biphenyl]-4-yl]methyl]-1H-indole-3-propanamide The aniline (25 mg; 0.043 mmol) prepared in Step E was treated with methyl isocyanate (19 µl; 0.322 mmol) in dry methylene chloride (0.5 ml) as described above in Example 6, Step K. The urea (19.4 mg; 77.3%) was isolated as an off white solid after chromatography. FAB-MS:- calculated for C$_{36}$H$_{44}$N$_6$O$_5$ 640.4; found 641.5 (M+1).

Step F: (R)-α-[(3-Amino-3-methyl-1-oxobutyl)amino]-N-[[(2'((methylamino)carbonyl)amino)[1,1'-biphenyl]-4-yl]methyl]-1H-indole-3-propanamide, trifluoroacetate The urea (15.5 mg; 0.024 mmol) from Step F was dissolved in methanol (0.5 ml) and hexanes (0.5 ml) added. The solution was stirred at room temperature vigorously and 9N-hydrochloric acid (0.5 ml) added. The reaction mixture was stirred at room temperature for 1 h and the hexanes layer removed using a Pasteur pipette and discarded. The remaining aqueous methanol layer was evaporated using a stream of nitrogen gas overnight. A solid residue remained and was further purified by mplc on a C8 reversed phase column using a solvent mixture comprising methanol and 0.1% aqueous trifluoroacetic acid in the ratio 75:25. A 12.7 mg (80%) yield of an off white solid was obtained of the desired product.

$^1$H NMR (400 MHz, CD$_3$OD): 1.15 (s, 3H), 1.30 (s, 3H) 2.44 (ABq, 2H) 2.64 (d, 3H) 3.07–3.35 (m, 2H), 4.32 (m, 2H) 4.78 (t, 1H) 6.96–7.37 and 7.60–7.70 (m, 13H). FAB-MS:- calculated for C$_{31}$H$_{36}$N$_6$O$_3$ 540.3; found 541.9 (M+1).

EXAMPLE 16

(R)-α-[(2-Amino-2-methyl-1-oxopropyl)amino]-N-[[2'-[[(2-hydroxyethylamino)carbonyl]amino][1,1'-biphenyl]-4-yl]-methyl]-1H-indole-3-propanamide, trifluoroacetate Step A: (R)-α-[(2-t-Butoxycarbonylamino-2-methyl-1-oxopropyl)amino]-N-[[2'-[[(2-hydroxyethylamino)carbonyl]amino][1,1'-biphenyl]-4-yl]-methyl]-1H-indole-3-propanamide methacrylate ester The amine (25 mg; 0.044 mmol) described in Example 6, Step J was dissolved in dry methylene chloride (0.5 ml) and isocyanatoethyl methacrylate (9 µl; 0.058 mmol) was added and the reaction mixture stirred at room temperature overnight for 24 h. The volatiles were removed under reduced pressure on a rotary evaporator and the residues chromatographed on silica gel using a solvent mixture comprising ethyl acetate and hexanes 3:1 v/v. The product (25 mg; 78.3%) was isolated as an oil. FAB-MS:- calculated for C$_{40}$H$_{48}$N$_6$O$_7$ 724.4; found 725.5 (M+1).

Step B: (R)-α-[(2-Amino-2-methyl-1-oxopropyl)amino]-N-[[2'-[[(2-hydroxyethylamino)carbonyl]amino][1,1'-biphenyl]-4-yl]-methyl]-1H-indole-3-propanamide, trifluoroacetate The urea (23 mg; 0.033 mmol) from Step A was dissolved in methanol and a small amount of sodium methoxide solution (100 µl) [prepared from 1 ml of methanol and 23 mg of sodium] was added. The solution was stirred for 3 h at room temperature and then the reaction acidified with a cold 10% solution of hydrochloric acid and immediately extracted with methylene chloride. The extracts were dried with anhydrous magnesium sulfate powder, filtered and evaporated under reduced pressure. The products were dissolved in fresh methanol (0.5 ml) and hexanes (0.5 ml) then 9N-hydrochloric acid (0.5 ml) was added with stirring. After 1 h of stirring at room temperature, the hexanes layer was removed with the aid of a Pasteur pipette and discarded and the residues evaporated using a stream of nitrogen gas (21 mg). The product (14 mg; 76.3 %) was isolated on by mplc on a C8 reversed phase column using a solvent mixture of methanol and 0.1% aqueous trifluoroacetic acid (70:30 v/v).

$^1$H NMR (400 MHz, CD$_3$OD): 1.37 (s, 3H) 1.57 (s, 3H) 3.15–3.40 (m, 4H) 3.52 (m, 2H) 4.37 (m, 2H) 4.78 (t, 1H)

6.98–7.7 (m, 13H). FAB-MS:- calculated for $C_{31}H_{36}N_6O_4$ 556.3; found 557.8 (M+1).

EXAMPLE 17

(R)-α-[(3-Amino-3-methyl-1-oxobutyl)amino]-N-[[2'-[[(2-hydroxyethylamino)carbonyl]amino][1,1'-biphenyl]-4-yl]-methyl]-1H-indole-3-propanamide, trifluoroacetate Step A: (R)-α-[(3-Amino-3-methyl-1-oxobutyl)amino]-N-[[2'-[[(2-hydroxyethylamino)carbonyl]amino][1,1'-biphenyl]-4-yl]methyl]-1H-indole-3-propanamide, methacrylate ester The amine (20 mg; 0.034 mmol) from Example 15, Step D was dissolved in dry methylene chloride (0.5 ml) and isocyanatoethyl methacrylate (5.3 mg; 0.034 mmol) added. The resulting solution was stirred at room temperature for 24 h then the volatiles removed under reduced pressure and the residues chromatographed on silica gel using ethyl acetate and hexanes 4:1 v/v. This gave 17.6 mg (70%) of the desired product.

Step B: (R)-α-[(3-Amino-3-methyl-1-oxobutyl)amino]-N-[[2'-[[(2-hydroxyethylamino)carbonyl]amino][1,1'-biphenyl]-4-yl]methyl]-1H-indole-3-propanamide, trifluoroacetate The product from Step A (15 mg; 0.020 mmol) was dissolved in methanol (0.5 ml) and sodium methoxide solution (100 μl) [prepared from 1 ml of methanol and 23 mg of sodium] was added. The reaction mixture was stirred for 1.5 h at room temperature and then the reaction acidified with 5 drops of 2N-hydrochloric acid. The volatiles were removed under reduced pressure on a rotary evaporator and the residues were dissolved in methanol (0.5 ml) and hexanes (0.5 ml) added. The mixture was stirred at room temperature and anisole (5 μl) along with 9N-hydrochloric acid (0.5 ml) added. After stirring for 0.5 h, the hexanes layer was removed using a Pasteur pipette and discarded and the aqueous methanol removed using a fast stream of nitrogen gas. The whitish solid that was obtained was purified by mplc using a C8 reversed phase column and a solvent mixture of methanol and 0.1% aqueous trifluoroacetic acid in the ratio 85:15 v/v. A yield of 7.5 mg (55%) was obtained of the desired product.

$^1$H NMR (400 MHz, CD$_3$OD): 1.14 (s, 3H) 1.29 (s, 3H) 2.48 (ABq, 2H) 3.05–3.35 (m, 4H) 3.50 (m, 2H) 4.32 (m, 2H) 5.83 (t, 1H) 6.95–7.35 and 7.60–7.70 (m, 13H). FAB-MS:- calculated for $C_{32}H_{38}N_6O_4$ 570.3; found 571.8 (M+1).

EXAMPLE 18

(R)-α-[(2-Amino-2-methyl-1-oxypropyl)amino]-N-ethyl-N-[[2'-(1H-tetrazol-5-yl)-[1,1'-biphenyl]-4-yl]methyl]benzenebutanamide, trifluoroacetate Step A: N-Triphenylmethyl-5-[2-(4'-[(N-ethylamino)methyl]biphen-4-yl)tetrazole This amine was prepared in a similar manner to that of the N-methylamine anolog whose prepartion was described in Example 11, Step F. Starting with N-triphenylmethyl-5-[2-(4'-[bromomethyl]-biphen-4-yl)tetrazole (400 mg; 0.897 mmol) in methylene chloride (5 ml) and 70% aqueous ethylamine solution (5 ml). This afforded 2.266 g (48.5%) of the desired tetrazole amine product. FAB-MS:- calculated for $C_{35}H_{31}N_5$ 521.3; found 522.7 (M+1).

Step B: (R)-α-[(2-t-Butoxycarbonylamino-2-methyl-1-oxopropyl)amino]-N-ethyl-N-[[2'-(N-triphenylmethyl-tetrazol-5-yl)[1,1'-biphenyl]-4-yl]methyl]-benzenebutanamide (R)-α-[(2-t-Butoxycarbonylamino-2-methyl-1-oxopropyl)amino]-benzenebutanoic acid (115.5 mg; 0.317 mmol) whose preparation was described in Example 7, Step D and the tetrazole amine (110 mg; 0.211 mmol) from Step A of this Example were dissolved in methylene chloride (1 ml) then treated with triethylamine (73.5 μl; 0.528 mmol) and BOP reagent (186.8 mg; 0.422 mmol). The reaction mixture was stirred at room temperature for 72 h. The volatiles were removed under partial vacuum using a rotary evaporator and the products isolated by column chromatography on silica gel using as elevant a solvent mixture of ethyl acetate and hexanes (1:1 v/v). The product (188.2 mg; 68.4%) was isolated as a foamy white solid. FAB-MS:- calculated for $C_{54}H_{57}N_7O_4$ 867.4; found 874.4 (M+Li).

Step C: (R)-α-[(2-Amino-2-methyl-1-oxypropyl)amino]-N-ethyl-N-[[2'-(1H-tetrazol-5-yl)-[1,1'-biphenyl]-4-yl]methyl]benzenebutenamide, trifluoroacetate The amide product (145 mg; 0.167 mmol) from Step B of this Example was dissolved in methanol (2 ml) and was vigorously stirred at room temperature and 9N-hydrochloric acid added. After 2.5 h, hexanes (2 ml) was added, stirred imo the aqueous methanol layer for 10 minutes. The layers were then allowed to separate and the upper hexanes layer removed using a Pasteur pipette and discarded. The aqueous methanol layer was evaporated to dryness using a stream of nitrogen gas and the resulting residues purified by reversed phase hplc on a C18 column using a methanol and 0.1% aqueous TFA solvent gradient. The desired final product was isolated (72.4 mg; 67.8%) as a glass-like solid.

$^1$H NMR (400 MHz, CD$_3$OD): 1.00 (dd, 3H) 1.62 and 1.66 (2×d, 6H) 1.85–2.20 and 2.45–3.45 (m, 6H) 4.30 and 4.40–4.63 (m, 2H) 4.67 (dd, 1H) 7.03–7.33 and 7.50–7.70 (m, 13H). FAB-MS:- calculated for $C30H_{35}N_7O_2$ 525.3; found 526.3 (M+1).

EXAMPLE 19

(R)-α-[(3-Amino-3-methyl-1-oxybutyl)amino]-N-ethyl-N-[[2'-(1H-tetrazol-5-yl)-[1,1'-biphenyl]-4-yl]methyl]benzenebutanamide, trifluoroacetate Step A: (R)-α-[(3-t-Butoxycarbonylamino-3-methyl-1-oxobutyl)amino]-N-ethyl-N-[[2'-(N-triphenylmethyltetrazol-5-yl)[1,1'-biphenyl]-4-yl]methyl]benzenebutanamide (R)-α-[(3-t-Butoxycarbonylamino-3-methyl-1-oxobutyl)amino]benzenebutanoic acid (120 mg; 0.317 mmol) whose preparation was described in Example 7, Step D and the tetrazole amine, N-triphenylmethyl-5-[2-(4'-[(N-ethylamino)methyl]biphen-4-yl)tetrazole (110 mg; 0.211 mmol) from Step A of Example 18 were dissolved in methylene chloride (1 ml) then treated with triethylamine (73.6 μl; 0.528 mmol) and BOP reagent (186.8 mg; 0.422 mmol). The reaction mixture was treated as above in Example 18, Step A. In this case, after chromatography a thick oil (108 mg; 39%) was obtained of the desired amide. FAB-MS:- calculated for $C_{55}H_{59}N_7O_4$ 881.5; found 888.4 (M+Li).

Step B: (R)-α-[(3-Amino-3-methyl-1-oxybutyl)amino]-N-ethyl-N-[[2'-(1H-tetrazol-5-yl)-[1,1'-biphenyl]-4-yl]methyl]benzenebutanamide, trifluoroacetate The amide (62 mg; 0.070 mmol) from Step A of this Example was deprotected in methanol (1 ml) with 9N-hydrochloric acid (0.5 ml) in the presence of hexanes (2 ml) according to the procedure described in Example 18, Step C. After reversed phase hplc cleanup 27.6 mg (60.3%) of the desired title final product was obtained as a glass-like solid.

$^1$H NMR (400 MHz, CD$_3$OD): 1.03 (dt, 3H) 1.38 and 1.43 (2×d, 6H) 1.85–2.15 (m, 2H) 2.53 and 2.58 (2×s, 2H) 2.50–3.55 (m, 4H) 4.30–4.60 (m, 2H) 4.68 (m, 1H) 7.05–7.35 and 7.53–7.75 (m, 13H). FAB-MS:- calculated for $C_{31}H_{37}N_7O_2$ 539.3; found 540.3 (M+1).

EXAMPLE 20

(R)-α-[(2-Amino-2-methyl-1-oxypropyl)amino]-N-ethyl-N-[[(2'-[((methylamino)carbonyl)aminomethyl])-[1,1'-biphenyl]-4-yl]methyl] benzenebutanamide, trifluoroacetate Step A: 4-[N-Ethyl-(aminomethyl)]-2'(t-butoxycarbonylaminomethyl)-1,1'-biphenyl 4-Hydroxymethyl-2'(t-butoxycarbonylaminomethyl)-1,1'-biphenyl (70 mg; 0.224 mmol) was dissolved in dry methylene chloride and stirred at 0° C. in an iced water bath and methanesulfonyl chloride (22 µl; 0.285 mmol) and triethylamine (39 µl; 0.280 mmol) added. The reaction mixture was stirred for 3 h at 0° C. and then 70% aqueous ethylamine (5 ml) added. The mixture was stirred for 5 h at room temperature vigorously, then partitioned between water and methylene chloride. The organic phase was separated and the aqueous layer extracted with methylene chloride (2×25 ml). The combined methylene chloride layers were dried over potassium carbonate powder, filtered and evaporated under reduced pressure to leave a thick viscous oil. The oil was subjected to a short column chromatography using a solvent gradient initially of ethyl acetate and hexanes (1:1 v/v) then neat ethyl acetate and finally with ethyl acetate and methanol (3:1 v/v). This afforded 52 mg (68%) of the desired product. FAB-MS:- calculated for $C_{21}H_{28}N_2O_2$ 340.2 found 341.1 (M+1).

Step B: (R)-α-[Benzyloxycarbonylamino]-N-ethyl-N-[[(2'-(t-butoxycarbonylaminomethyl))-[1,1'-biphenyl]-4-yl]methyl]benzenebutanamide (R)-α-[Benzyloxyamino]benzenebutanoic acid (158.4 mg; 0.505 mmol) and the N-ethyl amine (110 mg; 0.337 mmol) from Step A of this Example were dissolved in dry methylene chloride (1 ml) and stirred at room temperature. Triethylamine (141 µl; 1.012 mmol) and BOP-reagent (223.6 mg; 0.506 mmol) were added and the resulting reaction mixture stirred at room temperature for 30 h. The volatiles were removed under reduced pressure using a rotary evaporator and the residues chromatographed on silica gel using ethyl acetate and hexanes (1:2 v/v) as solvent. The desired product amide (161 mg; 50%) was isolated as an clear thick oil. FAB-MS:- calculated for $C_{39}H_{45}N_3O_5$ 635.3; found 636 (M+1).

Step C: (R)-α-[Benzyloxyamino]-N-ethyl-N-[[(2'-(aminomethyl))-[1,1'-biphenyl]-4-yl]methyl]benzenebutanamide The amide (150 mg; 0.236 mmol) that was obtained in Step B of this Example was dissolved in dry methylene chloride (2 ml) and anisole (1 ml) added. The solution was stirred at room temperature and TFA (1 ml) added and the reaction mixture stirred for a further 2 h. The volatiles were removed under reduced pressure to leave a thick gum which was subjected to a short column chromatography on silica gel using ethyl acetate and hexanes (1:2 v/v) to remove the unwanted non-polar materials, then with methanol to obtain the product. The product was isolated as a glass. The yield was 106 mg (83.8%). FAB-MS:- calculated for $C_{34}H_{37}N_3O_3$ 535.3; found 536 (M+1).

Step D: (R)-α-[Benzyloxyamino]-N-ethyl-N-[[(2'-[[[(methyamino)carbonyl]amino]methyl][1,1'-biphenyl]-4-yl]methyl]benzenebutanamide The amide (100 mg; 0.187 mmol) starting material from this Example, Step C was dissolved in dry methylene chloride (1 ml) and vigorously stirred at room temperature and excess methyl isocyanate (54 µl; 0.915 mmol) added. The reaction was stirred for 8 h at room temperature and the volatiles removed under reduced pressure to give a thick oil. Purification of the thick oil by column chromatography on silica gel and using a solvent gradient of ethyl acetate and hexanes (1:1 v/v) to neat ethyl acetate afforded 84 mg (75.8%) of the desired urea. FAB-MS:- calculated for $C_{36}H_{40}N_4O_4$ 592.3; found 593 (M+1).

Step E: (R)-α-[Amino]-N-ethyl-N-[[(2'-[[[(methyamino) carbonyl]amino]methyl][1,1'-biphenyl]-4-yl]-methyl] benzenebutanamide The urea (80 mg; 0.135 mmol) from Step D of this Example was dissolved in methanol (5 ml) and Pearlman's catalyst, 30%-palladium(H) hydroxide on carbon (20 mg) added to the methanol solution and this mixture degassed under vacuum. An hydrogen atmosphere was introduced over the reaction mixture with the aid of a balloon at room temperature and the hydrogenation reaction conditions maintained for 12 h. The spent catalyst was removed by filtration through a Celite bed and the filtrates evaporated under reduced pressure to give the amine compound (54 mg; 87%) as a colorless glass. FAB-MS:- calculated for $C_{28}H_{34}N_4O_2$ 458.3; found 459 (M+1).

Step F: (R)-α-[(2-Amino-2-methyl-1-oxopropyl)amino]-N-ethyl-N-[[(2'-[[[(methyamino)carbonyl]amino]methyl]-[1,1'-biphenyl]-4-yl]methyl]benzenebutanamide, trifluoroacetate The amine (25 mg; 0.055 mmol) from Step E of this Example, t-butoxycarbonyl-α-methylalanine (16.7 mg; 0.082 mmol) and triethylamine (22.8 µl; 0.164 mmol) were dissolved in dry methylene chloride (1 ml) and BOP reagent (36.2 mg; 0.082 mmol) added. The reaction mixture was stirred at room temperature for 6 h. The volatiles were removed under reduced pressure and the residues chromatographed on silica gel using ethyl acetate and hexanes (1:1 v/v) as solvent initially then neat ethyl acetate. The product was isolated as a thick oil and was dissolved in methanol (1 ml) and stirred at room temperature. 9N-Hydrochloric acid was added and the reaction mixture stirred for 2 h after which the solvents were evaporated by using a stream of nitrogen gas. The residues thus obtained were purified by hplc on a C18 reversed phase column using a methanol and 0.1% aqueous TFA solvent gradient. A glass-like solid (32.4 mg; 94%) of the product was obtained.

$^1$H NMR (400 MHz, CD$_3$OD): 1.05 (dt, 3H) 1.63 (d, 3H) 1.68 (d, 3H) 1.85–2.26 (m, 2H) 2.45–3.54 (m, 4H) 2.65 (d, 3H) 4.20 (s, 2H) 4.40–4.80 (m, 3H) 7.07–7.45 (m, 13H). FAB-MS:- calculated for $C_{32}H_{41}N_5O_3$ 543.3; found 544.1 (M+1).

EXAMPLE 21

(R)-α-[(3-Amino-3-methyl-1-oxybutyl)amino]-N-ethyl-N-[[(2'-[[[(methylamino)carbonyl]amino] methyl]-[1,1'-biphenyl]-4-yl]methyl] benzenebutanamide, trifluoroacetate The amine (25 mg; 0.055 mmol) from Step E of Example 20, 3-t-butoxycarbonylamino-3-methylbutanoic acid (17.8 mg; 0.082 mmol) and triethylamine (22.8 µl; 0.164 mmol) were dissolved in dry methylene chloride (1 ml) and BOP reagent (36.2 mg; 0.082 mmol) added. The reaction mixture was stirred at room temperature for 5.5 h. The volatiles were removed under reduced pressure and the residues chromatographed on silica gel using ethyl acetate and hexanes (1:1 v/v) as solvent initially then neat ethyl acetate. The product was isolated as a thick oil and was dissolved in methanol (1 ml) and stirred at room temperature. 9N-Hydrochloric acid (1 ml) was added and the reaction mixture stirred for 2 h after which the solvents were evaporated by using a stream of nitrogen gas. The residues thus obtained were purified by hplc on a C18 reversed phase column using a methanol and 0.1% aqueous TFA solvent gradient. A glass-like solid (27.1 mg; 73.3%) of the product was obtained. $^1$H NMR (400 MHz, CD$_3$OD): 1.07 (dt, 3H) 1.37 (d, 3H) 1.41 (d, 3H) 3.51 and 3.58 (2×s, 2H) 2.50–3.55 (m, 2H) 4.20 (d, 2H)

4.50–4.85 (m, 3H) 7.07–7.45 (m, 13H). FAB-MS:- calculated for $C_{33}H_{43}N_5O_3$ 557.3; found 558.1 (M+1).

EXAMPLE 22

(R)-α-[(2-Amino-2-methyl-1-oxypropyl)amino]-N-[[2'-(1H-tetrazol-5-yl)-[1,1'-biphenyl]-4-yl]methyl]-N-(propyl)benzenebutanamide, trifluoroacetate Step A: N-Triphenylmethyl-5-[2-(4'-[(N-(2-propyl)amino) methyl]biphen-4-yl)tetrazole N-Triphenylmethyl-5-[2-(4'-[bromomethyl]biphen -4-yl) tetrazole (500 mg; 0.90 mmol) was dissolved in methylene chloride (5 ml) and neat isopropylamine (1 ml) added. The two phase system was stirred vigorously for 2 h at room temperature and then the volatiles removed by evaporation under reduced pressure. This afforded a thick yellow oil which was chromatographed on a short column of silica a gel using first a solvent mixture of ethyl acetate and hexanes in the ratio of 2:1 v/v then neat ethyl acetate and finally with ethyl acetate and methanol 19;1 v/v. The isopropylamine product was isolated as a white solid (411.9 mg; 85%). FAB-MS:- Calculated for $C_{36}H_{33}N_5$ 535.3; found 536.6 (M+1).

Step B: (R)-α-[(2-Amino-2-methyl-1-oxopropyl)amino]-N-(2-propyl)-N-[[2'-(1H-tetrazol-5-yl)[1,1'-biphenyl]-4-yl] methyl]benzenebutanamide, trifluoroacetate The acid (100 mg; 0.274 mmol) from Example 6, Step D, amine (147 mg; 0.274 mmol) from Step A of this Example and triethylamine (76.5 μl; 0.549 mmol) were dissolved in dry methylene chloride (1 ml) and stirred at room temperature. BOP reagent (121.4 mg; 0.274 mmol) was added and the reaction mixture stirred for 42 h at room temperature. The reaction was quenched by adding brine (5 ml) and extracted with methylene chloride (3×5 ml). The combined methylene chloride layers were dried over anhydrous magnesium sulfate powder, filtered and evaporated under reduced pressure to give a golden yellow oil. This material was partially purified by column chromatography on silica gel using an eluant comprising ethyl acetate and hexanes 2:1 v/v. The partially purified product (125 mg) was dissolved in a mixture of methanol (1 ml)and anisole (0.5 ml). 9N-Hydrochloric acid (0.5 ml) was added and the reaction mixture stirred at room temperature for 1.5 h then hexanes (0.5 ml) added, stirred for 0.5 h and the hexanes layer removed using a Pasteur pipette. The aqueous methanol phase was evaporated using a stream of nitrogen gas at room temperature and the residues purified by hplc on a C18-reversed phase column using a solvent gradient of methanol and 0.1% aqueous trifluoroacetic acid. In this way, 17.9 mg (10%) of the desired trifluoroacetic acid salt was obtained.

$^1$H NMR (400 MHz, CD$_3$OD): 1.00 and 1.13 (m and d, 6H total) 1.59, 1.62 and 1.68 (3×s, 6H) 1.75–2.9 (m, 4H) 3.75 and 4.48 (m, 1H) 4.2–4.55 (m, 2H) 4.78 (m, 1H) 7.0–7.7.75 (m, 13H). FAB-MS:- calculated for $C_{31}H_{37}N_7O_2$ 539.3 found 540.7 (M+1).

EXAMPLE 23

(R)-α-[(2-Amino-2-methyl-1-oxopropyl)amino]-N-[[2'-[[(methylamino)carbonyl]amino][1,1'-biphenyl]-4-yl]methyl]-3-[(phenylmethyl)oxy]propanamide, trifluoroacetate Step A: (R)-α-[(2-t-Butoxycarbonylamino-2-methyl-1-oxopropyl)amino]-N-[[(2'-nitro)[1,1'-biphenyl]-4-yl]-methyl]-3-[(phenylmethyl)oxy]propanamide N-(t-Butoxycarbonyl)-O-benzyl-D-serine (388 mg; 1.31 mmol), 4-aminomethyl-2'-nitro-1,1'-biphenyl (300 mg; 1.31 mmol) and triethylamine (365 μl; 2.62 mmol) were dissolved in methylene chloride (3 ml) and BOP-reagent (581.3 mg; 1.31 mmol) added. The reaction mixture was stirred at room temperature for 2.5 h then quenched by adding brine. The reaction mixture was extracted with methylene chloride (3×10 ml) and the combined methylene chloride layers were dried over magnesium sulfate powder, filtered and evaporated under reduced pressure. The brown oil thus obtained was chromatographed on silica gel using ethyl acetate and hexanes 4:1 v/v to give a clear oil. The yield was 587 mg (88%). FAB-MS:- Calculated for $C_{28}H_{31}N_3O_6$ 505.2; found 506.6 (M+1).

Step B: (R)-α-Amino-N-[[(2'-nitro)[1,1'-biphenyl]-4-yl]-methyl]-3-[(phenylmethyl)oxy]propanamide The amide (665 mg; 1.315 mmol) was dissolved in methylene chloride (5 ml) and anisole (1 ml) added. The homogeneous solution was stirred at room temperature and TFA added and stirred for 2 h. The volatiles were removed under vacuum using a rotary evaporator. The gummy residues were taken up in methylene chloride (50 ml) and washed with 10% aqueous sodium carbonate solution. The aqueous phase was extracted with methylene chloride (2×50 ml) and the combined methylene chloride layers was dried over ahydrous magnesium sulfate powder. After being filtered and evaporated under reduced pressure an oil was obtained. Column chromatography of the oil using ethyl acetate and hexanes (2:1 v/v), neat ethyl acetate and then ethyl acetate and ethanol 9:1 v/v afforded 416 mg of product (78%). FAB-MS:- Calculated for $C_{23}H_{23}N_3O_4$ 405.2; found 405.9(M).

Step C: (R)-α-[(2-t-Butoxycarbonylamino-2-methyl-1-oxopropyl)amino]-N-[[(2'-nitro)[1,1'-biphenyl]-4-yl] methyl]-3-[(phenylmethyl)oxy]propanamide The amine (200 mg; 0.49 mmol) from Step B of this Example and N-(t-butoxycarbonyl)-α-methylalanine (100 mg; 0.49 mmol) were dissolved in dry methylene chloride (2.5 ml) and triethylamine (138 μl; 0.99 mmol) and BOP-reagent (218 mg; 0.49 mmol) added. The resulting homogeneous solution was stirred overnight and the reaction then quenched by adding brine and extracted with methylene chloride (3×5 ml). The methylene chloride extract was dried over anhydrous magnesium sulfate, filtered and evaporated under partial vacuum to afford a thick oil. Column chromatography purification of this oil using ethyl acetate and hexanes (3:1 v/v) gave 268 mg (92%) of an oil that was the desired product. FAB-MS:- Calculated for $C_{32}H_{38}N_4O_7$ 590.3; found 613.2 (M+Na).

Step D: (R)-α-[(2-t-Butoxycarbonylamino-2-methyl-1-oxopropyl)amino]-N-[[(2'-[(methylaminocarbonyl)amino] [1,1'-biphenyl]-4-yl]-methyl]-3-[(phenylmethyl)oxy] propanamide The nitro compound (250 mg; 0.423 mmol) from Step C of this Example was dissolved in warm (approx. 40° C.) ethanol (30 ml) and Raney nickel (45 mg) added. The stirred ethanol solution was hydrogenated at room temperature for 30 h and the hydrogenation catalyst filtered off with the aid of a Celite bed. The amine was isolated after evaporation of solvent under reduced pressure to give an oil which was purified by column chromatography using ethyl acetate and hexanes 3:1 v/v. The recovery of (R)-α-[(2-t-Butoxycarbonylamino-2-methyl-1-oxopropyl)amino]-N-[[ (2'-amino)[1,1'-biphenyl]-4-yl]-methyl]-3-[(phenylmethyl) oxy]propanamide was (182 mg; 76%). A portion of the amine (50 mg; 0.089 mmol) and methyl isocyanate (46 μl; 0.78 mmol) were reacted together in dry methylene chloride (0.5 ml). The homogeneous solution was stirred overnight and the volatiles removed under reduced pressure and the residues chromatographed on silica gel using ethyl acetate and hexanes 4:1 v/v. This gave 42.1 mg (76%) of the desired material. FAB-MS:- Calculated for $C_{34}H_{43}N_5O_6$ 617.3; found 618.5 (M+1).

Step E: (R)-α-[(2-Amino-2-methyl-1-oxopropyl)amino]-N-[[(2'-[(methylaminocarbonyl)amino][1,1'-biphenyl]-4-yl]methyl]-3-[(phenylmethyl)oxy]propanamide, trifluoroacetate The urea from Step D (40 mg; 0.065 mmol) was dissolved in methanol (0.9 ml) and anisole (100 µl) added. The reaction mixture was stirred at room temperature and 9N-hydrochloric acid (10 drops from a Pasteur pipette) added. The reaction mixture was stirred for 0.5 h and the volatiles removed using a nitrogen gas stream. The solid was evaporated to dryness and then purified by hplc on a C18 column using a solvent gradient of methanol and 0.1% aqueous trifluoroacetic acid. In this way, 20.7 (50.6%) of the final material was obtained.

$^1$H NMR (400 MHz, CD$_3$OD): 1.57 (s, 3H) 1.61 (s, 3H) 2.66 (s, 3H) 3.78 (d, 2H) 4.44 (ABq, 2H) 4.55 (s, 2H) 4.70 (t, 3H). FAB-MS:- calculated for C$_{29}$H$_{35}$N$_5$O$_4$ 517.3; found 518.8 (M+1).

EXAMPLE 24

(R)-α-[(3-Amino-3-methyl-1-oxobutyl)amino]-N-[[(2'-[[(methylamino)carbonyl]amino][1,1'-biphenyl]-4-yl]-methyl]-3-[(phenylmethyl)oxy]propanamide trifluoracetate Step A: (R)-α-[(3-t-Butoxycarbonylamino-3-methyl-1-oxobutyl)amino]-N-[[(2'-nitro)[1,1'-biphenyl]-4-yl]-methyl]-3-[(phenylmethyl)oxy]propanamide The amine (200 mg; 0.49 mmol) from Step B of Example 23 and (R)-α-[(3-t-butoxycarbonylamino-3-methyl-1-oxobutyl)amino]benzenebutanoic acid (107 mg; 0.49 mmol) were dissolved in dry methylene chloride (5 ml) and triethylamine (138 µl; 0.99 mmol) and BOP-reagent (218 mg; 0.49 mmol) added. The resulting homogeneous solution was stirred overnight and the reaction then quenched by adding brine and extracted with methylene chloride (3×5 ml). The methylene chloride extract was dried over anhydrous magnesium sulfate, filtered and evaporated under partial vacuum to afford a thick oil. Column chromatography purification of this oil using ethyl acetate and hexanes (3:1 v/v) gave 292 mg (98%) of an oil that was the desired product. FAB-MS:- Calculated for C$_{33}$H$_{40}$N$_4$O$_7$ 604.3; found 605.4 (M+1).

Step B: (R)-α-[(3-t-Butoxycarbonylamino-3-methyl-1-oxobutyl)amino]-N-[[(2'-[[(methylamino)carbonyl]-amino][1,1'-biphenyl]-4-yl]-methyl]-3-[(phenyl-methyl)oxy]propanamide The nitro compound (250 mg; 0.423 mmol) from Step A of this Example was dissolved in warm (approx. 40° C.) ethanol (30 ml) and Raney nickel (45 mg) added. The stirred ethanol solution was hydrogenated at room temperature for 30 h and the hydrogenation catalyst filtered off with the aid of a Celite bed. The amine was isolated after evaporation of solvent under reduced pressure to give an oil which was purified by column chromatography using ethyl acetate and hexanes 3:1 v/v. The recovery of (R)-α-[(3-t-Butoxycarbonylamino-3-methyl- 1-oxobutyl)amino]-N-[[(2'-amino)[1,1'-biphenyl]-4-yl]-methyl]-3-[(phenylmethyl)oxy]propanamide was (192 mg; 79%). A portion of the amine (50 mg; 0.087 mmol) and methyl isocyanate (45.5 µl; 0.77 mmol) were reacted together in dry methylene chloride (0.5 ml). The homogeneous solution was stirred overnight and the volatiles removed under reduced pressure and the residues chromatographed on silica gel using ethyl acetate and hexanes 4:1 v/v. This gave 29.2 mg (76%) of the desired material. FAB-MS:- calculated for C$_{35}$H$_{45}$N$_5$O$_6$ 631.3; found 632.3.

Step C: (R)-α-[(3-Amino-3-methyl-1-oxobutyl)amino]-N-[[(2'-[(methylaminocarbonyl)amino][1,1'-biphenyl]-4-yl]-methyl]-3-[(phenylmethyl)oxy]propanamide, trifluoracetate The urea from Step B (24 mg; 0.038 mmol) was dissolved in methanol (2 ml) and anisole (100 µl) added. The reaction mixture was stirred at room temperature and 9N-hydrochloric acid (10 drops from a Pasteur pipette) added. The reaction mixture was stirred for 0.5 h and the volatiles removed using a nitrogen gas stream. The solid was evaporated to dryness and then purified by hplc on a C18 column using a solvent gradient of methanol and 0.1% aqueous trifluoroacetic acid. In this way, 13.2 mg (53.8%) of the final material was obtained.

$^1$H NMR (400 MHz, CD$_3$OD): 1.36 (s, 3H) 1.37 (s, 3H) 2.59 (ABq, 2H) 2.66 (s, 3H) 4.78 (m, 2H) 4.43 (ABq, 2H) 4.55 (ABq, 2H) 4.65 (t, 1H) 7.18–7.42 (m, 12H) 7.64 (d, 1H). FAB-MS:- calculated for C$_{30}$H$_{37}$N$_5$O$_4$ 531.3; found 532.7 (M+1).

Also obtained was the serine compound [(3-amino-3-methyl-1-oxobutyl)amino]-N-[[(2'-[[(methylamino)carbonyl]amino][1,1'-biphenyl]-4-yl]-methyl]-3-hydroxy-propanamide trifluoroacetic acid salt (6.2 mg). FAB-MS:- calculated for C$_{23}$H$_{31}$N$_5$O$_4$ 441; found 442 (M+1).

EXAMPLE 25

(R)-α-[(2-Amino-2-methyl-1-oxopropyl)amino]-N-[[(2'-[(2-hydroxyethylamino)carbonyl]amino][1,1'-biphenyl]-4-yl]-methyl]-3-[(phenylmethyl)oxy] propanamide, trifluoracetate Step A: (R)-α-[(2-t-Butoxycarbonylamino-2-methyl-1-oxopropyl)amino]-N-[[(2'-[(2-hydroxyethylamino)carbonyl]amino][1,1'-biphenyl]-4-yl]-methyl]-3-[(phenylmethyl)oxy]propanamide, methacrylate ester (R)-α-[(2-t-Butoxycarbonylamino-2-methyl-1-oxopropyl)amino]-N-[[(2'-amino)[1,1'-biphenyl]-4-yl]-methyl]-3-[(phenylmethyl)oxy]propanamide (50 mg; 0.087 mmol) from Step D, Example 23 and isocyanatoethyl methacrylate (40.5 mg; 0.261 mmol) were dissolved in dry methylene chloride (0.5 ml) and stirred at room temperature for 22 h. The volatiles were removed under reduced pressure and the residues chromatographed on silica gel using an eluant of ethyl acetate and hexanes 4:1 v/v. The sample (64.2 mg) was around 90% pure and taken onto the next step.

Step B: (R)-α-[(2-Amino-2-methyl-1-oxopropyl)amino]-N-[[(2'-[(2-hydroxyethylamino)carbonyl]amino][1,1'-biphenyl]-4-yl]-methyl]-3-[(phenylmethyl)oxy] propanamide, trifluoracetate The crude urea (62.5 mg) was dissolved in methanol (1 ml) and sodium methoxide solution (100 µl) [prepared from sodium (20 mg) and methanol (1 ml)] added and stirred together for 2 h at room temperature. Anisole (100 µl) was added followed by 9N-hydrochloric acid (10 drops from a Pasteur pipette). After 0.5 h at room temperature, the solvent was removed using a stream of nitrogen gas and the dry residues purified by hplc on a C18 reversed phase column using a solvent gradient of methanol and 0.1% aqueous trifluoroacetic acid. The yield of products was 22 mg.

$^1$H NMR (400 MHz; CD$_3$OD):- 1.57 (s, 3H) 1.60 (s, 3H) 3.21 (t, 2H) 3.52 (t, 2H) 3.77 (d, 2H) 4.43 (m, 2H) 4.55 (s, 2H) 4.69 (t, 1H) 7.10–7.38 (m, 12H) and 7.68 (d, 1H). FAB-MS:- calculated for C$_{30}$H$_{37}$N$_5$O$_5$ 547.3; found 548.8.

EXAMPLE 26

(R)-α-[(3-Amino-3-methyl-1-oxobutyl)amino]-N-[[(2'-[(2-hydroxyethylamino)carbonyl]amino][1,1'-biphenyl]-4-yl]-methyl]-3-[(phenylmethyl)oxy] propanamide, trifluoracetate Step A: (R)-α-[(2-t-Butoxycarbonylamino-2-methyl-1-oxopropyl)amino]-N-[[(2'-[(2-hydroxyethylamino)carbonyl]amino][1,1'-biphenyl]-4-yl]-methyl]-3-[(phenylmethyl)oxy]propanamide, methacrylate ester (R)-α-[(3-t-Butoxycarbonylamino-3-methyl-1-oxobutyl)amino]-N-[[(2'-amino)[1,1'-biphenyl]-4-yl]-methyl]-3-[(phenylmethyl)oxy]propanamide (30 mg; 0.048 mmol) from Step B of Example 24 and isocyanatoethyl methacrylate (65 mg; 0.261 mmol) were dissolved in dry methylene chloride (0.75 ml) and stirred at room temperature for 24 h. The volatiles were removed under reduced pressure and the residues chromatographed on silica gel using an eluant of ethyl acetate and hexanes 4:1 v/v then neat ethyl acetate. The sample (33 mg) was judged to be around 90% pure and taken onto the next step.

Step B: (R)-α-[(3-Amino-3-methyl-1-oxobutyl)amino]-N-[[(2'-[(2-hydroxyethylamino)carbonyl]amino][1,1'-biphenyl]-4-yl]-methyl]-3-[(phenylmethyl)oxy]propanamide, trifluoracetate The crude urea (33 mg) was dissolved in methanol (1 ml) and sodium methoxide solution (100 µl) [prepared from sodium (5 mg) and methanol (1 ml)] added and stirred together for 2 h at room temperature. Anisole (100 µl) was added followed by 9N-hydrochloric acid (10 drops from a Pasteur pipette). After 0.5 h at room temperature, the solvent was removed using a stream of nitrogen gas and the dry residues purified by mplc on a C8 reversed phase column using a solvent system of methanol and 0.1% aqueous trifluoroacetic acid in the ratio 1:1 v/v. The yield of products was 15.2 mg of (R)-α-[(3-amino-3-methyl-1-oxobutyl)amino]-N-[[(2'-[(2-hydroxyethylamino)carbonyl]amino][1,1'-biphenyl]-4-yl]-methyl]-3-[(phenylmethyl)oxy] propanamide trifluoroacetic acid salt.

$^1$H NMR (400 MHz; CD$_3$OD):- 1.37 (s, 3H) 1.39 (s, 3H) 2.60 (ABq, 2H) 3.21 (t, 2H) 3.52 (t, 2H) 3.77 (dq, 2H) 4.47 (m, 2H) 4.54 (s, 2H) 4.66 (t, 1H) 7.10–7.38 (m, 12H) and 7.68 (d, 1H). FAB-MS:- calculated for C$_{31}$H$_{39}$N$_5$O$_5$ 561.3; found 562.8.

EXAMPLE 27

(R)-α-[(2-Amino-2-methyl-1-oxypropyl)amino]-N-[[2'-(1H-tetrazol-5-yl)-[1,1'-biphenyl]-4-yl]methyl]-3-[(phenylmethyl)oxy]propanamide, trifluoracetate Step A: N-(t-Butoxycarbonyl)-O-Benzyl-D-Serine Allyl Ester N-(t-Butoxycarbonyl)-O-benzyl-D-serine (600 mg; 2.03 mmol) was dissolved in dry methylene chloride (5 ml), allyl alcohol (152 µl; 2.23 mmol) and DMAP (25 mg; 0.20 mmol) added and finally EDC (428.5 mg; 2.24 mmol) added to the acid. The reaction mixture was stirred at room temperature for 2.5 h and the resulting homogeneous solution quenched with water and extracted with methylene chloride. The methylene chloride layer was washed with 5% aqueous citric acid then 10% aqueous sodium carbonate solution. The methylene chloride layer was dried over anhydrous magnesium sulfate powder, filtered and evaporated under reduced pressure to give an oil. Chromatography of the oil using ethyl acetate and hexanes 1:2 v/v afforded the product (408 mg; 60%) as a pale yellow gum. FAB-MS:- Calculated for C$_{36}$H$_{33}$N$_5$ 335.1; found 336.1 (M+1).

Step B: O-Benzyl-D-serine allyl ester

The allyl ester (400 mg; 1.193 mmol) from Step A of this Example was dissolved in a mixture of anisole (0.5 ml) and methylene chloride (4 ml). Trifluoroacetic acid (2 ml) was added to the ester and the reaction mixture stirred for 2 h and the volatiles removed under vacuum using a rotary evaporator. The gummy residues were taken up in methylene chloride (10 ml) and washed with 10% aqueous sodium carbonate solution. The methylene chloride layer was dried over anhydrous magnesium sulfate powder, filtered and evaporated under reduced pressure to leave an oil. Column chromatography of the oil using ethyl acetate and hexanes (2:1 v/v), neat ethyl acetate and then ethyl acetate and ethanol 9:1 v/v afforded a pale yellow oil (207 mg; 73.7%). FAB-MS:- Calculated for C$_{13}$H$_{17}$NO$_3$ 235.1; found 235.8 (M).

Step C: (R)-α-[(2-t-Butoxycarbonylamino)-2-methyl-1-oxopropyl)amino]-3-[(phenylmethyl)oxy]propanoic acid, allyl ester O-Benzyl-D-serine allyl ester (90 mg; 0.38 mmol), N-(t-butoxycarbonyl)-α-methylalanine (78 mg; 0.38 mmol) were dissolved in dry methylene chloride (3 ml) and triethylamine (107 µl; 0.77 mmol) and BOP-reagent (169 mg; 0.38 mmol) added. The resulting homogeneous solution was stirred for 3 h and the reaction then quenched by adding brine and extracted with methylene chloride. The methylene chloride extract was dried over anhydrous magnesium sulfate, filtered and evaporated under partial vacuum to afford a thick oil. Column chromatography purification of this oil gave 122 mg (76%) of an almost colorless oil that was the desired product. FAB-MS:- Calculated for C$_{22}$H$_{32}$N$_2$O$_6$ 420.2; found 421.2 (M+1).

Step D: (R)-α-[(2-t-Butoxycarbonylamino)-2-methyl-1-oxopropyl)amino]-3-[(phenylmethyl)oxy]propanoic acid The allyl ester (100 mg; 0.238 mmol) from Step C of this Example was dissolved in dry methylene chloride (1 ml) and stirred at room temperature and tetrakis(triphenylphoshine)palladium(0) (3 mg) added along with triphenylphosphine (1.5 mg). A solution of 2-methylhexanoic acid potassium salt (0.56 ml) (0.5M in ethyl acetate) was added and stirred together for 3 days under nitrogen. The volatiles were removed under reduced pressure and the residues chromatographed on silica gel using first ethyl acetate and hexanes 2:1 v/v then neat ethyl acetate and finally ethyl acetate and ethanol 19:1 v/v. The acid 62.3 mg; (68%) was isolated as a thick oil. FAB-MS:- Calculated for C$_{19}$H$_{28}$N$_2$O$_6$ 380.2; found 419.1 (M+K).

Step E: (R)-α-[(2-t-Butoxycarbonylamino)-2-methyl-1-oxopropyl)amino]-N-[[2'-(N-triphenylmethyl-tetrazol-5-yl)[1,1'-biphenyl]-4-yl]methyl]-3-[(phenylmethyl)oxy] propanamide The acid (40 mg; 0.105 mmol) from Step D of this Example, N-triphenylmethyl-5-[2-(4'-aminomethylbiphen-4-yl)]tetrazole (55 mg; 0.106 mmol) from Step F of Example 1 and triethylamine (30 µl; 0.215 mmol) were dissolved in methylene chloride (1 ml) and BOP-reagent (46.6 mg; 0.105 mmol) added. The reaction mixture was stirred at room temperature for 3.5 h then quenched by adding brine (5 ml). The reaction mixture was extracted with methylene chloride (3×10 ml) and the combined methylene chloride layers were dried over magnesium sulfate powder, filtered and evaporated under reduced pressure. The brown oil thus obtained was chromatographed on silica gel using ethyl acetate and hexanes 2:1 v/v to give a clear pale yellow oil. The yield was 52.4 mg (58%). FAB-MS:- calculated for C$_{52}$H$_{53}$N$_7$O$_5$, 855; found 862.5 (M+Li).

85

Step F: (R)-α-[(2-Amino-2-methyl-1-oxypropyl)amino]-N-[[2'-(1H-tetrazol-5-yl)-[1,1'-biphenyl]-4-yl]methyl]-3-[(phenylmethyl)oxy]propanamide, trifluoracetate The tetrazole (50 mg; 0.058 mmol) from Step E of this Example was dissolved in methanol (1 ml) and anisole (250 μl). 9N-Hydrochloric acid (10 drops from a Pasteur pipette) and hexanes (1 ml) added. The mixture was vigorously stirred at room temperature for 0.5 h and the hexanes layer removed using a Pasteur pipette and discarded and the remaining methanolic solution evaporated with a stream of nitrogen. The solid material that was left after solvent removal was purified by hplc using a C18 reversed phase column using methanol and 0.1% aqueous trifluoroacetic acid gradient. The product, an amorphous powder (8.1 mg) was isolated.

$^1$H NMR (400 MHz; CD$_3$OD):- 1.56 (s, 3H) 1.59 (s, 3H) 3.75 (d, 2H) 4.38 (aBq, 2H) 4.53 (s, 2H) 4.66 (t, 1H) 7.02 (d, 2H) 7.21 (d, 2H) 7.30 (m, 5H) 7.52 (d, 1H) 7.57 (d, 1H) 7.68 (t, 2H). FAB-MS:- calculated for C$_{28}$H$_{31}$N$_7$O$_3$ 513.2; found 514.8 (M+1).

EXAMPLE 28

(R)-α-[(3-Amino-3-methyl-1-oxybutyl)amino]-N-[[2'-(1H-tetrazol-5-yl)-[1,1'-biphenyl]-4-yl]methyl]-3-[(phenylmethyl)oxy]propanamide, trifluoracetate Step A: (R)-α-[(3-t-Butoxycarbonylamino)-3-methyl-1-oxobutyl)amino]-3-[(phenylmethyl)oxy]propanoic acid, allyl ester O-Benzyl-D-serine allyl ester (95 mg; 0.40 mmol), (R)-α-[(3-t-butoxycarbonylamino-3-methyl-1-oxobutyl)amino]-benzenebutanoic acid (88 mg; 0.41 mmol) were dissolved in dry methylene chloride (3 ml) and treated with triethylamine (113 μl; 0.77 mmol) and BOP-reagent (179 mg; 0.38 mmol) as described in Example 27 Step C. In this case a pale yellow oil 104.2 mg (60%) was obtained that was the desired product. FAB-MS:- Calculated for C$_{23}$H$_{34}$N$_2$O$_6$ 434.2; found 435.3 (M+1).

Step B: (R)-α-[(3-t-Butoxycarbonylamino)-3-methyl-1-oxobutyl)amino]-3-[(phenylmethyl)oxy]propanoic acid The allyl ester (100 mg; 0.238 mmol) from Step A of this Example was dissolved in dry methylene chloride (1 ml) and stirred at room temperature and tetrakis(triphenylphoshine)palladium(0) (3 mg) added along with triphenylphosphine (1.5 mg). A solution of 2-methylhexanoic acid potassium salt (0.56 ml) (0.5M in ethyl acetate) was added and stirred together for 3 days. The volatiles were removed under reduced pressure and the residues chromatographed on silica gel using first ethyl acetate and hexanes 2:1 v/v then neat ethyl acetate and finally ethyl acetate and ethanol 19:1 v/v. The acid 54.2 mg; (57%) was isolated as a thick oil. FAB-MS:- Calculated for C$_{20}$H$_{30}$N$_2$O$_6$ 394.2; found 433.2 (M+K).

Step C: (R)-α-[(3-t-Butoxycarbonylamino-3-methyl-1-oxobutyl)amino]-N-[[2'-(N-triphenylmethyl-tetrazol-5-yl)[1,1'-biphenyl]-4-yl]methyl]-3-[(phenylmethyl)oxy]propanamide The acid (40 mg; 0.105 mmol) from Step B of this Example, N-triphenylmethyl-5-[2-(4'-aminomethylbiphen-4-yl)]tetrazole (55 mg; 0.106 mmol) from Step F of Example 1 and triethylamine (30 μl; 0.215 mmol) were dissolved in methylene chloride (1 ml) and BOP-reagent (46.6 mg; 0.105 mmol) added. The reaction mixture was stirred at room temperature for 3.5 h then quenched by adding brine (5 ml). The reaction mixture was extracted with methylene chloride (3×10 ml) and the combined methylene chloride layers were dried over magnesium sulfate powder, filtered and evaporated under reduced pressure. The yellow oil thus obtained was chromatographed on silica gel using ethyl acetate and hexanes 2:1 v/v to give a clear pale yellow oil. The yield was 55.1 mg (58%).

Step D: (R)-α-[(3-Amino-3-methyl-1-oxybutyl)amino]-N-[[2'-(1H-tetrazol-5-yl)-[1,1'-biphenyl]-4-yl]methyl]-3-[(phenylmethyl)oxy]propanamide, trifluoracetate The tetrazole (50 mg; 0.058 mmol) from Step C of this Example was dissolved in methanol (1 ml) and anisole (250 μl) and deprotected with 9N-hydrochloric acid and hexanes (1 ml) as described in Example 27, Step F. Purification by HPLC using a C18 reversed phase column using methanol and 0.1% aqueous trifluoroacetic acid gradient gave the product as an amorphous powder (6.2 mg) was isolated.

$^1$H NMR (400 MHz; CD$_3$OD):- 1.33 (s, 3H) 1.34 (s, 3H) 2.57 (ABq, 2H) 3.72 (dq, 2H) 4.39 (ABq, 2H) 4.53 (s, 2H) 4.63 (t, 1H) 7.00 (d, 2H) 7.20 (d, 2H) 7.30 (m, 5H) 7.50 (d, 1H) 7.55 (d, 1H) 7.68 (t, 2H). FAB-MS:- calculated for C$_{29}$H$_{33}$N$_7$O$_3$ 527.3; found 528.8 (M+1).

EXAMPLE 29

(R)-α-[(2-Amino-2-methyl-1-oxypropyl)amino]-N-(4-methoxyphenyl)-N-[[2'-(1H-tetrazol-5-yl)-[1,1'-biphenyl]-4-yl]methyl]benzenebutanamide, trifluoroacetate Step A: R-(α)-t-Butoxycarbonylamino-N-(4-methoxyphenyl)benzenebutanamide N-t-Butoxycarbonyl-D-homophenylalanine (250 mg; 0.895 mmol) and 4-methoxyaniline (110.2 mg; 0.895 mmol) were dissolved in methylene chloride (2 ml) and reacted with 1-hydroxybenztriazole (121 mg; 0.895 mmol) in the presence of DMAP (11 mg) and EDC (171.6 mg; 0.895 mmol). The reaction mixture was stirred at room temperature for 2 h and the reaction quenched with brine and partitioned with methylene chloride (3×10 ml). The combined methylene chloride layers were dried over magnesium sulfate, filtered and evaporated under vacuum to leave a yellow oil. Chromatography of the oil using ethyl acetate and hexanes 1:1 v/v gave the desired product as an off white solid. The yield was 192 mg (55.8%). FAB-MS:- calculated for C$_{22}$H$_{28}$N$_2$O$_4$ 384.2; found 385.9 (M+1).

Step B: R-(α)-t-Butoxycarbonylamino-N-(4-methoxyphenyl)-N-[[2'-(N-triphenylmethyl-tetrazol-5-yl)-[1,1'-biphenyl]-4-yl]methyl]benzenebutanamide The amide (116.2 mg; 0.30 mmol) from Step A of this Example was dissolved in THF (2 ml) under a nitrogen atmosphere at room temperature and potassium hydride powder (15.2 mg; 0.38 mmol) that had been previously freed from oil and dried under vacuum, added. A yellow solution formed within 5 minutes and after a futher 55 minutes, the yellow solution was cooled in an iced water bath and HMPA (54 μl; 0.31 mmol) added followed by N-triphenylmethyl-5-[2-(4'-[bromomethyl]-biphen-4-yl)tetrazole (200 mg; 0.359 mmol) dissolved in THF (2 ml). The reaction was allowed to warm to room temperature and stirred for a further 4 h during which time the ice bath had melted. The reaction was acidified with 5 drops of 2N-hydrochloric acid and quickly extracted with diethyl ether (3×25 ml). The combined ethereal extracts were dried over magnesium sulfate, filtered and evaporated under reduced pressure. The residues were chromatographed on silica gel using ethyl acetate and hexanes 2:1 v/v. The product was isolated as a yellow foam. Yield 250.6 mg (96%). FAB-MS:- calculated for C$_{55}$H$_{52}$N$_6$O$_4$ 860.4; found 860.3 (M).

Step C: R-(α)-Amino-N-(4-methoxyphenyl)-N-[[2'-(1H-tetrazol-5-yl)-[1,1'-biphenyl]-4-yl]methyl]-benzenebutanamide, hydrochloride salt The amide (250 mg; 0.29 mmol) from Step B of this Example was dissolved in methanol (3 ml) and anisole (3 ml) and 9N-hydrochloric acid added at room temperature to the amide. After 1 h of stirring at room temperature, hexanes (3 ml) was added and stirred into the aqueous methanol layer and then removed. The aqueous methanol was removed by evaporation with a stream of nitrogen gas. In this way, the crude salt was obtained (192.5 mg). FAB-MS:- calculated for $C_{31}H_{30}N_6O_2$ 518.2; found 519.6 (M+1).

Step D: (R)-(α)-[(2-t-Butoxycarbonylamino-2-methyl-1-oxopropyl)amino]-N-(4-methoxyphenyl)-N-[[2'-(1H-tetrazol-5-yl)-[1,1'-biphenyl]-4-yl]methyl] benzenebutanamide The amine hydrochloride (30 mg; 0.054 mmol) from Step C of this Example was dissolved in methylene chloride (1 ml) and triethylamine (16 µl, 0.115 mmol) added along with N-t-butoxycarbonyl-α-methylalanine (12 mg, 0.059 mmol). BOP-reagent (26 mg; 0.059 mmol) was added to the homogeneous solution and the reaction stirred for 72 h. The volatiles were removed under reduced pressure and the product isolated after two column chromatographies using ethyl acetate and hexanes 2:1 v/v as eluant. The yield was 36.8 mg (ca.95%), the product contaminated with a small amount of HMPA. FAB-MS:- calculated for $C_{40}H_{45}N_7O_5$ 703.3; found 726.5 (M+Na).

Step E: (R)-α-[(2-Amino-2-methyl-1-oxypropyl)amino]-N-(4-methoxyphenyl)-N-[[2'-(1H-tetrazol-5-yl)-[1,1'-biphenyl]-4-yl]methyl]benzenebutanamide, trifluoroacetate The tetrazole-containing product (46 mg) from Step D of this Example was dissolved in methanol (2 ml) and 9N-hydrochloric acid (0.5 ml) was added. The reaction mixture was stirred for 0.5 h and then hexanes (1 ml) added, stirred into the aqueous methanol phase for 15 minutes and then removed with a Pasteur pipette. The aqueous methanol layer was evaporated to dryness using a stream of nitrogen gas and the residues pumped dry. The crude product was purified by hplc using a C18 reversed phase column using a methanol and 0.1% aqueous TFA solvent system to yield 29.0 mg of the salt as a glassy solid.

$^1$H NMR (400 MHz; $CD_3OD$):- 1.63 (s, 3H) 1.66 (s, 3H) 1.89 (m, 2H) 2.34 (m, 1H) 2.62 (m, 1H) 3.79 (s, 3H) 4.29 (m, 1H) 4.62 and 4.97 (ABq, 2H) 6.73 (d, 2H) 6.80 (d, 2H) 6.90 (d, 2H) 6.98 (d, 2H) 7.07 (m, 5H) 7.53 (dd, 2H) 7.65 (dd, 2H). FAB-MS:- calculated for $C_{35}H_{37}N_7O_3$ 603.3; found 604.4 (M+1).

EXAMPLE 30

(R)-α-[(3-Amino-3-methyl-1-oxybutyl)amino]-N-(4-methoxyphenyl)-N-[[2'-(1H-tetrazol-5-yl)-[1,1'-biphenyl]-4-yl]methyl]-benzenebutanamide, trifluoroacetate Step A: (R)-(α)-[(3-t-Butoxycarbonylamino-3-methyl-1-oxobutyl)amino]-N-(4-methoxyphenyl)-N-[[2'-(1H-tetrazol-5-yl)-[1,1'-biphenyl]-4-yl]methyl]-benzenebutanamide The amine hydrochloride (30 mg; 0.054 mmol) from Step C of Example 29 was dissolved in methylene chloride (1 ml) and triethylamine (16 µl, 0.115 mmol) added along with (R)-α-[(3-t-butoxycarbonylamino-3-methyl-1-oxobutyl)amino]benzenebutanoic acid (12.6 mg, 0.058 mmol). BOP-reagent (25 mg; 0.057 mmol) was added to the cloudy solution and the reaction stirred for 72 h. The reaction was quenched with brine (3 ml) and extracted with methylene chloride (7×5 ml). The combined extracts were dried over anhydrous magnesium sulfate powder filtered and evaporated under partial vacuum and the product isolated after two column chromatographies using ethyl acetate and hexanes 2:1 v/v as eluant. The yield was 43 mg; the product contaminated with a small amount of HMPA. FAB-MS:- calculated for $C_{41}H_{47}N_7O_5$ 717.4; found 740.6 (M+Na).

Step B: (R)-α-[(3-Amino-3-methyl-1-oxybutyl)amino]-N-(4-methoxyphenyl)-N-[[2'-(1H-tetrazol-5-yl)-[1,1'-biphenyl]-4-yl]methyl]-benzenebutanamide, trifluoroacetate The tetrazole-containing product (42.8 mg) from Step A of this Example was dissolved in methanol (1 ml) and 9N-hydrochloric acid (0.5 ml)was added. The reaction mixture was treated similarly to that in Example 29, Step E. The crude product was purified by HPLC using a C18 reversed phase column using a methanol and 0.1% aqueous TFA solvent system to yield 28.2 mg of the salt as a glassy solid.

$^1$H NMR (400 MHz; $CD_3OD$):- 1.39 (s, 3H) 1.41 (s, 3H) 1.85 (q, 2H) 2.36 (m, 1H) 2.55 (ABq, 2H) 2.60 (m, 1H) 3.77 (s, 3H) 4.26 (m, 1H) 4.67 and 5.01 (ABq, 2H) 6.76 (d, 2H) 6.82 (d, 2H) 6.90 (d, 2H) 7.00 (d, 2H) 7.07 (m, 5H) 7.51 (m, 2H) 7.63 (dd, 2H). FAB-MS:- calculated for $C_{36}H_{39}N_7O_3$ 617.3; found 618.4 (M+1).

EXAMPLE 31

(R)-α-[(2-Amino-2-methyl-1-oxypropyl)amino]-N-(4-hydroxyphenyl)-N-[[2'-(1H-tetrazol-5-yl)-[1,1'-biphenyl]-4-yl]methyl]benzene-butanamide, trifluoroacetate (R)-α-[(2-Amino-2-methyl-1-oxypropyl)amino]-N-(4-methoxyphenyl)-N-[[2'-(1H-tetrazol-5-yl)-[1,1'-biphenyl]-4-yl]methyl]benzenebutanamide trifluoroacetic acid salt (10 mg; 0.014 mmol) was dissolved in dry methylene chloride and boron tribromide solution (167 µl, 1M in $CH_2Cl_2$; 0.167 mmol) added to the salt. The reaction mixture was stirred for 8 h at room temperature and then the volatiles removed under reduced pressure. The residues were purified by HPLC on a C18 reversed phase column using a methanol and 0.1% aqueous TFA gradient to give 5.2 mg (52%) of the desired product.

$^1$H NMR (400 MHz; $CD_3OD$): 1.61 (s, 3H) 1.66 (s, 3H) 1.95 (m, 2H) 2.36 (m, 1H) 2.63 (m, 1H) 4.33 (m, 1H) 4.63 and 4.97 (ABq, 2H) 6.62 (d, 2H) 6.82 (dd, 2H) 6.86 (d, 2H) 7.01 (d, 2H) 7.11 (m, 5H) 7.55 (m, 2H) 7.67 (m, 2H). FAB-MS:- calculated for $C_{34}H_{35}N_7O_3$ 589.3; found 590.6 (M+1).

EXAMPLE 32

(R)-α-[(3-Amino-3-methyl-1-oxybutyl)amino]-N-(4-methoxyphenyl)-N-[[2'-(1H-tetrazol-5-yl)-[1,1'-biphenyl]-4-yl]methyl]benzenebutanamide, trifluoroacetate (R)-α-[(3-Amino-3-methyl-1-oxybutyl)amino]-N-(4-methoxyphenyl)-N-[[2'-(1H-tetrazol-5-yl)-[1,1'-biphenyl]-4-yl]methyl]benzenebutanamide, trifluoroacetate (10 mg; 0.014 mmol) was dissolved in dry methylene chloride and boron tribromide solution (174 µl, 1M in $CH_2Cl_2$; 0.174 mmol) added to the salt. The reaction mixture was stirred for 8 h at room temperature and then the volatiles removed under reduced pressure. The residues were purified by hplc on a C18 reversed phase column using a methanol and 0.1% aqueous TFA gradient to give 5.0 mg (50%) of the desired product.

$^1$H NMR (400 MHz; $CD_3OD$): 1.38 (s, 3H) 1.40 (s, 3H) 1.88 (m, 2H) 2.37 (m, 1H) 2.254 (ABq, 2H) 2.62 (m, 1H) 4.31 (m, 1H) 4.59 and 4.99 (ABq, 2H) 6.64 (d, 2H) 6.84 (m, 2H) 6.86 (d, 2H) 7.00 (d, 2H) 7.11 (m, 5H) 7.54 (m, 2H) 7.66 (m, 2H). FAB-MS:- calculated for $C_{35}H_{37}N_7O_3$ 603.3; found 604.5 (M+1).

EXAMPLE 33

(R)-α-[(2-Amino-2-methyl)-1-oxopropyl]amino-N-methyl-N-[(2'-[[(methylamino)carbonyl]amino][1,1'-biphenyl]-4-yl]-benzenebutanamide, trifluoroacetate Step A: 4-(t-Butoxycarbonylamino)iodobenzene 4-Iodoaniline (6 g; 27.4 mmol) and di-t-butyl dicarbonate (7.5 g; 34.4 mmol) were dissolved in methylene chloride (50 ml) and the reaction mixture stirred at room temperature for 19 h. The volatiles were removed under reduced pressure and the residues crystallised from ethyl acetate and hexanes 9:1 v/v to give 4.42 g of product. The mother liquors were evaporated under reduced pressure and then were chromatographed on silica gel using a solvent system comprising ether and hexanes 1:3 v/v. Chromatography afforded a further 2.75 g of product. A total yield of 7.17 g (82%) was obtained in the reaction. FAB-MS:- calculated for $C_{11}H_{14}NO_2$ I 319.0 found 319.8 (M).

Step B: [4-(t-Butoxycarbonylamino)phenyl]trimethylstannane

The iodide (2.75 g; 8.62 mmol) from Step A of this Example, hexamethylditin (4.23 g; 12.91 mmol) and tetrakis(triphenylphosphine)palladium(0) were mixed together in anhydrous dioxane and subjected to a freeze-vac-thaw cycle to degas the solution and then the reaction heated to reflux under a nitrogen atmosphere for 6 h. The reaction mixture was then cooled to room temperature, poured into iced saturated brine and extracted with ether (3×250 ml). The ethereal layers were combined and washed with another portion of brine, dried over anhydrous magnesium sulfate powder and evaporated under reduced pressure to leave an orange mobile liquid. Chromatography of the liquid on silica gel using an eluant consisting of ether and hexanes in the ratio 1:19 v/v afforded 1.75 g (ca. 57%) of a material that was [4-(t-butoxycarbonylamino)phenyl]trimethylstannane that contained traces of the starting material.

$^1$H NMR (200 MHz, CDCl$_3$): 0.23 (s, 9H) 1.47 (s, 9H) 6.45 (s, 1H) 7.25–7.40 (ABq, 4H).

Step C: [4-[[N-(t-Butoxycarbonyl)-N-methyl]amino]phenyl]trimethylstannane

The arylstannane (1.25 g; 3.51 mmol) from Step B was dissolved in anhydrous THF (5 ml). In another flask, dry oil-free potassium hydride powder (140.8 mg; 3.51 mmol) was suspended in THF (10 ml) and cooled to 0° C. under nitrogen. The solution of the stannane was added to the hydride with stirring, the addition being completed in 5 min. Gas evolution was observed during the addition of the tin reagent, and the solution became yellow then darkened slightly. After 0.5 h at 0° C., hexamethylphosphoramide (HMPA) (641.4 μl; 3.69 mmol) was added followed by excess neat methyl iodide (1.1 ml; 17.67 mmol) and the dark yellow colour discharged to give a milky white solution. The reaction mixture was allowed to warm gradually to room temperature after the methyl iodide addition and stirred for a further 1 h at room temperature. Saturated brine was added carefully to the reaction mixture to quench the unreacted hydride and then the resulting two phase system extracted with ether (2×50 ml). The ethereal extracts were dried with anhydrous magnesium sulfate powder, filtered and evaporated under reduced pressure. The residues were chromatographed on silica gel using a solvent mixture of ether and hexanes 1:2 v/v. In this way the desired product (1.2 g; 92%) was obtained. $^1$H NMR (400 MHz, CDCl$_3$): 0.25 (s, 9H) 1.44 (s, 9H) 3.23 (s, 3H) 7.19 and 7.42 (AA'BB', 4H).

Step D: 4-[(N-(t-Butoxycarbonyl)-N-methyl)amino]-2'-nitro-1,1'-biphenyl

The N-methylated tin compound from Step C (600 mg; 1.62 mmol) of this Example, 1-bromo-2-nitrobenzene (327.5 mg; 1.62 mmol) and tetakis(triphenylphosphine)palladium(0) (50 mg) were all dissolved in anhydrous dioxane (8 ml) and stirred at room temperature. The solution was degassed by a freeze-vac-thaw cycle and the solution heated to reflux for 4.5 h and then allowed to stand at room temperature overnight. The solvents were removed and the residues chromatogarphed on silica gel using a solvent mixture of diethyl ether and hexanes 1:3 v/v. The desired product was obtained as an orange oil. The yield was 502.4 mg (94%).

$^1$H NMR (400 MHz, CDCl$_3$): 1.44 (s, 9H) 3.28 (s, 3H) 7.28 (AA'BB', 4H) 7.44 (m, 2H) 7.58 (dt, 1H) 7.82 (d, 1H). FAB-MS:- calculated for $C_{18}H_{20}N_2O_4$ 328. found 328 (M).

Step E: 4-[(N-Methyl)amino]-2'-nitro-1,1'-biphenyl

The carbamate from Step D (500 mg; 1.52 mmol) of this Example was dissolved in dry methylene chloride (5 ml) and anisole added (2.5 ml). The solution was stirred at room temperature and TFA added drop by drop to the solution. After stirring for approximately 0.5 h, tlc of the reaction indicated the reaction was over. The volatiles were removed under aspirator vacuum and the residues stored overnight on a vacuum line. The sample was redissolved in methylene chloride, washed with saturated aqueous sodium bicarbonate solution and the methylene chloride layer dried over anhydrous potassium carbonate powder. The solvent was removed under reduced pressure on a rotorvapor and the residues stored overnight then purified by column chromatography on silica gel using an eluant of ether and hexanes 1:1 v/v. A dark orange oil (350.9 mg) of the desired amine, 4-[(N-Methyl)amino]-2'-nitro-1,1'-biphenyl was obtained after chromatography.

$^1$H NMR (400 MHz, CDCl$_3$): 2.86 (d, 3H) 3.85 (s, 1H) 6.63, 7.13 (AA'BB', 4H) 7.37 (dt, 1H) 7.40 (d, 1H) 7.53 (t, 1H) 7.73 (d, 1H). FAB-MS:- calculated for $C_{13}H_{12}N_2O_2$ 228. 1 found 228.8 (M).

Step F: (R)-α-[N-(9-Fluorenylmethoxycarbonyl)amino]-N-methyl-N-[(2'-nitro)[1,1'-biphenyl]-4-yl]-benzenebutanamide N-FMOC-(–)-Amino-4-phenylbutyric acid (770 mg; 1.92 mmol) and 1 drop of N,N-dimethylformamide from a Pasteur pipette were dissolved in dry methylene chloride (5 ml) and stirred at room temperature. Oxalyl chloride (184 μl; 2.11 mmol)was added drop by drop to the acid solution, the addition being complete within 5 minutes. The reaction mixture was stirred for 14 h and the volatiles carefully removed under vacuum. The residue was a bright orange solid and was used without purification for amide coupling. The orange solid was dissolved in redissoved in methylene chloride (5 ml) and triethylamine (321 μl; 2.3 mmol) and 4-[(N-methyl)amino]-2'-nitro-1,1'-biphenyl (350 mg; 1.54 mmol) added. The reaction mixture was stirred at room temperature overnight. The volatiles were removed under reduced pressure and the residues thus obtained were chromatographed on silica gel using a solvent system comprising ethyl acetate and hexanes in the ratio of 1:1 v/v. The product (1.15 g; ca. 95%) was isolated as a foamy solid which conatined traces of ethyl acetate. FAB-MS:- calculated for $C_{38}H_{33}N_3O_5$ 611.2 found 612.4 (M+1).

Step G: (R)-α-Amino-N-methyl-N-[(2'-nitro)[1,1'-biphenyl]-4-yl]-benzenebutanamide The FMOC amide from Step F (1.15 g; 1.88 mmol) was dissolved in methylene chloride (10 ml) and 4-(aminomethyl)piperidine (1 ml) added. The reaction mixture was stirred at room temperature. The reaction mixture was stirred for 15 minutes and then quenched by adding water. The methylene chloride phase was separated, dried over ahnydrous potassium carbonate powder, filtered and evaprated under reduced pressure to afford an orange-yellow oil. The oil was chromatographed on silica gel using an eluant of ethyl acetate and methanol (9:1 v/v). A pale yellow oil (517 mg; 70.6%) was isolated of the amine. FAB-MS:- calculated for $C_{23}H_{23}N_3O_3$ 389.2 found 389.9 (M).

Step H: (R)-α-[(2-t-Butoxycarbonylamino-2-methyl)-1-oxopropyl]amino-N-methyl-N-[(2'-nitro)[1,1'-biphenyl]-4-yl]benzenebutanamide The amine (210 mg; 0.54 mmol) from Step G, and N-Boc-α-methylalanine (138 mg; 0.68 mmol) were added to a solution of triethylamine (75 μl; 0.54 mmol) in methylene chloride (2 ml). BOP reagent (358 mg; 0.81 mmol) was added to the solution and the reaction mixture stirred at room temperature for 24 h. The reaction mixture was quenched by adding brine and then extracted with methylene chloride (3×5 ml). The combined extracts were dried using anhydrous magnesium sulfate powder, filtered and evaporated under reduced pressure. The residues were subjected to column chromatography on silica gel using an eluant comprising ethyl acetate and hexanes 2:1 v/v. The desired product was isolated as a yellowish glassy solid (301.2 mg; 97%). FAB-MS:- calculated for $C_{32}H_{38}N_4O_6$ 574.3 found 575.6 (M+1).

Step I: (R)-α-[(2-t-Butoxycarbonylamino-2-methyl)-1-oxopropyl]amino-N-methyl-N-[(2'-amino)[1,1'-biphenyl]-4-yl]benzenebutanamide The nitro compound (300 mg; 0.52 mmol) was dissolved in methanol (8 ml) and 10%-palladium on carbon (50 mg) added. The sample was hydrogenated at room temperature at 40 psi for 15 h. The spent hydrogenation catalyst was removed by filtration through a Celite bed, the bed carefully washed with methanol and methylene chloride. The combined filtrates were evaporated under vacuum to give a glassy solid (270.2 mg; 93.7%) which was the title amine.

Step J: (R)-α-[(2-Amino-2-methyl)-1-oxopropyl]amino -N-methyl-N-[(2'-[[(methylamino)carbonyl]amino][1,1'-biphenyl]-4-yl]benzenebutanamide, trifluoroacetate The amine (65 mg; 0.12 mmol) from Step I was dissolved in dry methylene chloride and reacted with methyl isocyanate (50 μl; 0.85 mmol) at room temperature. The reaction mixture was stirred overnight for 22 h. The volatiles were removed under vacuum to leave a thick gummy residue which was directly chromatographed on silica gel using a mixture of ethyl acetate and hexanes 1:1 v/v as eluant. The product (84 mg) was only partially purified after the chromatography and taken onto the deprotection step as is. The partially purified urea (80 mg) was dissolved in methanol (2 ml) and 9N-hydrochloric acid (1 ml) added at room temperature to the methanolic urea solution with stirring at room temperature for 2 h. The volatiles were removed using a slow nitrogen gas stream and the solid sample stored over the weekend. The product was isolated by hplc on a reversed phase C18 column using a solvent gradient of methanol and 0.1% aqueous trifluoroacetic acid, in this way, the desired product (36.8 mg; 49.9%) was isolated as a glassy solid.

$^1$H NMR (400 MHz, $CD_3OD$): 1.61 (s, 3H) 1.65 (s, 3H) 1.98 (q, 2H) 2.39 (m, 1H) 2.62 (m, 1H) 2.66 (s, 3H) 3.24 (s, 3H) 4.43 (t, 1H) 6.91 (d, 2H) 7.02 (t, 1H) 7.08 (t, 2H), 7.24–7.43 (m, 7H) 7.60 (d, 1H). FAB-MS:- calculated for $C_{29}H_{35}N_5O_3$ 501.3 found 502.6 (M+1).

EXAMPLE 34

(R)-α-[(2-Amino-2-methyl)-1-oxopropyl]amino-N -methyl-N -[2'-(1H -tetrazol-5-yl)[1,1'-biphenyl]-4-yl]butanamide, trifluoroacetate Step A: 4-[N-t-Butoxycarbonylaminol-2'-cyano-1,1'-biphenyl

[4-(t-Butoxycarbonylamino)phenyl]trimethylstannane (1.75 g; 4.92 mmol), 2-bromobenzonitrile (940 mg; 5.16 mmol) and tetakis(triphenylphosphine)palladium(0) were dissolved in dry THF (15 ml) and the resulting solution degassed using a freeze-vac-thaw cycle. The sample was heated to reflux and maintained at reflux for 72 h. The volatiles were removed and the residues were chromatographed on silica gel using a solvent mixture of diethyl ether and hexanes 1:9 v/v. The product was isolated as a white powder (695 mg; 48%). FAB-MS:- calculated for $C_{18}H_{18}N_2O_2$ 294.1; found 294.9 (M).

Step B: 4-[(N-t-Butoxycarbonyl)-N-methylamino]-2'-cyano-1, 1'-biphenyl

Dry potassium hydride powder (70 mg; 1.75 mmol) that had been freed from oil and dried under vacuum was suspended in dry THF (2 ml) at 0° C. under a nitrogen atmosphere and the carbamate obtained in Step A (400 mg; 1.36 mmol) added in small batches over 5 minutes. Gas evolution was observed and the solution became lemon yellow in color. The solution was stirred for 0.5 h at 0° C. and HMPA (236.5 μl; 1.36 mmol) added followed immediately by methyl iodide (210 μl; 3.37 mmol) during which the yellow color was discharged to give a milky white color. The reaction was maintained at 0° C. for 5 more minutes and then allowed gradually to warm to room temperature. The reaction was quenched with brine and extracted with diethyl ether (3×30 ml). The ethereal extracts were dried over magnesium sulfate, filtered and evaporated under partial vacuum. A colorless oil was obtained after evaporation which was subsequently purified by column chromatography on silica gel using a solvent mixture of diethyl ether and hexanes (1:2 v/v). The desired product (415.1 mg; 76.9%) was obtained as a colorless oil. FAB-MS:- calculated for $C_{19}H_{20}N_2O_2$ 308.2; found 308 (M).

Step C: 4-[N-methylamino]-2'-cyano-1,1'-biphenyl

The urethane from Step B (150 mg; 0.486 mmol) of this Example was dissolved in methylene chloride (1 ml) and stirred at room temperature. Anisole (0.5 ml) and TFA (0.5 ml) were added and the reaction mixture stirred at room temperature for 0.5 h. The volatiles were removed under reduced pressure and the residues dissolved up in chloroform and shaken with a volume of 10% aqueous solution of sodium carbonate, then water and the methylene chloride layer dried over potassium carbonate. The sample was filtered and the filtrates evaporated under partial vacuum to leave a residue that was further purified by silica gel chromatography using a solvent gradient of ethyl acetate and hexanes. In this way 86.2 mg (85%) of a pale yellow oil that slowly solidified on standing was obtained. FAB-MS:- calculated for $C_{14}H_{12}N_2$ 208.1 found 209.7 (M+1).

Step D: (R)-α-[Amino]-N-methyl-N-[(2'-cyano)-[1,1'-biphenyl]-4-yl]benzenebutanamide (R)-α-[N-(9-Fluorenylmethoxycarbonyl)amino]-benzenebutanoic acid (500 mg; 1.25 mmol), was converted into its corresponding acid chloride according to the procedure descibed in Example 33, Step F using 1 drop of DMF, oxalyl chloride (136 μl) in methylene chloride (2.5 ml). A yellow solid which was the acid chloride (525 mg) was obtained and used without further purification. A portion of the acid chloride (222.8 mg; 0.528 mmol) was added to 4-[N-methylamino]-2'-cyano-1,1'-biphenyl (110 mg; 0.528 mmol) were dissolved in methylene chloride (1 ml) and stirred together for 2 h at room temperature. Triethylamine (73.6 μl; 0.528 mmol) was added and the reaction mixture stirred for a further 6 h. The reaction was quenched with 4-(aminomethyl)-piperidine (0.5 ml) and stirred for 15 minutes and then partitioned between water and methylene chloride. The organic phase was separated, dried over powdered potassium carbonate. The volatiles were removed under reduced pressure and the residues chromatographed on silica gel using ethyl acetate and then ethyl acetate and methanol 9:1 v/v. The yield of the desired product was 60.2 mg (30.8%). FAB-MS:- calculated for $C_{24}H_{23}N_{3}O$ 369.2 found 370.0 (M+1).

Step E: (R)-α-[(2-t-Butoxycarbonylamino-2-methyl)-1-oxopropyl]amino-N-methyl-N-[(2'-cyano)[1,1'-biphenyl]-4-yl]-benzenebutanamide The amine from Step D (58 mg; 0.157 mmol) and N-Boc-α-methylalanine (32 mg; 0.157 mmol) were dissolved in dry methylene chloride along with triethylamine (43.8 µl; 0.314 mmol). BOP-reagent (69.4 mg; 0.157 mmol) was added and the resulting turbid solution stirred at room temperature overnight. The solvent was removed under reduced pressure and the residues chromatographed on silica gel using an eluant of ethyl acetate and hexanes 1:1 v/v. The product (63.1 mg; 72.5%) was isolated as a glass. FAB-MS:- calculated for $C_{33}H_{38}N_{4}O_{4}$ 554.3 found 555.7 (M+1).

Step F: (R)-α-[2-Amino-2-methyl-1-oxopropyl]amino-N-methyl-N-[2'-(1H-tetrazol-5-yl)[1,1'-biphenyl]-4-yl] butanamide, trifluoroacetate The nitrile (50 mg; 0.091 mmol) and trimethyltin azide (0.274 mmol) were mixed together in dry toluene (2 ml) and heated to gentle reflux for 72 h. The volatiles were remove on a rotary evaporator under vacuum and the waxy solid residues thus obtained was dissolved in methanol (2 ml). The methanol solution was stirred at room temperature and 9N-hydrochloric acid (0.5 ml) added. Stirring was maintained for 1.5 h then hexanes (1 ml) added, stirred vigorously into the aqueous methanol layer and then the hexanes layer was removed using a Pasteur pipette and discarded. The aqueous methanol solution was evaporated to dryness using a slow stream of nitrogen gas. The residues were then partially separated by hplc using a solvent gradient of methanol and 0.1% aqueous trifluoroacetic acid to give pure (R)-α-[2-amino-2-methyl-1-oxopropyl]amino-N-methyl-N-[2'-cyano][1,1'-biphenyl]-4-yl]butanamide trifluoroacetic acid salt (17.2 mg; 33.2%) which was the slower moving product material to come off the column.

$^{1}$H NMR (400 MHz, $CD_{3}OD$): 1.60 (s, 3H) 1.64 (s, 3H) 1.95 (m, 2H) 2.37 (m, 1H) 2.61 (m, 1H) 3.25 (s, 3H) 4.4 (d, 1H) 6.88 (d, 2H) 6.95 (t, 1H) 7.06 (t, 2H) 7.46 (d, 2H) 7.60 (m, 4H) 7.79 (t, 1H) 7.88 (d, 1H). FAB-MS:- calculated for $C_{28}H_{30}N_{4}O_{2}$ 454.2; found 455.4 (M+1). The faster moving major material that contained the tetrazole was repurified by hplc a second time using the same conditions to give the desired title compound (31.2 mg; 56%).

$^{1}$H NMR (400 MHz, $CD_{3}OD$): 1.59 (s, 3H) 1.62 (s, 3H) 1.90 (m, 2H) 2.36 (m, 1H), 2.56 (m, 1H) 3.20 (s, 3H) 4.37 (dd, 1H) 6.94 (d,2H) 7.00 (t, 1H) 7.11 (dd, 4H) 7.30 (d, 2H) 7.62 (t, 2H) 7.73 (m, 2H). FAB-MS:- calculated for $C_{28}H_{31}N_{7}O_{2}$ 497.3; found 498.6 (M+1).

EXAMPLE 35

(R)-α-[(2-Amino-2-methyl)-1-oxopropyl]amino-N-methyl-N-[(2'-[[(methylamino)carbonyl]amino) methyl][1,1'-biphenyl]-4-yl]benzenebutanamide, trifluoroacetate Step A: 1-Bromo-2[[[(methylamino)carbonyl]amino]-methyl]benzene 2-Bromobenzylamine hydrochloride salt 91.0 g; 4.49 mmol) was suspended in dry methylene chloride and triethylamine (1.41 ml; 10.12 mmol) added and most of the solid dissolved when stirring was initiated at room temperature. Methyl isocyanate (1.33 ml; 22.5 mmol) was gradually added over 5 minutes and then stirring of the resulting solution maintained for 6 h. The reaction was quenched by adding brine and extracting with methylene chloride (3×10 ml) and the combined extracts dried over potassium carbonate. After filtration and evaporation of volatiles, a solid off white material was obtained (0.84 g; 79%).

$^{1}$H NMR (400 MHz, $CD_{3}OD$): 2.69 (s, 3H) 4.34 (s, 2H) 7.12 (m, 1H) 7.28 (m, 2H) 7.52 (d, 1H). FAB-MS:- calculated for $C_{9}H_{11}BrN_{2}O$ 242/244 found 242.7/244.7 (M).

Step B: 4-[(N-(t-Butoxycarbonyl)-N-methyl)amino]-2'-[[( (methylamino)carbonyl)amino]methyl]-1,1'-biphenyl

[[4-[N-(t-Butoxycarbonyl)-N-methylamino]phenyl] trimethylstannane (178.4 mg; 0.48 mmol) and the N-methyl urea of 2-bromobenzylamine (117.2 mg; 0.48 mmol) were dissolved in anhydrous dioxane (8 ml) along with tetrakis (triphenylphosphine) palladium (0) (25 mg). The solution was degassed using a freeze-vac-thaw cycle and then heated to reflux under a nitrogen atmosphere for 24 h then set aside to cool. The reaction mixture was filtered through a Celite pad and evaporated under reduced pressure to give an orange colored oil. Chromatography of the oil using a solvent gradient comprising initially ethyl acetate and hexanes (1:1 v/v) then rising to ethyl acetate and hexanes (9:1 v/v) purified the crude product. In this manner 158.2 mg (88.8%) of a dark yellow oil was obtained.

$^{1}$H NMR (400 MHz, $CD_{3}OD$): 1.44 (s, 9H) 2.55 (d, 3H) 3.24 (s, 3H) 4.19 (d, 2H) 5.10 (s, 1H) 5.28 (s, 1H) 7.1–7.6 (m, 8H). FAB-MS:- calculated for $C_{21}H_{27}N_{3}O_{3}$ 369.2 found 370.0 (M+1).

Step C: 4-(N-Methyl)amino-2'-[[[(methylamino)carbonyl] amino]methyl]-1,1'-biphenyl The urea (155 mg; 0.42 mmol) from Step B of this Example and anisole (1 ml) were dissolved in dry methylene chloride (2 ml) and stirred at room temperature and TFA (1 ml) added. After being stirred together for 2 h, the volatiles were removed under reduced pressure and the residues dissolved in fresh methylene chloride (50 ml), washed with saturated sodium bicarbonate solution and then dried over magnesium sulfate. The solution was filtered and evaporated under reduced pressure and the oily residues chromatographed on silica gel using first ethyl acetate and hexanes (2:1 v/v) and then ethyl acetate and methanol 95:5 v/v. The product was isolated as a solid 102.4 mg (90%).

$^{1}$H NMR (400 MHz, $CD_{3}OD$): 2.60 (d, 3H) 2.81 (s, 3H) 4.28 (d, 2H) 6.60 and 7.10 (AA'BB', 4H) 7.15–7.65 (m, 4H). FAB-MS:- calculated for $C_{16}H_{19}N_{3}O$ 269.2 found 270 (M+1)

Step D: (R)-α-Amino-N-methyl-N-[2'-[[[(methylamino) carbonyl]amino]methyl][1,1'-biphenyl]-4-yl] benzenebutanamide The biphenyl amine (60 mg; 0.22 mmol) and triethylamine (39 µl; 0.28 mmol) were dissolved in dry methylene chloride (1 ml) and crude (R)-α-[N-(9-fluorenylmethoxycarbonyl)-amino]benzenebutanoyl chloride (94 mg; ca. 0.22 mmol) whose preparation is described as part of Step F of Example 33 and the biphenyl amine (60 mg; 0.22 mmol) was added and this reaction mixture stirred overnight at room temperature. The reaction mixture was stirred with excess 4-(aminomethyl)piperidine (0.5 ml) for 0.5 h and the resulting solution partitioned between water and methylene chloride. The methylene chloride phase was separated and dried over anhydrous powered potassium carbonate, filtered and evaporated under vacuum to give an oil. Chromatography on silica gel using an ethyl acetate and methanol gradient initially 4:1 then ending with 1:1 afforded the product as a glassy off white solid. The yield was 42.6 mg (45%). FAB-MS:- calculated for $C_{26}H_{30}N_{4}O_{2}$ 430.2 found 431.2 (M+1).

Step E: (R)-α-[(2-t-Butoxycarbonylamino-2-methyl)-1-oxopropyl]amino-N-methyl-N-[2'-[[((methylamino)carbonyl)amino]methyl][1,1'-biphenyl]-4-yl]benzenebutanamide The amine (45 mg; 0.105 mmol) from Step D of this Example, triethylamine (29.1 μl; 0.209 mmol) and N-Boc-α-methylalanine (21.3 mg; 0.104 mmol) were dissolved in dry methylene chloride (1 ml) and BOP-reagent added. The solution was stirred at room temperature overnight and the volatiles removed under vacuum. The residues were chromatographed on silica gel using neat ethyl acetate. The product was isolated as a powder with a yield of 52.4 mg (81%). FAB-MS:- calculated for $C_{35}H_{45}N_5O_5$ 615.3 found 616.4 (M+1).

Step F: (R)-α-[(2-Amino-2-methyl)-1-oxopropyl]amino-N-methyl-N-[(2'-[[(methylamino)carbonyl]amino)methyl][1,1'-biphenyl]-4-yl]-benzenebutanamide, trifluoroacetate The urea (30 mg; 0.049 mmol) from Step E of this Example was deprotected using 9N-hydrochloric acid in methanol (1 ml) in the presence of hexanes as similar to that desribed in Example 37, Step F. The crude material was purified by reversed phase hplc on a C18 column using a solvent gradient of methanol and 0.1% aqueous trifluoroacetic acid and 25.4 mg (82%) of the desired salt was isolated.

$^1$H NMR (400 MHz, CD$_3$OD): 1.59 (s, 3H) 1.64 (s, 3H) 1.97 (q, 2H) 2.38 (m, 1H) 2.62 (m, 1H) 2.68 (s, 3H) 3.25 (s, 3H) 4.23 (ABq, 2H) 4.45 (m, 1H) 6.94 (d, 2H) 7.04 (t, 1H) 7.11 (t, 2H) 7.23 (dd, 1H) 7.36 (m, 6H) 7.44 (d, 1H). FAB-MS:- calculated for $C_{30}H_{37}N_5O_3$ 515.3; found 516.7 (M+1).

EXAMPLE 36

The bioassay employed for the determination of growth hormone secretion in rat pituitary cell cultures has been previously described—Cheng, K.; Chan, W. W.-S; Barreto, A.; Convey, E. M.; Smith, R. G. Endocrinology 124: 2791-2798 (1989)—and is summarized here: The Wistar male rats (150-200 grams) were obtained from Charles River Laboratories (Wilmington, Mass). Rats were maintained at a constant temperature (25° C.) on a 14-hr light, 10-hr dark cycle. Rat chow and water were available ad libitum. The animals were sacrificed by decapitation and anterior lobes of the pituitary quickly removed. Rat pituitary cells were isolated from pituitaries by enzymatic digestion with 0.2% collagenase and 0.2% hyaluronidase in Hank's Balanced Salt Solution. For culture, the cells were suspended in culture medium and adjusted to 1.5×10$^5$ cells/ml, and 1.0 ml of this suspension was placed in each well of a 24-well tray (Costar, Cambridge, Mass.). Cells were maintained in a humidified 5% CO$_2$-95% air atmosphere at 37° C. for 3 to 4 days. The culture medium consisted of DMEM containing 0.37% NaHCO$_3$, 10% horse serum, 2.5% fetal bovine serum, 1% non-essential amino acids, 1% glutamine, 1% nystatin, and 0.1% gentamycin. On the day of an experiment, cells were washed twice 1½ hrs prior to and once more immediately before the start of the experiment with the above culture medium containing 25 mM HEPES, pH 7.4. GH release was initiated by adding 1 ml of fresh medium containing test agents to each well in quadruplicate. Incubation was carded out at 37° C. for 15 min. After incubation, medium was removed and centrifuged at 2,000×g for 15 min to remove any cellular material. The supernatant fluid was removed and assayed for GH content. Rat GH in culture medium was measured by a double antibody RIA procedure using materials obtained from Dr. A. F. Parlow (Harbor-UCLA medical Center, Torrance, Calif.) and expressed in terms of the standard rat GH RP-2. ED$_{50}$ values for test compounds were computed by fitting a four-parameter logistic function to the dose-response curve. Least squares estimates of the four-parameter logistic function coefficients and their variances were derived using the iterative algorithm described by Bates and Watts.

| Example No. | ED$_{50}$ | Example No. | ED$_{50}$ |
|---|---|---|---|
| 1 | >0.5 μM | 17 | >0.5 μM |
| 2 | <0.5 μM | 18 | >0.5 μM |
| 3 | <0.5 μM | 19 | >0.5 μM |
| 4 | >0.5 μM | 20 | <0.5 μM |
| 5 | >0.5 μM | 21 | <0.5 μM |
| 6 | >0.5 μM | 22 | <0.5 μM |
| 7a | <0.5 μM | 23 | >0.5 μM |
| 7b | >0.5 μM | 24 | >0.5 μM |
| 8a | >0.5 μM | 25 | >0.5 μM |
| 8b | >0.5 μM | 26 | >0.5 μM |
| 9 | <0.5 μM | 27 | >0.5 μM |
| 10 | <0.5 μM | 28 | >0.5 μM |
| 11 | <0.5 μM | 29 | >0.5 μM |
| 12 | <0.5 μM | 30 | >0.5 μM |
| 13 | >0.5 μM | 31 | >0.5 μM |
| 14 | <0.5 μM | 32 | >0.5 μM |
| 15 | >0.5 μM | 33 | >0.5 μM |
| 16 | >0.5 μM | 34 | <0.5 μM |
|  |  | 35 | <0.5 μM |

What is claimed is:
1. A compound of the formula:

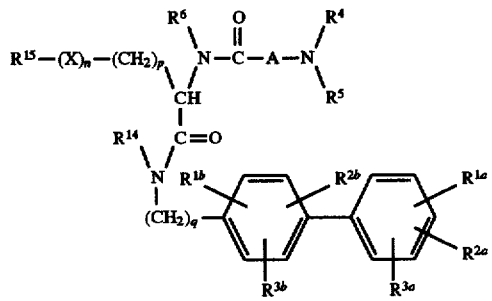

wherein:
n is 0 or 1;
p is 0, 1, 2, 3, 4, 5 or 6;
q is 0, 1, 2, 3, or 4;
X is C=O, O, S(O)$_m$,

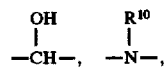

or —CH=CH—;
m is 0, 1 or 2;
$R^1$, $R^2$, $R^{1a}$, $R^{2a}$, $R^{1b}$, and $R^{2b}$ are independently selected from: hydrogen, halogen, $C_1$-$C_7$ alkyl, $C_1$-$C_3$ perfluoroalkyl, $C_1$-$C_3$ perfluoroalkoxy, —S(O)$_m$—R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$—NCOO(CH$_2$)$_v$—, phenyl, and substituted phenyl where the substituents on phenyl are selected from 1 to 3 of halogen, $C_1$-$C_6$ alkyl, $C_1$-$C_6$ alkoxy, and hydroxy, with the proviso that if q is 0 then at least one of R$^{1a}$, R$^{2a}$, and R$^{3a}$ is other than hydrogen;
v is 0, 1, 2 or 3;
R$^{3a}$ and R$^{3b}$ are independently selected from: hydrogen, R$^9$, $C_1$-$C_6$ alkyl substituted with R$^9$, phenyl substituted with R$^9$, and phenoxy substituted with R$^9$;

$R^4$, $R^{4a}$, $R^{4b}$, $R^5$ and $R^{5a}$ are independently selected from: hydrogen, $C_1$–$C_{10}$ alkyl, and substituted $C_1$–$C_{10}$ alkyl, where the substituents on the $C_1$–$C_{10}$ alkyl are selected from: 1 to 3 of hydroxy, $C_1$–$C_3$ alkoxy, fluoro, phenyl independently substituted with $R^1$ and $R^2$, $C_1$–$C_{20}$-alkanoyloxy, $C_1$–$C_5$ alkoxycarbonyl, and carboxy, or $R^4$ and $R^5$ can be taken together to form —$(CH_2)_r$B$(CH_2)_s$—, where B is $CHR^1$, O, $S(O)_m$ or $NR^{10}$, m is 0, 1 or 2, and r and s are independently 0, 1, 2, or 3;

$R^6$ is hydrogen, $C_1$–$C_{10}$ alkyl, phenyl or phenyl $C_1$–$C_{10}$ alkyl;

$R^{7a}$ and $R^{7b}$ are independently selected from: hydrogen; $C_1$–$C_3$ perfluoroalkyl; $C_1$–$C_6$ alkyl; phenyl; substituted $C_1$–$C_6$ alkyl, where the substituents on the $C_1$–$C_6$ alkyl are phenyl or substituted phenyl; and substituted phenyl where the substituents on the phenyl are selected from 1 to 3 of halogen, $C_1$–$C_6$ alkyl, $C_1$–$C_6$ alkoxy, and hydroxy;

$R^9$ is selected from:

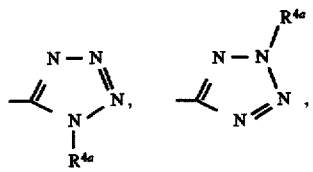

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{4b}R^{12c}N(CH_2)_v$—, $R^{12a}R^{12b}NCO(CH_2)_v$—, $R^{12a}R^{12b}NCS(CH_2)_v$—, $R^{4b}R^{12a}N$—$N(R^{12b})CO(CH_2)_v$—, $R^{4b}R^{12a}N$—$N(R^{12b})CS(CH_2)_v$—, $R^{4b}R^{12a}NCON(R^{12c})(CH_2)_v$—, $R^{4b}R^{12a}NCSN(R^{12c})(CH_2)_v$—, $R^{4b}R^{12a}N$—$N(R^{12b})CON(R^{12c})(CH_2)_v$—, $R^{4b}R^{12a}N$—$N(R^{12b})CSN(R^{12c})(CH_2)_v$—, $R^{4b}R^{12a}N$—$N(R^{12b})$—COO—$(CH_2)_v$—, $R^{4b}R^{12a}NCOO(CH_2)_v$—, and $R^{13}OCON(R^{12c})(CH_2)_v$—;

$R^{10}$ and $R^{11}$ are independently selected from: hydrogen, $C_1$–$C_6$ alkyl, phenyl $C_1$–$C_6$ alkyl, $C_1$–$C_5$-alkoxycarbonyl, and $C_1$–$C_5$-alkanoyl-$C_1$–$C_6$ alkyl;

$R^{12a}$, $R^{12b}$ and $R^{12c}$ are independently selected from: $R^{5a}$, $OR^{5a}$, and $COR^{5a}$; or $R^{12a}$ and $R^{12b}$, or $R^{12b}$ and $R^{12c}$, or $R^{12a}$ and $R^{12c}$, or $R^{4b}$ and $R^{12a}$, or $R^{4b}$ and $R^{12a}$, or $R^{4b}$ and $R^{12c}$, or $R^{13}$ and $R^{12c}$, may be taken together to form —$(CH_2)_r$—B—$(CH_2)_s$—;

where B is $CHR^1$, O, $S(O)_m$ or $NR^{10}$; m is 0, 1 or 2; and r and s are independently 0, 1, 2, or 3;

$R^{13}$ is selected from: $C_1$–$C_3$ perfluoroalkyl; $C_1$–$C_6$ alkyl; phenyl; substituted $C_1$–$C_6$ alkyl, where the substituents on $C_1$–$C_6$ alkyl are selected from: hydroxy, —$NR^{10}R^{11}$, carboxy, and phenyl; and substituted phenyl where the substituents on the phenyl are selected from 1 to 3 of halogen, $C_1$–$C_6$ alkyl, $C_1$–$C_6$ alkoxy, and hydroxy;

$R^{14}$ is selected from: hydrogen, phenyl independently substituted with $R^1$ and $R^2$, $C_1$–$C_{10}$ alkyl, and substituted $C_1$–$C_{10}$ alkyl where the substituents on the $C_1$–$C_{10}$ alkyl are selected from: 1 to 3 of imidazolyl, indolyl, hydroxy, fluoro, $S(O)_mR^{7a}$, $C_1$–$C_6$ alkoxy, $C_3$–$C_7$ cycloalkyl, phenyl $C_1$–$C_3$ alkoxy independently substituted with $R^1$ and $R^2$, phenyl independently substituted with $R^1$ and $R^2$, $C_1$–$C_5$ alkanoyloxy, $C_1$–$C_5$ alkoxycarbonyl, carboxy, formyl, and —$NR^{10}R^{11}$;

$R^{15}$ is selected from: hydrogen, trifluoromethyl, phenyl independently substituted with $R^1$ and $R^2$, naphthyl independently substituted with $R^1$ and $R^2$, $C_3$–$C_7$ cycloalkyl, $C_1$–$C_{10}$ alkyl, and substituted $C_1$–$C_{10}$ alkyl where the substituents on the $C_1$–$C_{10}$ alkyl are selected from: 1 to 3 of hydroxy, fluoro, $S(O)_mR^{7a}$, $C_1$–$C_6$ alkoxy, $C_3$–$C_7$ cycloalkyl, phenyl independently substituted with $R^1$ and $R^2$, phenyl $C_1$–$C_3$ alkoxy independently substituted with $R^1$ and $R^2$, naphthyl independently substituted with $R^1$ and $R^2$, naphthyl $C_1$–$C_3$ alkoxy independently substituted with $R^1$ and $R^2$, $C_1$–$C_5$ alkanoyloxy, $C_1$–$C_5$ alkoxycarbonyl, carboxy, formyl, —$NR^{10}R^{11}$, and heterocycle independently substituted with $R^1$ and $R^2$, wherein the heterocycle is selected from: imidazole, thiophene, furan, pyrrole, oxazole, thiazole, triazole, tetrazole, pyridine, benzofuran, benzothiophene, benzimidazole, indole, 7-azaindole, oxindole, and indazole;

A is:

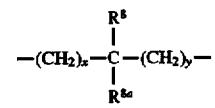

where x and y are independently 0, 1, 2, or 3;

$R^8$ and $R^{8a}$ are independently selected from: hydrogen, $C_1$–$C_{10}$ alkyl, trifluoromethyl, phenyl, and substituted $C_1$–$C_{10}$ alkyl where the substituents on the $C_1$–$C_{10}$ alkyl are selected from: 1 to 3 of imidazolyl, indolyl, hydroxy, fluoro, $S(O)_mR^{7a}$, $C_1$–$C_6$ alkoxy, $C_3$–$C_7$ cycloalkyl, phenyl independently substituted with $R^1$ and $R^2$, phenyl $C_1$–$C_3$ alkoxy independently substituted with $R^1$ and $R^2$, $C_1$–$C_5$ alkoxycarbonyl, carboxy, formyl, and —$NR^{10}R^{11}$; or $R^8$ and $R^{8a}$ may be taken together to form —$(CH_2)_t$— where t is 2, 3, 4, 5, or 6; or $R^8$ and $R^{8a}$ may independently be joined to one or both of $R^4$ and $R^5$ to form an alkylene bridge between the terminal nitrogen and the alkyl portion of the A group wherein the bridge contains from 1 to 5 carbon atoms;

and pharmaceutically acceptable salts thereof.

2. The compound of claim 1 wherein:

n is 0 or 1;

p is 0, 1, 2, 3, or 4;

q is 0, 1, or 2;

X is O, $S(O)_m$,

or —CH=CH—;

m is 0, 1 or 2;

$R^1$, $R^2$, $R^{1a}$, $R^{2a}$, $R^{1b}$, and $R^{2b}$ are independently selected from: hydrogen, halogen, $C_1$–$C_7$ alkyl, $C_1$–$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl, and substituted phenyl where the substituents on phenyl are selected from: 1 to 3 of halogen, $C_1$–$C_6$ alkyl, $C_1$–$C_6$ alkoxy, and hydroxy;

v is 0, 1 or 2;

$R^{3a}$ and $R^{3b}$ are independently selected from: hydrogen, $R^9$, $C_1$–$C_6$ alkyl substituted with $R^9$, phenyl substituted with $R^9$, and phenoxy substituted with $R^9$;

$R^4$, $R^{4a}$, $R^{4b}$, $R^5$ and $R^{5a}$ are independently selected from: hydrogen, $C_1$–$C_{10}$ alkyl, and substituted $C_1$–$C_{10}$ alkyl, where the substituents on the $C_1$–$C_{10}$ alkyl are selected from: 1 to 3 of hydroxy, $C_1$–$C_3$ alkoxy, fluoro, phenyl independently substituted with $R^1$ and $R^2$, $C_1$–$C_{20}$-alkanoyloxy, $C_1$–$C_5$ alkoxycarbonyl, and carboxy;

$R^6$ is hydrogen, $C_1$–$C_{10}$ alkyl, or phenyl $C_1$–$C_{10}$ alkyl;

$R^{7a}$ and $R^{7b}$ are independently selected from: hydrogen, $C_1$–$C_3$ perfluoroalkyl, $C_1$–$C_6$ alkyl, phenyl, and substituted $C_1$–$C_6$ alkyl, where the substituent on the $C_1$–$C_6$ alkyl is phenyl;

$R^9$ is selected from:

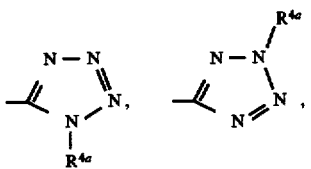

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_v CO$—, $R^{4b}R^{12c}N(CH_2)_v$—, $R^{12a}R^{12b}NCO(CH_2)_v$—, $R^{12a}R^{12b}NCS(CH_2)_v$—, $R^{4b}R^{12a}N$—$N(R^{12b})CO(CH_2)_v$—, $R^{4b}R^{12a}N$—$N(R^{12b})CS(CH_2)_v$—, $R^{4b}R^{12a}NCON(R^{12c})(CH_2)_v$—, $R^{4b}R^{12a}NCSN(R^{12c})(CH_2)_v$—, $R^{4b}R^{12a}N$—$N(R^{12b})CON(R^{12c})(CH_2)_v$—, $R^{4b}R^{12a}N$—$N(R^{12b})CSN(R^{12c})(CH_2)_v$—, $R^{4b}R^{12a}N$—$N(R^{12b})$—COO—$(CH_2)_v$—, $R^{4b}R^{12a}NCOO(CH_2)_v$—, and $R^{13}OCON(R^{12c})(CH_2)_v$—;

$R^{10}$ and $R^{11}$ are independently selected from: hydrogen, $C_1$–$C_6$ alkyl, and $C_1$–$C_5$ alkanoyl-$C_1$–$C_6$ alkyl;

$R^{12a}$, $R^{12b}$ and $R^{12c}$ are independently selected from: $R^{5a}$, $OR^{5a}$, and $COR^{5a}$; or $R^{12a}$ and $R^{12b}$, or $R^{12b}$ and $R^{12c}$, or $R^{4b}$ and $R^{12a}$, $R^{13}$ and $R^{12c}$ may be taken together to form —$(CH_2)_r$—B—$(CH_2)_s$—;

where B is $CHR^1$, O, $S(O)_m$ or $NR^{10}$, m is 0, 1 or 2, and r and s are independently 0, 1, 2, or 3;

$R^{13}$ is selected from: $C_1$–$C_3$ perfluoroalkyl; $C_1$–$C_6$ alkyl; phenyl; substituted $C_1$–$C_6$ alkyl, where the substituents on $C_1$–$C_6$ alkyl are selected from: hydroxy, —$NR^{10}R^{11}$, carboxy, and phenyl; and substituted phenyl where the substituents on the phenyl are selected from 1 to 3 of halogen, $C_1$–$C_6$ alkyl, $C_1$–$C_6$ alkoxy, and hydroxy;

$R^{14}$ is selected from: hydrogen, phenyl independently substituted with $R^1$ and $R^2$, $C_1$–$C_{10}$ alkyl, and substituted $C_1$–$C_{10}$ alkyl where the substituents on the $C_1$–$C_{10}$ alkyl are selected from: 1 to 3 of imidazolyl, indolyl, hydroxy, fluoro, $S(O)_m R^{7a}$, $C_1$–$C_6$ alkoxy, $C_3$–$C_7$ cycloalkyl, phenyl $C_1$–$C_3$ alkoxy independently substituted with $R^1$ and $R^2$, phenyl independently substituted with $R^1$ and $R^2$, $C_1$–$C_5$ alkanoyloxy, $C_1$–$C_5$ alkoxycarbonyl, carboxy, formyl, and —$NR^{10}R^{11}$;

$R^{15}$ is selected from: hydrogen, trifluoromethyl, phenyl independently substituted with $R^1$ and $R^2$, naphthyl independently substituted with $R^1$ and $R^2$, $C_3$–$C_7$ cycloalkyl, $C_1$–$C_{10}$ alkyl, and substituted $C_1$–$C_{10}$ alkyl where the substituents on the $C_1$–$C_{10}$ alkyl are selected from: 1 to 3 of hydroxy, fluoro, $S(O)_m R^{7a}$, $C_1$–$C_6$ alkoxy, $C_3$–$C_7$ cycloalkyl, phenyl independently substituted with $R^1$ and $R^2$, phenyl $C_1$–$C_3$ alkoxy independently substituted with $R^1$ and $R^2$, naphthyl independently substituted with $R^1$ and $R^2$, naphthyl $C_1$–$C_3$ alkoxy independently substituted with $R^1$ and $R^2$, $C_1$–$C_5$ alkanoyloxy, $C_1$–$C_5$ alkoxycarbonyl, carboxy, formyl, —$NR^{10}R^{11}$, and heterocycle independently substituted with $R^1$ and $R^2$, wherein the heterocycle is selected from: imidazole, thiophene, furan, pyrrole, oxazole, thiazole, triazole, tetrazole, pyridine, benzofuran, benzothiophene, benzimidazole, indole, 7-azaindole, oxindole, and indazole;

A is:

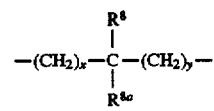

where x and y are independently 0, 1, or 2;

$R^8$ and $R^{8a}$ are independently selected from: hydrogen, $C_1$–$C_{10}$ alkyl, and substituted $C_1$–$C_{10}$ alkyl where the substituents on the $C_1$–$C_{10}$ alkyl are selected from: 1 to 3 of imidazolyl, indolyl, hydroxy, fluoro, $S(O)_m R^{7a}$, $C_1$–$C_6$ alkoxy, phenyl independently substituted with $R^1$ and $R^2$, $C_1$–$C_5$ alkoxycarbonyl, carboxy, formyl, and —$NR^{10}R^{11}$; or $R^8$ and $R^{8a}$ may be taken together to form —$(CH_2)_t$— where t is 2, 3 or 4; or $R^8$ and $R^{8a}$ may independently be joined to one or both of $R^4$ and $R^5$ to form an alkylene bridge between the terminal nitrogen and the alkyl portion of the A group wherein the bridge contains from 1 to 5 carbon atoms;

and pharmaceutically acceptable salts thereof.

3. The compound of claim 2 wherein:

n is 0 or 1;

p is 0, 1, 2, or 3;

q is 0, 1, or 2;

X is O, $S(O)_m$, or —CH=CH—;

m is 0 or 1;

$R^1$, $R^2$, $R^{1a}$, $R^{2a}$, $R^{1b}$, and $R^{2b}$ are independently selected from: hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl, and substituted phenyl where the substituents on phenyl are selected from: 1 to 3 of halogen, $C_1$–$C_6$ alkyl, $C_1$–$C_6$ alkoxy, and hydroxy;

v is 0, 1, or 2;

$R^{3a}$ and $R^{3b}$ are independently selected from: hydrogen, $R^9$, $C_1$–$C_6$ alkyl substituted with $R^9$, phenyl substituted with $R^9$, and phenoxy substituted with $R^9$;

$R^4$, $R^{4a}$, $R^{4b}$, $R^5$ and $R^{5a}$ are independently selected from: hydrogen, $C_1$–$C_{10}$ alkyl, and substituted $C_1$–$C_{10}$ alkyl, where the substituents on the $C_1$–$C_{10}$ alkyl are selected from: 1 to 3 of hydroxy, $C_1$–$C_3$ alkoxy, fluoro, phenyl independently substituted with $R^1$ and $R^2$, $C_1$–$C_{20}$-alkanoyloxy, $C_1$–$C_5$ alkoxycarbonyl, and carboxy;

$R^6$ is hydrogen or $C_1$–$C_{10}$ alkyl;

$R^{7a}$ and $R^{7b}$ are independently selected from: hydrogen, $C_1$–$C_6$ alkyl, and substituted $C_1$–$C_6$ alkyl, where the substituent on $C_1$–$C_6$ alkyl is phenyl;

$R^9$ is selected from:

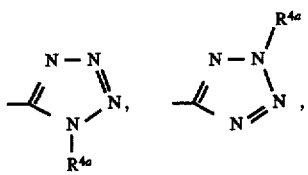

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{4b}R^{12c}N(CH_2)_v$—, $R^{12a}R^{12b}NCO(CH_2)_v$—, $R^{12a}R^{12b}NCS(CH_2)_v$—, $R^{4b}R^{12a}N$—$N(R^{12b})CO(CH_2)_v$—, $R^{4b}R^{12a}N$—$N(R^{12b})CS(CH_2)_v$—, $R^{4b}R^{12a}NCON(R^{12c})(CH_2)_v$—, $R^{4b}R^{12a}NCSN(R^{12c})(CH_2)_v$—, $R^{4b}R^{12a}N$—$N(R^{12b})CON(R^{12c})(CH_2)_v$—, $R^{4b}R^{12a}N$—$N(R^{12b})CSN(R^{12c})(CH_2)_v$—, $^{4b}R^{12a}N$—$N(R^{12b})$—COO—$(CH_2)_v$—, $R^{4b}R^{12a}NCOO(CH_2)_v$—, and $R^{13}OCON(R^{12c})(CH_2)_v$—;

$R^{10}$ and $R^{11}$ are independently selected from: hydrogen, $C_1$-$C_6$ alkyl, and $C_1$-$C_5$ alkanoyl-$C_1$-$C_6$ alkyl;

$R^{12a}$, $R^{12b}$ and $R^{12c}$ are independently selected from: $R^{5a}$, $OR^{5a}$, and $COR^{5a}$; or $R^{12a}$ and $R^{12b}$, or $R^{12b}$ and $R^{12c}$, or $R^{4b}$ and $R^{12a}$, $R^{13}$ and $R^{12c}$ may be taken together to form —$(CH_2)_r$—B—$(CH_2)_s$—;

where B is $CHR^1$, O, $S(O)_m$ or $NR^{10}$; m is 0, 1 or 2; and r and s are independently 0, 1, 2, or 3;

$R^{13}$ is selected from: $C_1$-$C_6$ alkyl; phenyl; substituted $C_1$-$C_6$ alkyl, where the substituents on $C_1$-$C_6$ alkyl are selected from: hydroxy, —$NR^1$ $OR^{11}$, carboxy, and phenyl; and substituted phenyl where the substituents on the phenyl are selected from 1 to 3 of halogen, $C_1$-$C_6$ alkyl, $C_1$-$C_6$ alkoxy, and hydroxy;

A is:

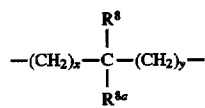

where x and y are independently 0, 1, or 2;

$R^8$ and $R^{8a}$ are independently selected from: hydrogen, $C_1$-$C_{10}$ alkyl, and substituted $C_1$-$C_{10}$ alkyl where the substituents on the $C_1$-$C_{10}$ alkyl are selected from: 1 to 3 of imidazolyl, indolyl, hydroxy, fluoro, $S(O)_mR^{7a}$, $C_1$-$C_6$ alkoxy, phenyl independently substituted with $R^1$ and $R^2$, $C_1$-$C_5$ alkoxycarbonyl, carboxy, formyl, and —$NR^{10}R^{11}$; or $R^8$ and $R^{8a}$ may be taken together to form —$(CH_2)_t$— where t is 2; or $R^8$ and $R^{8a}$ may independently be joined to one or both of $R^4$ and $R^5$ to form an alkylene bridge between the terminal nitrogen and the alkyl portion of the A group wherein the bridge contains from 1 to 5 carbon atoms;

and pharmaceutically acceptable salts thereof.

4. The compound of claim 3 wherein:

n is 0 or 1;

p is 0, 1 or 2;

q is 1;

X is O, $S(O)_m$ or —CH=CH—;

m is 0 or 1;

$R^1$, $R^2$, $R^{1a}$, $R^{2a}$, $R^{1b}$, and $R^{2b}$ are independently selected from: hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, phenyl, and substituted phenyl where the substituents on phenyl are selected from: 1 to 3 of halogen, $C_1$-$C_6$ alkyl, $C_1$-$C_6$ alkoxy, and hydroxy;

v is 0, 1 or 2;

$R^{3a}$ and $R^{3b}$ are independently selected from: hydrogen, $R^9$, and $C_1$-$C_6$ alkyl substituted with $R^9$;

$R^4$, $R^{4a}$, $R^{4b}$, $R^5$ and $R^{5a}$ are independently selected from: hydrogen, $C_1$-$C_{10}$ alkyl, and substituted $C_1$-$C_{10}$ alkyl, where the substituents on the $C_1$-$C_{10}$ alkyl are selected from: 1 to 3 of hydroxy, $C_1$-$C_3$ alkoxy, fluoro, phenyl independently substituted with $R^1$ and $R^2$, $C_1$-$C_{20}$-alkanoyloxy, $C_1$-$C_5$ alkoxycarbonyl, and carboxy;

$R^6$ is hydrogen;

$R^{7a}$ and $R^{7b}$ are independently selected from: hydrogen, $C_1$-$C_6$ alkyl, and substituted $C_1$-$C_6$ alkyl, where the substituent on $C_1$-$C_6$ alkyl is phenyl;

$R^9$ is selected from:

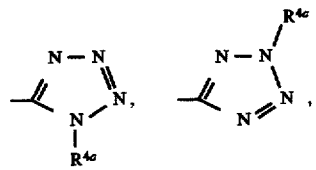

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^{4b}R^{12c}N(CH_2)_v$—, $R^{12a}R^{12b}NCO(CH_2)_v$—, $R^{12a}R^{12b}NCS(CH_2)_v$—, $R^{4b}R^{12a}N$—$N(R^{12b})CO(CH_2)_v$—, $R^{4b}R^{12a}N$—$N(R^{12b})CS(CH_2)_v$—, $R^{4b}R^{12a}NCON(R^{12c})(CH_2)_v$—, $R^{4b}R^{12a}NCSN(R^{12c})(CH_2)_v$—, $R^{4b}R^{12a}N$—$N(R^{12b})CON(R^{12c})(CH_2)_v$—, $R^{4b}R^{12a}N$—$N(R^{12b})CSN(R^{12c})(CH_2)_v$—, $^{4b}R^{12a}N$—$N(R^{12b})$—COO—$(CH_2)_v$—, $R^{4b}R^{12a}NCOO(CH_2)_v$—, and $R^{13}OCON(R^{12c})(CH_2)_v$—;

$R^{10}$ is selected from: hydrogen, $C_1$-$C_6$ alkyl, and $C_1$-$C_5$ alkanoyl-$C_1$-$C_6$ alkyl;

$R^{12a}$, $R^{12b}$ and $R^{12c}$ are independently selected from: $R^{5a}$, $OR^{5a}$, and $COR^{5a}$; or $R^{12b}$ and $R^{12c}$, or $R^{4b}$ and $R^{12a}$, $R^{13}$ and $R^{12c}$ may be taken together to form —$(CH_2)_r$—B—$(CH_2)_s$—;

where B is $CHR^1$, O, $S(O)_m$ or $NR^{10}$, m is 0, 1 or 2, and r and s are independently 0, 1, or 2;

$R^{13}$ is selected from: $C_1$-$C_6$ alkyl; phenyl; substituted $C_1$-$C_6$ alkyl, where the substituents on $C_1$-$C_6$ alkyl is phenyl; and substituted phenyl where the substituents on the phenyl are selected from 1 to 3 of halogen, $C_1$-$C_6$ alkyl, $C_1$-$C_6$ alkoxy, and hydroxy;

A is:

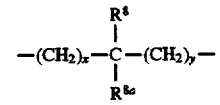

where x and y are independently 0 or 1;

$R^8$ and $R^{8a}$ are independently selected from: hydrogen, $C_1$-$C_{10}$ alkyl, and substituted $C_1$-$C_{10}$ alkyl where the substituents on the $C_1$-$C_{10}$ alkyl are selected from: 1 to 3 of imidazolyl, indolyl, hydroxy, fluoro, $S(O)_mR^{7a}$, $C_1$-$C_6$ alkoxy, phenyl independently substituted with $R^1$ and $R^2$, $C_1$-$C_5$ alkoxycarbonyl, carboxy, formyl, and —$NR^{10}R^{11}$; or $R^8$ and $R^{8a}$ may be taken together to form —$(CH_2)_t$— where t is 2; or $R^8$ and $R^{8a}$ may independently be joined to one or both of R⁴ and R⁵ to form an alkylene bridge between the terminal nitrogen and the alkyl portion of the A group wherein the bridge contains from 1 to 5 carbon atoms;

and pharmaceutically acceptable salts thereof.

5. The stereospecific compound of claim 1 of the structural formula:

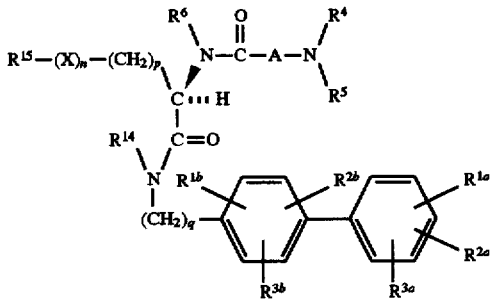

wherein $R^{1a}$, $R^{1b}$, $R^{2a}$, $R^{2b}$, $R^{3a}$, $R^{3b}$, $R^4$, $R^5$, $R^6$, $R^{14}$, $R^{15}$, A, n, p, q, and X are as defined in claim 1.

6. A compound which is selected from the group consisting of:

(R)-α-[(3-Amino-3-methyl-1-oxobutyl)amino]-N-[[2'-(1H-tetrazol-5-yl)-[1,1'-biphenyl]-4-yl]methyl]benzenebutanamide;

(R)-α-[(2-Amino-2-methyl-1-oxopropyl)amino]-N-[[2'-(1H-tetrazol-5-yl)[1,1'-biphenyl]-4-yl]methyl]benzenebutanamide;

(R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]benzenebutanamide;

(R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]benzenebutanamide;

(R)-α-[(3-Amino-3-methyl-1-oxobutyl)amino]-N-[[2'-(1H-tetrazol-5-yl)[1,1'-biphenyl]-4-yl]methyl]benzenepentanamide;

(R)-α-[(2-Amino-2-methyl-1-oxopropyl)amino]-N-[[2'-(1H-tetrazol-5-yl)[1,1'-biphenyl]-4-yl]methyl]benzenepentanamide;

(R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]benzenepentanamide;

(R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]benzenepentanamide;

(R)-α-[(3-Amino-3-methyl-1-oxobutyl)amino]-N-[[2'-(1H-tetrazol-5-yl)[1,1'-biphenyl]-4-yl]-methyl]-1H-indole-3-propanamide;

(R)-α-[(2-Amino-2-methyl-1-oxopropyl)amino]-N-[[2'-(1H-tetrazol-5-yl)[1,1'-biphenyl]-4oyl]-methyl]-1H-indole-3-propanamide;

(R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]-1H-indole-3-propanamide;

(R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]-1H-indole-3-propanamide;

(R)-α-[(3-Amino-3-methyl-1-oxobutyl)amino]-N-[[2'-(1H-tetrazol-5-yl)[1,1'-biphenyl]-4-yl]-methyl]-3-[(phenylmethyl)oxy]propanamide;

(R)-α-[(2-Amino-2-methyl-1-oxopropyl)amino]-N-[[2'-(1H-tetrazol-5-yl)[1,1'-biphenyl]-4-yl]-methyl]-3-[(phenylmethyl)oxy]propanamide;

(R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]-3-[(phenylmethyl)oxy]propanamide;

(R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]-3-[(phenylmethyl)oxy]propanamide;

(R)-α-[(3-Amino-3-methyl-1-oxobutyl)amino]-N-[[2'-(1H-tetrazol-5-yl)[1,1'-biphenyl]-4-yl]-methyl]-3-[(2,6-difluorophenyl)methyl]oxy]propanamide;

(R)-α-[(2-Amino-2-methyl-1-oxopropyl)amino]-N-[[2'-(1H-tetrazol-5-yl)[1,1'-biphenyl]-4-yl]-methyl]-3-[(2,6-difluorophenyl)methyl]oxy]propanamide;

(R)-α-[[3-[2(R)-Hydroxypropyl]amino-3-methyl-1-oxobutyl]amino]-N-[[2'-(1H-tetrazol-5-yl)[1,1'-biphenyl]-4-yl]methyl]-3-[[(2,6-difluorophenyl)methyl]oxy]propanamide;

(R)-α-[[3-[2(S),3-Dihydroxypropyl]amino-3-methyl-1-oxobutyl]amino]-N-[[2'-(1H-tetrazol-5-yl)[1,1'-biphenyl]-4-yl]methyl]-3-[[(2,6-difluorophenyl)-methyl]oxy]propanamide;

(R)-4'-[[[2-[(3-Amino-3-methyl-1-oxobutyl)amino]-1-oxo-4-phenylbutyl]amino]methyl]-N-ethyl [1,1'-biphenyl]-2-carboxamide;

(R)-4'-[[[2-[(2-Amino-2-methyl-1-oxopropyl)amino]-1-oxo-4-phenylbutyl]amino]methyl]-N-ethyl [1,1'-biphenyl]-2-carboxamide;

(R)-4'-[[[2-[[3-[2 (R)-Hydroxypropyl]amino-3-methyl-1-oxobutyl]amino]-1-oxo-4-phenylbutyl]amino]methyl]-N-ethyl[1,1'-biphenyl]-2-carboxamide;

(R)-4'-[[[2-[[3-[2(S),3-Dihydroxypropyl]amino-3-methyl-1-oxobutyl]amino]-1-oxo-4-phenylbutyl]amino]methyl]-N-ethyl [1,1'-biphenyl]-2-carboxamide;

(R)-4'-[[[2-[(3-Amino-3-methyl-1-oxobutyl)amino]-1-oxo-5-phenylpentyl]amino]methyl]-N-ethyl [1,1'-biphenyl]-2-carboxamide;

(R)-4'-[[[2-[(2-Amino-2-methyl-1-oxopropyl)amino]-1-oxo-5-phenylpentyl]amino]methyl]-N-ethyl [1,1'-biphenyl]-2-carboxamide;

(R)-4'-[[[2-[[3-[2(R)-Hydroxypropyl]amino-3-methyl-1-oxobutyl]amino]-1-oxo-5-phenylpentyl]amino]methyl]-N-ethyl[1,1'-biphenyl]-2-carboxamide;

(R)-4'-[[[2-[[3-[2(S),3-Dihydroxypropyl]amino-3-methyl-1-oxobutyl]amino]-1-oxo-5-phenylpentyl]amino]methyl]-N-ethyl[1,1'-biphenyl]-2-carboxamide;

(R)-4'-[[[2-[(3-Amino-3-methyl-1-oxobutyl)amino]-1-oxo-3-(1H-indole-3-yl)propyl]amino]methyl]-N-ethyl [1,1'-biphenyl]-2-carboxamide;

(R)-4'-[[[2-[(2-Amino-2-methyl-1-oxopropyl)amino]-1-oxo-3-(1H-indole-3-yl)propyl]amino]-methyl]-N-ethyl [1,1'-biphenyl]-2-carboxamide;

(R)-4'-[[[2-[[3-[2(R)-Hydroxypropyl]amino-3-methyl-1-oxobutyl]amino]-1-oxo-3-(1H-indole-3-yl)propyl]amino]methyl]-N-ethyl[1,1'-biphenyl]-2-carboxamide;

(R)-4'-[[[2-[[3-[2 (S),3-Dihydroxypropyl]amino-3-methyl-1-oxobutyl]amino]-1-oxo-3-(1H-indole-3-yl)propyl]amino]methyl]-N-ethyl[1,1'-biphenyl]-2-carboxamide;

(R)-4'-[[[2-[(3-Amino-3-methyl-1-oxobutyl)amino]-1-oxo-3-[(phenylmethyl)oxy]propyl]amino]methyl]-N-ethyl [1,1'-biphenyl]-2-carboxamide;

(R)-4'-[[[2-[(2-Amino-2-methyl-1-oxopropyl) amino]-1-oxo-3-[(phenylmethyl)oxy]propyl]amino]methyl]-N-ethyl[1,1'-biphenyl]-2-carboxamide;

(R)-4'-[[[2-[[3-[2 (R)-Hydroxypropyl]amino-3-methyl-1-oxobutyl]amino]-1-oxo-3-[(phenylmethyl)oxy]propyl]amino]methyl]-N-ethyl[1,1'-biphenyl]-2-carboxamide;

(R)-4'-[[[2-[[3-[2 (S),3-Dihydroxypropyl]amino-3-methyl-1-oxobutyl]amino]-1-oxo-3-[(phenylmethyl)oxy]propyl]amino]methyl]-N-ethyl [1,1'-biphenyl]-2-carboxamide;

(R)-4'-[[[2-[(3-Amino-3-methyl-1-oxobutyl)amino]-1-oxo-3-[[(2,6-difluorophenyl)methyl]oxy]propyl]amino]methyl]-N-ethyl[1,1'-biphenyl]-2-carboxamide;

(R)-4'-[[[2-[(2-Amino-2-methyl-1-oxopropyl)amino]-1-oxo-3-[[(2,6-difluorophenyl)methyl]oxy]propyl]amino]methyl]-N-ethyl[1,1'-biphenyl]-2-carboxamide;

(R)-4'-[[[2-[[3-[2(R)-Hydroxypropyl]amino-3-methyl-1-oxobutyl]amino]-1-oxo-3-[[(2,6-difluorophenyl)methyl]oxy]propyl]amino]methyl]-N-ethyl-[1,1'-biphenyl]-2-carboxamide;

(R)-4'-[[[2-[[3-[2(S),3-Dihydroxypropyl]amino-3-methyl-1-oxobutyl]amino]-1-oxo-3-[[(2,6-difluorophenyl)methyl]oxy]propyl]amino]methyl]-N-ethyl-[1,1'-biphenyl]-2-carboxamide;

(R)-α-[(3-Amino-3-methyl-1-oxobutyl)amino]-N-[[2'-[[(methylamino)carbonyl]amino][1,1'-biphenyl]-4-yl]methyl]benzenebutanamide;

(R)-α-[(2-Amino-2-methyl-1-oxopropyl)amino]-N-[[2'-[[(methylamino)carbonyl]amino][1,1'-biphenyl]-4-yl]methyl]benzenebutanamide;

(R)-α-[[3-[2(R)-Hydroxypropyl]amino-3-methyl-1-oxobutyl]-amino]-N-[[2'-[[(methylamino)carbonyl]amino][1,1'-biphenyl]-4-yl]methyl]benzenebutanamide;

(R)-α-[[3-[2(S),3-Dihydroxypropyl]amino-3-methyl-1-oxobutyl]amino]-N-[[2'-[[(methylamino)carbonyl]-amino][1,1'-biphenyl]-4-yl]methyl]benzenebutanamide;

(R)-α-[(3-Amino-3-methyl-1-oxobutyl)amino]-N-[[2'-[[(methylamino)carbonyl]amino][1,1'-biphenyl]-4-yl]methyl]benzenepentanamide;

(R)-α-[(2-Amino-2-methyl-1-oxopropyl)amino]-N-[[2'-[[(methylamino)carbonyl]amino][1,1'-biphenyl]-4-yl]methyl]benzenepentanamide;

(R)-α-[[3-[2(R)-Hydroxypropyl]amino-3-methyl-1-oxobutyl]amino]-N-[[2'-[[(methylamino)carbonyl]-amino][1,1'-biphenyl]-4-yl]methyl]benzenepentanamide;

(R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]benzenepentanamide;

(R)-α-[(3-Amino-3-methyl-1-oxobutyl)amino]-N-[[2'-[[(methylamino)carbonyl]amino][1,1'-biphenyl]-4-yl]methyl]-1H-indole-3-propanamide;

(R)-α-[(2-Amino-2-methyl-1-oxopropyl)amino]-N-[[2'-[[(methylamino)carbonyl]amino][1,1'-biphenyl]-4-yl]methyl]-1H-indole-3-propanamide;

(R)-α-[[3-[2(R)-Hydroxypropyl]amino-3-methyl-1-oxobutyl]amino]-N-[[2'-[[(methylamino)carbonyl]amino][1,1'-biphenyl]-4-yl]methyl]-1H-indole-3-propanamide;

(R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]-1H-indole-3-propanamide;

(R)-α-[(3-Amino-3-methyl-1-oxobutyl)amino]-N-[[2'-[[(methylamino)carbonyl]amino][1,1'-biphenyl]-4-yl]methyl]-3-[(phenylmethyl)oxy]propanamide;

(R)-α-[(2-Amino-2-methyl-1-oxopropyl)amino]-N-[[2'-[[(methylamino)carbonyl]amino][1,1'-biphenyl]-4-yl]methyl]-3-[(phenylmethyl)oxy]propanamide;

(R)-a-[[3-[2(R)-Hydroxypropyl]amino-3-methyl-1-oxobutyl]amino]-N-[[2'-[[(methylamino)carbonyl]amino][1,1'-biphenyl]-4-yl]methyl]-3-[(phenylmethyl)oxy]propanamide;

(R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]-3-[(phenylmethyl)oxy]propanamide;

(R)-α-[(3-Amino-3-methyl-1-oxobutyl)amino]-N-[[2'-[[(methylamino)carbonyl]amino][1,1'-biphenyl]-4-yl]methyl]-3-[[(2,6-difluorophenyl)methyl]oxy]propanamide (R)-α-[(2-Amino-2-methyl-1-oxopropyl)amino]-N-[[2'-[[(methylamino)carbonyl]amino][1,1'-biphenyl]-4-yl]methyl]-3-[[(2,6-difluorophenyl)methyl]oxy]propanamide;

(R)-α-[[3-[2(R)-Hydroxypropyl]amino-3-methyl-1-oxobutyl]amino]-N-[[2'-[[(methylamino)carbonyl]amino][1,1'-biphenyl]-4-yl]methyl]-3-[[(2,6-difluorophenyl)methyl]oxy]propanamide;

(R)-α-[[3-[2(S),3-Dihydroxypropyl]amino-3-methyl-1-oxobutyl]amino]-N-[[2'-[[(methylamino)carbonyl]amino][1,1'-biphenyl]-4-yl]methyl]-3-[[(2,6-difluorophenyl)methyl]oxy]propanamide;

(R)-α-[(3-Amino-3-methyl-1-oxobutyl)amino]-N-[[2'-hydroxymethyl[1,1'-biphenyl]-4-yl]methyl]benzenebutanamide;

(R)-α-[(2-Amino-2-methyl-1-oxopropyl)amino]-N-[[2'-hydroxymethyl[1,1'-biphenyl]-4-yl]methyl]benzenebutanamide;

(R)-α-[[3-[2(R)-Hydroxypropyl]amino-3-methyl-1-oxobutyl]amino]-N-[[2'-hydroxymethyl[1,1'-biphenyl]-4-yl]methyl]benzenebutanamide;

(R)-α-[[3-[2(S),3-Dihydroxypropyl]amino-3-methyl-1-oxobutyl]amino]-N-[[2'-hydroxymethyl[1,1'-biphenyl]-4-yl]methyl]benzenebutanamide;

(R)-α-[(3-Amino-3-methyl-1-oxobutyl)amino]-N-[[2'-hydroxymethyl[1,1'-biphenyl]-4-yl]methyl]benzenepentanamide;

(R)-α-[(2-Amino-2-methyl-1-oxopropyl)amino]-N-[[2'-hydroxymethyl[1,1'-biphenyl]-4-yl]methyl]benzenepentanamide;

(R)-α-[[3-[2(R)-Hydroxypropyl]amino-3-methyl-1-oxobutyl]amino]-N-[[2'-hydroxymethyl [1,1'-biphenyl]-4-yl]methyl]benzenepentanamide;

(R)-α-[[3-[2(S),3-Dihydroxypropyl]amino-3-methyl-1-oxobutyl]amino]-N-[[2'-hydroxymethyl[1,1'-biphenyl]-4-yl]methyl]benzenepentanamide;

(R)-α-[(3-Amino-3-methyl-1-oxobutyl)amino]-N-[[2'-hydroxymethyl[1,1'-biphenyl]-4-yl]methyl]-1H-indole-3-propanamide;

(R)-α-[(2-Amino-2-methyl-1-oxopropyl)amino]-N-[[2'-hydroxymethyl[1,1'-biphenyl]-4-yl]methyl]-1H-indole-3-propanamide;

(R)-α-[[3-[2(R)-Hydroxypropyl]amino-3-methyl-1-oxobutyl]amino]-N-[[2'-hydroxymethyl [1,1'-biphenyl]-4-yl]methyl]-1H-indole-3-propanamide;

(R)-α-[[3-[2(S)-Dihydroxypropyl]amino-3-methyl-1-oxobutyl]amino]-N-[[2'-hydroxymethyl [1,1'-biphenyl]-4-yl]methyl]-1H-indole-3-propanamide;

(R)-α-[(3-Amino-3-methyl-1-oxobutyl)amino]-N-[[2'-hydroxymethyl[1,1'-biphenyl]-4-yl]methyl]-3-[(phenylmethyl)oxy]propanamide;

(R)-α-[(2-Amino-2-methyl-1-oxopropyl)amino]-N-[[2'-hydroxymethyl[1,1'-biphenyl]-4-yl]methyl]-3-[(phenylmethyl)oxy]propanamide;

(R)-α-[[3-[2(R)-Hydroxypropyl]amino-3-methyl-1-oxobutyl]amino]-N-[[2'-hydroxymethyl[1,1'-biphenyl]-4-yl]methyl]-3-[(phenylmethyl)oxy]propanamide;

(R)-α-[[3-[2(S),3-Dihydroxypropyl]amino-3-methyl-1-oxobutyl]amino]-N-[[2'-hydroxymethyl [1,1'-biphenyl]-4-yl]methyl]-3-[(phenylmethyl)oxy]propanamide;

(R)-α-[(3-Amino-3-methyl-1-oxobutyl)amino]-N-[[2'-hydroxymethyl[1,1'-biphenyl]-4-yl]methyl]-3-[[(2,6-difluorophenyl)methyl]oxy]propanamide;

(R)-α-[(2-Amino-2-methyl-1-oxopropyl)amino]-N-[[2'-hydroxymethyl[1,1'-biphenyl]-4-yl]methyl]-3-[[(2,6-difluorophenyl)methyl]oxy]propanamide;

(R)-α-[[3-[2(R)-Hydroxypropyl]amino-3-methyl-1-oxobutyl]amino]-N-[[2'-hydroxymethyl[1,1'-biphenyl]-4-yl]methyl]-3-[[(2,6-difluorophenyl)methyl]oxy]propanamide;

(R)-α-[[3-[2(S),3-Dihydroxypropyl]amino-3-methyl-1-oxobutyl]amino]-N-[[2'-hydroxymethyl[1,1'-biphenyl]-4-yl]methyl]-3-[[(2,6-difluorophenyl)methyl]oxy]propanamide;

(R)-α-[(3-Amino-3-methyl-1-oxobutyl)amino]-N-[[2'-[[[(methylamino)carbonyl]amino]methyl]-[1,1'-biphenyl]-4-yl]methyl]benzenebutanamide;

(R)-α-[(2-Amino-2-methyl-1-oxopropyl)amino]-N-[[2'-[[[(methylamino)carbonyl]amino]methyl]-[1,1'-biphenyl]-4-yl]methyl]benzenebutanamide;

(R)-α-[[3-[2(R)-Hydroxypropyl]amino-3-methyl-1-oxobutyl]amino]-N-[[2'-[[[(methylamino)carbonyl]amino]methyl][1,1'-biphenyl]-4-yl]methyl]benzenebutanamide;

(R)-α-[[3-[2(S),3-Dihydroxypropyl]amino-3-methyl-1-oxobutyl]amino]-N-[[2'-[[[(methylamino)carbonyl]amino]methyl][1,1'-biphenyl]-4-yl]methyl]benzenebutanamide;

(R)-α-[(3-Amino-3-methyl-1-oxobutyl)amino]-N-[[2'-[[[(methylamino)carbonyl]amino]methyl]-[1,1'-biphenyl]-4-yl]methyl]benzenepentanamide;

(R)-α-[(2-Amino-2-methyl-1-oxopropyl)amino]-N-[[2'-[[[(methyl-amino)carbonyl]amino]methyl]-[1,1'-biphenyl]-4-yl]methyl]-benzenepentanamide;

(R)-α-[[3-[2(R)-Hydroxypropyl]amino-3-methyl-1-oxobutyl]amino]-N-[[2'-[[[(methylamino)carbonyl]-amino]methyl][1,1'-biphenyl]-4-yl]methyl]benzenepentanamide;

(R)-α-[[3-[2(S),3-Dihydroxypropyl]amino-3-methyl-1-oxobutyl]amino]-N-[[2'-[[[(methylamino)carbonyl]amino]methyl][1,1'-biphenyl]-4-yl]methyl]benzenepentanamide;

(R)-α-[(3-Amino-3-methyl-1-oxobutyl)amino]-N-[[2'-[[[(methylamino)carbonyl]amino]methyl]-[1,1'-biphenyl]-4-yl]methyl]-1H-indole-3-propanamide;

(R)-α-[(2-Amino-2-methyl-1-oxopropyl)amino]-N-[[2'-[[[(methyl-amino)carbonyl]amino]methyl]-[1,1'-biphenyl]-4-yl]methyl]-1H-indole-3-propanamide;

(R)-α-[[3-[2(R)-Hydroxypropyl]amino-3-methyl-1-oxobutyl]amino]-N-[[2'-[[[(methylamino)carbonyl]amino]methyl][1,1'-biphenyl]-4-yl]methyl]-1H-indole-3-propanamide;

(R)-α-[[3-[2(S),3-Dihydroxypropyl]amino-3-methyl-1-oxobutyl]amino]-N-[[2'-[[[(methylamino)carbonyl]amino]methyl][1,1'-biphenyl]-4-yl]methyl]-1H-indole-3-propanamide;

(R)-α-[(3-Amino-3-methyl-1-oxobutyl)amino]-N-[[2'-[[[(methylamino)carbonyl]amino]methyl]-[1,1'-biphenyl]-4-yl]methyl]-3-[(phenylmethyl)-oxy]propanamide;

(R)-α-[(2-Amino-2-methyl-1-oxopropyl)amino]-N-[[2'-[[[(methyl-amino)carbonyl]amino]methyl]-[1,1'-biphenyl]-4-yl]methyl]-3-[(phenylmethyl)-oxy]propanamide;

(R)-α-[[3-[2(R)-Hydroxypropyl]amino-3-methyl-1-oxobutyl]amino]-N-[[2'-[[[(methylamino)carbonyl]amino]methyl][1,1'-biphenyl]-4-yl]methyl]-3-[(phenylmethyl)oxy]propanamide;

(R)-α-[[3-[2(S),3-Dihydroxypropyl]amino-3-methyl-1-oxobutyl]amino]-N-[[2'-[[[(methylamino)carbonyl]amino]methyl][1,1'-biphenyl]-4-yl]methyl]-3-[(phenylmethyl)oxy]propanamide;

(R)-α-[(3-Amino-3-methyl-1-oxobutyl)amino]-N-[[2'-[[[(methylamino)carbonyl]amino]methyl][1,1'-biphenyl]-4-yl]methyl]-3-[[(2,6-difluorophenyl)-methyl]oxy]propanamide;

(R)-α-[(2-Amino-2-methyl-1-oxopropyl)amino]-N-[[2'-[[[(methyl-amino)carbonyl]amino]methyl]-[1,1'-biphenyl]-4-yl]methyl]-3-[[(2,6-difluoro-phenyl)methyl]oxy]propanamide;

(R)-α-[[3-[2(R)-Hydroxypropyl]amino-3-methyl-1-oxobutyl]amino]-N-[[2'-[[[(methylamino)carbonyl]amino]methyl][1,1'-biphenyl]-4-yl]methyl]-3-[[(2,6-difluorophenyl)methyl]oxy]propanamide;

(R)-α-[[3-[2(S),3-Dihydroxypropyl]amino-3-methyl-1-oxobutyl]amino]-N-[[2'-[[[(methylamino)carbonyl]amino]methyl][1,1'-biphenyl]- 4-yl]methyl]-3-[[(2,6-difluorophenyl)methyl]oxy]propanamide;

(R)-α-[(3-Amino-3-methyl-1-oxobutyl)amino]-N-[[2'-(1H-tetrazol-5-yl)[1,1'-biphenyl]-4-yl]methyl]benzene-propanamide;

(R)-α-[(2-Amino-2-methyl-1-oxypropyl)amino]-N-methyl-N-[[2'-(1H-tetrazol-5-yl)-[1,1'-biphenyl]-4-yl]methyl]benzenebutenamide;

(R)-α-[(2-amino-2-methyl-1-oxypropyl)amino]-N-[[2'-cyano-[1,1'-biphenyl]-4-yl]methyl]-N-methyl-benzenebutenamide;

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]benzenebutanamide;

(R)-α-[(3-Amino-3-methyl-1-oxybutyl)amino]-N-methyl-N-[[(2'-[([methylamino)carbonyl]amino]methyl]-[1,1'-biphenyl]-4-yl]methyl]benzenebutanamide;

(R)-α-[(4-Amino-4-methyl-1-oxopentyl)amino]-N-methyl-N-[[2'-(1H-tetrazol-5-yl)[1,1'-biphenyl]-4-yl]methyl]benzenebutanamide;

(R)-α-[(4-Amino-4-methyl-1-oxypentyl)amino]-N-methyl-N-[[(2'-[[[(methylamino)carbonyl]amino]methyl]-[1,1'-biphenyl]-4-yl]-methyl]benzenebutanamide;

(R)-α-[(2-Amino-2-methyl-1-oxopropyl)amino]-N-methyl-N-[[2'-(1H-tetrazol-5-yl)[1,1'-biphenyl]-4-yl]methyl]-1H-indole-3-propanamide;

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]-1H-indole-3-propanamide;

(R)-α-[(2-Amino-2-methyl-1-oxypropyl)amino]-N-ethyl-N-[[(2'-[((methylamino)carbonyl)amino]methyl])-[1,1'-biphenyl]-4-yl]methyl]benzenebutanamide;

(R)-α-[(3-Amino-3-methyl-1-oxybutyl)amino]-N-ethyl-N-[[(2'-[[[(methylamino)carbonyl]amino]methyl]-[1,1'-biphenyl]-4-yl]methyl]benzenebutanamide;

(R)-α-[(2-Amino-2-methyl-1-oxypropyl)amino]-N-[[2'-(1H-tetrazol-5-yl)-[1,1'-biphenyl]-4-yl]methyl]-N-(propyl)benzenebutanamide;

(R)-α-[(2-Amino-2-methyl-1-oxopropyl)amino]-N-[[(2'-[(2-hydroxyethylamino)carbonyl]amino][1,1'-biphenyl]-4-yl]methyl]-3-[(phenylmethyl)oxy]propanamide;

(R)-α-[(2-Amino-2-methyl)-1-oxopropyl]amino-N-methyl-N-[(2'-[[(methylamino)carbonyl]amino]methyl][1,1'-biphenyl]-4-yl]benzenebutanamide; and (R)-α-[(2-Amino-2-methyl)-1-oxopropyl]amino-N-methyl-N-[2'-(1H-tetrazol-5-yl)[1,1'-biphenyl]-4-yl]butanamide;

and pharmaceutically acceptable salts thereof.

7. A compound which is selected from the group consisting of:

(R)-α-[(3-Amino-3-methyl-1-oxobutyl)amino]-N-[[2'-(1H-tetrazol-5-yl)[1,1'-biphenyl]-4-yl]methyl]benzene-butanamide;

(R)-α-[(3-Amino-3-methyl-1-oxobutyl)amino]-N-[[2'-(1H-tetrazol-5-yl)[1,1'-biphenyl]-4-yl]methyl]benzene-propanamide;

(R)-α-[(3-Amino-3-methyl-1-oxobutyl)amino]-N-[[2'-(1H-tetrazol-5-yl)[1,1'-biphenyl]-4-yl]methyl]-1H-indole-3-propanamide;

(R)-2-[(3-Amino-3-methyl-1-oxobutyl)amino]-N-phenyl-N-[[2'-(1H-tetrazol-5-yl)[1,1'-biphenyl]-4-yl]methyl]butanamide;

2-[(3-Amino-3-methyl-1-oxobutyl)amino]-N-[[2'-(1H-tetrazol-5-yl)[1,1'-biphenyl]-4-yl]methyl]acetamide;

(R)-α-[(2-Amino-2-methyl-1-oxopropyl)amino]-N-[[2'-[[(methylamino)carbonyl]amino][1,1'-biphenyl]-4-yl]methyl]-1H-indole-3-propanamide;

(R)-α-[(2-Amino-2-methyl-1-oxypropyl)amino]-N-methyl-N-[[2'-(1H-tetrazol-5-yl)-[1,1'-biphenyl]-4-yl]methyl]benzenebutanamide;

(R)-α-[(3-Amino-3-methyl-1-oxybutyl)amino]-N-methyl-N-[[2'-(1H-tetrazol-5-yl)-[1,1'-biphenyl]-4-yl]methyl]benzenebutanamide;

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]benzenebutanamide;

(R)-α-[(3-Amino-3-methyl-1-oxybutyl)amino]-N-methyl-N-[[(2'-[([methylamino]carbonyl)aminomethyl])-[1,1'-biphenyl]-4-yl]methyl]benzenebutanamide;

(R)-α-[(4-Amino-4-methyl-1-oxopentyl)amino]-N-methyl-N-[[2'-(1H-tetrazol-5-yl)[1,1'-biphenyl]-4-yl]methyl]benzenebutanamide;

(R)-α-[(4-Amino-4-methyl-1-oxypentyl)amino]-N-methyl-N-[[(2'-[[[(methylamino)carbonyl]amino]methyl]-[1,1'-biphenyl]-4-yl]-methyl]benzenebutanamide;

(R)-α-[(2-Amino-2-methyl-1-oxopropyl)amino]-N-methyl-N-[[2'-(1H-tetrazol-5-yl)[1,1'-biphenyl]-4-yl]methyl]-1H-indole-3-propanamide;

(R)-α-[(2-Amino-2-methyl-1-oxypropyl)amino]-N-methyl-N-[[(2'-[[[(methylamino)carbonyl]amino]methyl]-[1,1'-biphenyl]-4-yl]methyl]1H-indole-3-propanamide;

(R)-α-[(3-Amino-3-methyl-1-oxobutyl)amino]-N-[[2'-[[(methylamino)carbonyl]amino][1,1'-biphenyl]-4-yl]methyl]-1H-indole-3-propanamide;

(R)-α-[(2-Amino-2-methyl-1-oxopropyl)amino]-N-[[2'-[(2-hydroxyethylamino)carbonyl]amino][1,1'-biphenyl]-4-yl]-methyl]-1H-indole-3-propanamide;

(R)-α-[(3-Amino-3-methyl-1-oxobutyl)amino]-N-[[2'-[[(2-hydroxy-ethylamino)carbonyl]amino][1,1'-biphenyl]-4-yl]methyl]-1H-indole-3-propanamide;

(R)-α-[(2-Amino-2-methyl-1-oxypropyl)amino]-N-ethyl-N-[[2'-(1H-tetrazol-5-yl)-[1,1'-biphenyl]-4-yl]methyl]benzenebutanamide;

(R)-α-[(3-Amino-3-methyl-1-oxybutyl)amino]-N-ethyl-N-[[2'-(1H-tetrazol-5-yl)-[1,1'-biphenyl]-4-yl]methyl]benzenebutanamide;

(R)-α-[(2-Amino-2-methyl-1-oxypropyl)amino]-N-ethyl-N-[[(2'-[((methylamino)carbonyl)aminomethyl])-[1,1'-biphenyl]-4-yl]methyl]benzenebutanamide;

(R)-α-[(3-Amino-3-methyl-1-oxybutyl)amino]-N-ethyl-N-[[(2'-[[[(methylamino)carbonyl]amino]methyl]-[1,1'-biphenyl]-4-yl]methyl]benzenebutanamide;

(R)-α-[(2-Amino-2-methyl-1-oxypropyl)amino]-N-[[2'-(1H-tetrazol-5-yl)-[1,1'-biphenyl]-4-yl]methyl]-N-(propyl)benzenebutanamide;

(R)-α-[(2-Amino-2-methyl-1-oxopropyl)amino]-N-[[2'-[[(methylamino)carbonyl]amino][1,1'-biphenyl]-4-yl]methyl]-3-[(phenylmethyl)-oxy]propanamide;

(R)-α-[(3-Amino-3-methyl-1-oxobutyl)amino]-N-[[(2'-[[(methylamino)carbonyl]amino][1,1'-biphenyl]-4-yl]methyl]-3-[(phenylmethyl)oxy]propanamide;

(R)-α-[(2-Amino-2-methyl-1-oxopropyl)amino]-N-[[(2'-[(2-hydroxy-ethylamino)carbonyl]amino][1,1'-biphenyl]-4-yl]methyl]-3-[(phenyl-methyl)oxy]propanamide;

(R)-α-[(3-Amino-3-methyl-1-oxobutyl)amino]-N-[[(2'-[(2-hydroxy-ethylamino)carbonyl]amino][1,1'-biphenyl]-4-yl]methyl]-3-[(phenyl-methyl)oxy]propanamide;

(R)-α-[(2-Amino-2-methyl-1-oxypropyl)amino]-N-[[2'-(1H-tetrazol-5-yl)-[1,1'-biphenyl]-4-yl]methyl]-3-[(phenylmethyl)oxy]propanamide;

(R)-α-[(3-Amino-3-methyl-1-oxybutyl)amino]-N-[[2'-(1H-tetrazol-5-yl)-[1,1'-biphenyl]-4-yl]methyl]-3-[(phenylmethyl)oxy]propanamide;

(R)-α-[(2-Amino-2-methyl-1-oxypropyl)amino]-N-(4-methoxyphenyl)-N-[[2'-(1H-tetrazol-5-yl)-[1,1'-biphenyl]-4-yl]methyl]benzenebutanamide;

(R)-α-[(3-Amino-3-methyl-1-oxybutyl)amino]-N-(4-methoxyphenyl)-N-[[2'-(1H-tetrazol-5-yl)-[1,1'-biphenyl]-4-yl]methyl]benzenebutanamide;

(R)-α-[(2-Amino-2-methyl-1-oxypropyl)amino]-N-(4-hydroxyphenyl)-N-[[2'-(1H-tetrazol-5-yl)-[1,1'-biphenyl]-4-yl]methyl]benzene-butanamide;

(R)-α-[(2-Amino-2-methyl)-1-oxopropyl]amino-N-methyl-N-[(2'-[[(methylamino)carbonyl]amino][1,1'-biphenyl]-4-yl]-benzenebutanamide;

(R)-α-[(2-Amino-2-methyl)-1-oxopropyl]amino-N-methyl-N-[2'-(1H-tetrazol-5-yl)[1,1'-biphenyl]-4-yl]butanamide; and (R)-α-[(2-Amino-2-methyl)-1-oxopropyl]amino-N-methyl-N-[(2'-[[(methylamino)carbonyl]amino)methyl][1,1'-biphenyl]-4-yl]benzenebutanamide;

and pharmaceutically acceptable salts thereof.

* * * * *